(12) United States Patent
Brollo et al.

(10) Patent No.: US 8,828,997 B2
(45) Date of Patent: Sep. 9, 2014

(54) 2,3-DIHYDRO-1H-IMIDAZO(1,2-A) PYRIMIDIN-5-ONE DERIVATIVES, PREPARATION THEREOF, AND PHARMACEUTICAL USE THEREOF

(75) Inventors: Maurice Brollo, Paris (FR); Annie Clauss, Paris (FR); Youssef El Ahmad, Paris (FR); Bruno Filoche-Romme, Paris (FR); Frank Halley, Paris (FR); Karl Andreas Karlsson, Paris (FR); Gilbert Marciniak, Paris (FR); Baptiste Ronan, Paris (FR); Laurent Schio, Paris (FR); Bertrand Vivet, Paris (FR); Fabrice Viviani, Paris (FR); Andre Zimmermann, Paris (FR)

(73) Assignee: Sanofi, Paris (FR)

( * ) Notice: Subject to any disclaimer, the term of this patent is extended or adjusted under 35 U.S.C. 154(b) by 234 days.

(21) Appl. No.: 13/381,571

(22) PCT Filed: Jul. 1, 2010

(86) PCT No.: PCT/FR2010/051373
§ 371 (c)(1),
(2), (4) Date: Feb. 17, 2012

(87) PCT Pub. No.: WO2011/001112
PCT Pub. Date: Jan. 6, 2011

(65) Prior Publication Data
US 2012/0142679 A1   Jun. 7, 2012

Related U.S. Application Data

(60) Provisional application No. 61/241,097, filed on Sep. 10, 2009.

(30) Foreign Application Priority Data

Jul. 2, 2009 (FR) .................................... 09 03236
Oct. 9, 2009 (FR) .................................... 09 57067

(51) Int. Cl.
| A61K 31/5377 | (2006.01) |
|---|---|
| A61K 31/519 | (2006.01) |
| C07D 413/14 | (2006.01) |
| C07D 487/04 | (2006.01) |

(52) U.S. Cl.
CPC .......... *C07D 487/04* (2013.01); *A61K 31/5377* (2013.01); *C07D 413/14* (2013.01); *A61K 31/519* (2013.01)
USPC ...................... 514/233.2; 544/117

(58) Field of Classification Search
CPC ............... C07D 487/04; C07D 413/14; A61K 31/5377; A61K 31/519
USPC ........................................ 544/117; 514/233.2
See application file for complete search history.

(56) References Cited

FOREIGN PATENT DOCUMENTS

| WO | WO02/18386 A1 | 3/2002 |
|---|---|---|
| WO | WO03/027116 A2 | 4/2003 |
| WO | WO03/072579 A1 | 9/2003 |
| WO | WO2006/109081 A1 | 10/2006 |
| WO | WO2008/148074 A2 | 12/2008 |

OTHER PUBLICATIONS

Cancer and Metastasis Reviews (1998), 17(1), 91-106.*
Science (1999), vol. 286, 531-537.*
International Preliminary Report on Patentability dated Jan. 17, 2012 issued in PCT/FR2010/051373.
Wysocki, Waldemar et al., "6-Benzyl-7-hydroxy-1-(2-methoxyphenyl)-2,3-dihydro-1H,7H-imidazo[1,2-a]pyrimidin-5-one," Acta Crystallographica (2006), vol. E62, pp. o2548-o2550.
International Search Report dated Aug. 12, 2010 issued in PCT/FR2010/051373.
Susan Wee, et al., PTEN-deficient cancers depend on PIK3CB); PNAS, Sep. 2, 2008, vol. 105, No. 35, pp. 13057-13062.

* cited by examiner

*Primary Examiner* — Rebecca Anderson
(74) *Attorney, Agent, or Firm* — Scully, Scott, Murphy & Presser, P.C.

(57) ABSTRACT

The invention relates to a product of formula (I)

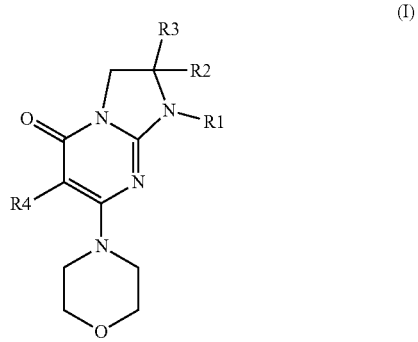

where R1, R2, R3, and R4 are as defined herein, the therapeutic use of the product, a process to make the product, and a pharmaceutical composition comprising the product.

15 Claims, No Drawings

2,3-DIHYDRO-1H-IMIDAZO(1,2-A) PYRIMIDIN-5-ONE DERIVATIVES, PREPARATION THEREOF, AND PHARMACEUTICAL USE THEREOF

CROSS-REFERENCE TO RELATED APPLICATIONS

This application claims the benefit of U.S. Provisional Application No. 61/241,097 filed on Sep. 10, 2009.

The present invention relates to novel chemical compounds (2,3-dihydro-1H-imidazo{1,2-a}pyrimidin-5-one), derived from pyrimidinones, to the process for the preparation thereof, to the novel intermediates obtained, to the use thereof as medicaments, to the pharmaceutical compositions containing them and to the novel use of such derivatives.

The present invention also relates to the use of said derivatives for the preparation of a medicament for use in treating humans.

More particularly, the invention relates to novel pyrimidinone derivatives and to the pharmaceutical use thereof for the prevention and treatment of conditions capable of being modulated by inhibition of the PI3K/AKT/mTOR pathway. AKT is a key participant in the signalling pathway. A high level of AKT phosphorylation is the mark of the activation of the pathway, which is found in many human cancers.

The products of the present invention may thus in particular be used for the prevention or treatment of conditions capable of being modulated by inhibition of AKT phosphorylation (P-AKT). The inhibition of P-AKT may especially be obtained by inhibition of the PI3K/AKT/mTOR pathway, and in particular by inhibition of kinases belonging to this pathway, for instance receptor tyrosine kinases such as EGFR, IGFR, ErbB2,3'-phosphoinositide-dependent protein kinase-1 (PDK1), the PI3K phosphoinositide kinase, the AKT serine-threonine kinase, or the mTOR kinase.

The inhibition and regulation of the PI3K/AKT/mTOR pathway constitutes in particular a new and powerful mechanism of action for the treatment of a large number of cancer diseases including solid and liquid tumours.

Such conditions that can be treated by the products of the present application are solid or liquid human tumours.

This invention also relates to novel pyrimidinone derivatives and to the pharmaceutical use thereof in the prevention and treatment of conditions affected by the modulation of autophagy. The inhibition and regulation of autophagy constitutes a new mechanism of action for treating a large number of cancer diseases, including solid and liquid tumours.

This invention also relates to novel pyrimidinone derivatives and to the pharmaceutical use thereof in the treatment of parasitic diseases such as malaria, sleeping sickness, Chagas disease or leishmaniasis.

Role of the PI3K/AKT/mTOR Pathway

The PI3K/AKT/mTOR signalling pathway is a complex network which regulates multiple cell functions, such as growth, survival, proliferation and cell growth, which are key processes in tumour regenesis.

This signalling pathway is an important target in the treatment of cancer since most of its effectors are altered in human tumours. The principle effectors contributing to the activation of the pathway are i) oncogenes, such as ErbB1 (EGFR), ErbB2 (HER2), PIK3CA and AKT, activated by mutation, amplification or overexpression; ii) a deficiency in tumour suppressor genes such as PTEN, TSC1/2, LKB and PML, which are inactivated following mutations or deletions (Jiang L-Z & Liu L-Z, Biochim Biophys Acta, 2008, 1784:150; Vivanco I & Sawyers C L, 2002, Nat Rev Cancer, 2:489; Cully M et al., Nature Rev. Cancer, 2006, 6:184).

The activation of the oncogenes of this signalling pathway is found in many human cancer diseases:
  PIK3CA activating mutations are present in 15-30% of colon, breast, endometrial, liver, ovarian and prostate cancers (T L Yuan and L C Cantley, Oncogene, 2008, 27:5497; Y. Samuels et al. Science, 2004, 304:554; K E. Bachman et al. Cancer Biol Ther, 2004, 3:772; D A Levine et al. Clin Canc Res. 2005, 11:2875; C. Hartmann et al. Acta Neuropathol. 2005, 109:639);
  amplifications, activating mutations and overexpressions of RTKs such as EGFR and HER2 in brain, breast and lung (NSCLC) cancers;
  amplification and activating overexpression of AKT in brain, lung (NSCLC), breast, kidney, ovarian and pancreatic cancers (Testa J R. and Bellacosa A., Proct. Natl. Acad. Sci. USA 2001, 98:10983; Cheng et al., Proct. Natl. Acad. Sci. USA 1992, 89: 9267; Bellacosa et al., Int. J. Cancer, 1995, 64:280; Cheng et al., Proct. Natl. Acad. Sci. USA 1996, 93:3636; Yuan et al., Oncogene, 2000, 19:2324).

Deficiency in the tumour suppressor genes of this signalling pathway is also found in many human cancer diseases:
  deletion of PTEN in 50% of lung (NSCLC), liver, kidney, prostate, breast, brain, pancreatic, endometrial and colon cancers (Maxwell G L et al. Canc. Res. 1998, 58:2500; Zhou X-P et al. Amer. J. Pathol., 2002, 161: 439; Endersby R & Baker S J, Oncogene, 2008, 27:5416; Li et al. Science, 1997, 275:1943; Steack P A et al., Nat. Genet., 1997, 15:356);
  mutations in TSC1/2 in more than 50% of tuberous scleroses;
  mutations or deletions in LKB1 (or STK11) which predispose to gastrointestinal tract cancers and to pancreatic cancer and which are found in particular in 10-38% of lung adenocarcinomas (Shah U. et al. Cancer Res. 2008, 68:3562);
  modifications of PML in particular by translocation in human tumours (Gurrieri C et al, J. NAtl Cancer Inst. 2004, 96:269).

In addition, this signalling pathway is a major factor for resistance to chemotherapy, to radiotherapy and to targeted therapies such as EGFR and HER2 inhibitors, for example (C. Sawyers et al. Nat Rev 2002).

Role of AKT

AKT (protein kinase B; PKB) is a serine-threonine kinase which occupies a central place in one of the major cell signalling pathways, the PI3K/AKT pathway. AKT is in particular involved in the growth, proliferation and survival of tumour cells. AKT activation occurs in two steps, (i) by phosphorylation of threonine 308 (P-T308) by PDK1 and (2) by phosphorylation of serine 473-(P-S473) by mTORC2 (or mTOR-Rictor complex), resulting in complete activation. AKT in turn regulates a large number of proteins, including mTOR (mammalian target of Rapamycin), BAD, GSK3, p21, p27, FOXO or FKHRL1 (Manning B D & Cantley L C, Cell, 2007 129:1261). The activation of AKT promotes the internalisation of nutrients, thereby triggering a process of anabolising metabolisation supporting cell growth and proliferation. In particular, AKT controls the initiation of protein synthesis through a cascade of interactions that occurs by means of TSC1/2 (tuberous scleroses complex), Rheb and TOR, so as to result in two essential targets of the signalling pathway, p70S6K and 4EBP. AKT also induces inhibiting phosphorylation of the Forkhead transcription factor and inactivation of GSK3β, which result in the inhibition of apoptosis and in progression of the cell cycle (Franke T F, Oncogene, 2008, 27:6473). AKT is therefore a target for anticancer therapy and the inhibition of AKT activation by inhibition of the phosphorylation thereof may induce apoptosis of malignant cells and, by the same token, provide a treatment for cancer.

Receptor Tyrosine Kinases Such as IGF1R

Abnormally high levels of protein kinase activity have been implicated in many diseases resulting from abnormal cell functions. This may originate either directly or indirectly from a dysfunction in the mechanisms for controlling the kinase activity, related to for example an inappropriate mutation, overexpression or activation of the enzyme, or owing to an overproduction or underproduction of cytokines or of growth factors, also involved in the transduction of upstream or downstream signals of kinases. In all these cases, a selective inhibition of the action of kinases leads to the hope of a beneficial effect.

The insulin-like growth factor type 1 receptor (IGF-I-R) is a transmembrane receptor tyrosine kinase which binds firstly to IGFI, but also to IGFII and to insulin with a weaker affinity. The binding of IGF1 to its receptor leads to oligomerisation of the receptor, activation of the tyrosine kinase, intermolecular autophosphorylation and phosphorylation of cell substrates (principal substrates: IRS1 and Shc). The receptor activated by its ligand induces a mitogenic activity in normal cells. However, IGF-I-R plays an important role in "abnormal" growth.

Several clinical reports underline the important role of the IGF-I pathway in the development of human cancers:
IGF-I-R is often found overexpressed in many tumour types (breast, colon, lung, sarcoma, prostate, multiple myeloma) and its presence is often associated with a more aggressive phenotype.

High concentrations of circulating IGF1 are strongly correlated with a risk of prostate, lung and breast cancer.

Furthermore, it has been widely documented that IGF-I-R is necessary for the establishment and maintenance of the transformed phenotype in vitro just as in vivo [Baserga R, Exp. Cell. Res., 1999, 253, pages 1-6]. The kinase activity of IGF-I-R is essential for the transforming activity of several oncogenes: EGFR, PDGFR, SV40 virus broad T antigen, activated Ras, Raf, and v-Src. The expression of IGF-I-R in normal fibroblasts induces a neoplastic phenotype, which can subsequently lead to tumour formation in vivo. IGF-I-R expression plays an important role in substrate-independent growth. IGF-I-R has also been shown to be a protector in chemotherapy- and radiationinduced apoptosis and cytokine-induced apoptosis. Furthermore, the inhibition of endogenous IGF-I-R by a dominant negative, the formation of a triple helix or the expression of an antisense causes a suppression of the transforming activity in vitro and a decrease in tumour growth in animal models.

PDK1

3'-Phosphoinositide-dependent protein kinase-1 (PDK1) is one of the essential components of the PI3K-AKT signalling pathway. It is a serine-threonine (Ser/Thr) kinase, the role of which is to phosphorylate and activate other Ser/Thr kinases of the AGC family that are involved in the control of cell growth, proliferation and survival and in the regulation of the metabolism. These kinases include protein kinase B (PKB or AKT), SGK (or serum and glucocorticoid regulated kinase), RSK (or p90 ribosomal S6 kinase), p70S6K (or p70 ribosomal S6 kinase) and also various isoforms of protein kinase C (PKC) (Vanhaesebroeck B. & Alessi D R., Biochem J, 2000, 346:561). One of the key roles of PDK1 is therefore the activation of AKT: in the presence of PIP3, which is the second messenger generated by PI3K, PDK-1 is recruited to the plasma membrane via its PH (plekstrin homology) domain and phosphorylates AKT on threonine 308 located in the activation loop, which is an essential modification for AKT activation. PDK1 is expressed ubiquitously and is a constitutively active kinase. PDK1 is a key element in the PI3K/AKT signalling pathway for regulating key processes in tumour genesis, such as cell proliferation and survival. Since this pathway is activated in more than 50% of human cancers, PDK1 represents a target for anticancer therapy. The inhibition of PDK1 should result in an effective inhibition of the proliferation and survival of cancer cells and therefore provide a therapeutic benefit for human cancers (Bayascas J R, Cell cycle, 2008, 7:2978; Peifer C. & Alessi D R, ChemMedChem, 2008, 3:1810).

Phosphoinositide 3-kinases (PI3Ks)

The PI3K lipid kinase is an important target in this signalling pathway for oncology. The class I PI3Ks are divided up into class Ia (PI3K$\alpha$,$\beta$,$\delta$) activated by receptor tyrosine kinases (RTKs), G protein-coupled receptors (GPCRs), GTPases of the family Rho and p21-Ras, and class Ib (PI3K$\gamma$) activated by GPCRs and p21-Ras. The class Ia PI3Ks are heterodimers which consist of a catalytic subunit p110$\alpha$, $\beta$ or $\delta$ and a regulatory subunit p85 or p55. The class Ib (p110$\gamma$) is monomeric. The class I PI3Ks are lipid/protein kinases which are activated by RTKs, GPCRs or Ras after recruitment of the membrane. These class I PI3Ks phosphorylate phosphatidylinositol 4,5-diphosphate (PIP2) on position 3 of the inositol so as to give phosphatidylinositol 3,4,5-triphosphate (PIP3), a key secondary messenger in this signalling pathway. In turn, PIP3 recruits AKT and PDK1 to the membrane, where they bind via their pleckstrin homology domain (PH domain), resulting in activation of AKT by PDK1 phosphorylation on threonine 308. AKT phosphorylates many substrates, thus playing a key role in many processes resulting in cell transformation, such as cell proliferation, growth and survival, and also angiogenesis.

The class I PI3Ks are implicated in human cancers: somatic mutations of the PIK3CA gene, which encodes PI3K$\alpha$, are found in 15-35% of human tumours, with in particular two principle oncogenic mutations, H1047R (in the kinase domain), and E545K/E542K (in the helical domain), (Y. Samuels et al. Science, 2004, 304:554; T L Yuan and L C Cantley, Oncogene, 2008, 27:5497). PI3K inhibitors are expected to be effective in the treatment of many human cancers exhibiting genetic alterations resulting in the activation of the PI3K/AKT/mTOR pathway (Vogt P. et al., Virology, 2006, 344:131; Zhao L & Vogt P K, Oncogene, 2008, 27:5486).

mTOR mTOR (mammalian target of rapamycin) is a serine-threonine kinase related to the lipid kinases of the PI3K family. mTOR has been implicated in various biological processes, including cell growth, proliferation, motility and survival. mTOR is a multifunctional kinase which integrates both the signals coming from growth factors and those coming from nutrients in order to regulate protein translation, nutrient uptake, autophagy and mitochondrial function. mTOR exists in the form of two different complexes, called mTORC1 and mTORC2. mTORC1 contains the raptor subunit and mTORC2 contains the rictor subunit. These two complexes are regulated differently: mTORC1 phosphorylates the S6 kinase (S6K) and 4EBP1, thus stimulating translation and ribosome biogenesis so as to facilitate cell growth and progression in the cell cycle. S6K also acts in a feedback pathway for reducing the activation of AKT. mTORC1 is sensitive to rapamycin, whereas mTORC2 is generally insensitive to rapamycin. mTORC2 appears to modulate growth factor signalling by phosphorylating AKT on serine residue 473.

mTOR has been implicated in various pathological conditions, including in particular cancer, diabetes, obesity, cardiovascular diseases and neurological disorders. mTOR modulates many biological processes, including translation, autophagy and ribosome biogenesis, by integrating intracellular and extracellular signals such as the signals transported by growth factors, nutrients, energy levels and the cell stress (Guertin D. A. and Sabatini D., Cancer Cell, 2007, 12:9; Menon S, and Manning B. D., Oncogene, 2009, 27:S43).

The Role of Autophagy

Autophagy is a lysosome-dependent intracellular degradation mechanism (organelles, long-lived proteins, etc.). The autophagy process involves the formation of particular vesicles called autophagosomes. The class III PI3K lipid kinase (Vps34) is involved in the formation of autophagosomes. This class III PI3K phosphorylates phosphatidylinositol (PI) on position 3 of the inositol so as to give phosphatidylinositol-3-triphosphate (PI3P). PI3P is a key second messenger in autophagosome formation via the recruitment of proteins such as WIPI, DFCP1 and Alfy. Autophagy is a cell survival mechanism which enables the cell to survive in a situation of stress, for example faced with a metabolic stress. In the case of cancer, autophagy is implicated in the resistance of tumour cells faced with environmental stresses such as: hypoxia, oxidative stresses, nutrient deficiency, but also faced with therapeutic stresses: treatment with anticancer agents, ionizing radiation.

Application in Antimalarial Chemotherapy

Malaria is one of the primary infectious causes of mortality in the world and, each year, affects 100 to 200 million individuals. The strong upsurge in the disease observed over the last few years is due to several factors, including:
- the vectors, namely *anopheles* mosquitoes, which become resistant to the conventional cheap insecticides,
- the increase in the population in the areas at risk, and, mainly,
- the resistance of numerous strains of *Plasmodium falciparum*, the parasite responsible for the lethal forms of the disease, to the medicaments conventionally used, such as chloroquine and mefloquine.

The propagation of resistance among the *Plasmodium* strains, in particular *P. falciparum*, to most of the antimalarial medicaments demonstrates the urgent need to develop new compounds having a new method of action and which thus enable a decrease in the risk of cross resistance. Human kinases are targets that have been validated in the treatment of numerous pathological conditions, and the kinome of *P. falciparum* has been proposed as a reservoir of new targets for developing new medicaments, which have not yet been explored in the treatment of malaria.

The *Plasmodium falciparum* kinome is composed of 64 kinases, some of which are orthologues of human kinases. Kinase signalling pathway inhibitors have been tested for their ability to inhibit, in vitro and in vivo, the growth of *P. falciparum* and of other pathogenic species responsible for malaria.

The molecules of the invention inhibit the growth of *P. falciparum* (highly chloroquine-resistant strain Fcm29-Cameroon) at 1 µM and 0.1 µM in an in vitro test using infected human erythrocytes, as indicated in Table 2.

Similar kinomes are present in all the *Plasmodium* species, such as *P. falciparum, P. vivax, P. malariae, P. ovale* and *P. knowlesi*. The compounds of the invention can therefore be used in the treatment of malaria induced by all the parasites mentioned above. In addition, the kinases are found in other parasites, such as *Trypanosoma* (for example *T. brucei, T. cruzei*) and *Leishmania* (for example *L. major, L. donovani*).

The compounds of the invention can therefore be used in the treatment of sleeping sickness, Chagas disease, the various forms of leishmaniasis and other parasitic infections.

Kinase-inhibiting morpholino-pyrimidinone derivatives are known to those skilled in the art.

Application WO 2008/148074 describes products which have an mTOR-inhibiting activity. These products are pyrido[1,2-a]pyrimidin-4-ones which differ from the products of the present invention owing to their entirely aromatic nature and their substitutions.

Application WO 2008/064244 describes the application of the PI3Kβ-inhibiting products TGX-221 and TGX-155 that are of use in the treatment of cancer, and in particular of breast cancer. These products are pyrido[1,2-a]pyrimidin-4-ones previously described in applications WO 2004/016607 and WO 2001/053266, which differ from the products of the present invention owing to their entirely aromatic nature and their substitutions.

Applications WO 2006/109081, WO 2006/109084 and WO 2006/126010 describe DNA-PK-inhibiting products that are of use in the treatment of ATM-deficient cancers. These products are pyrido[1,2-a]pyrimidin-4-ones which differ from the products of the present invention owing to their entirely aromatic nature and their substitutions.

Application WO 2003/024949 describes DNA-PK-inhibiting products that are of use in the treatment of ATM-deficient cancers. These products are pyrido[1,2-a]pyrimidin-4-ones which differ from the products of the present invention owing to their entirely aromatic nature and their substitutions.

The subject of the present invention is the products of formula (I):

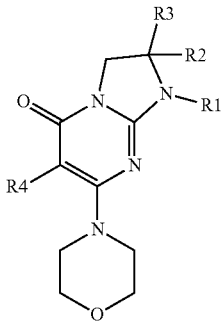

in which:

R1 represents an -L-aryl or -L-heteroaryl radical, such that L represents:
either a linear or branched alkyl radical containing from 1 to 6 carbon atoms and optionally substituted with a hydroxyl radical,
or a CO group,
or an L'-X group where L' represents a linear or branched alkyl radical containing from 1 to 6 carbon atoms, and X an oxygen or sulphur atom;
the aryl and heteroaryl radicals being optionally substituted with one or more radicals, which may be identical or different, chosen from halogen atoms and hydroxyl, CN, nitro-, —COON, —COOalk, —NRxRy, —CONRxRy, —NRxCORy, —NRxCO$_2$Rz, —CORy, alkoxy, phenoxy, alkylthio, alkyl, cycloalkyl and heterocycloalkyl radicals;
the latter alkoxy, phenoxy, alkylthio, alkyl and heterocycloalkyl radicals being themselves optionally substituted with one or more radicals, which may be identical or different, chosen from halogen atoms and NRvRw;

it being possible for the heterocycloalkyl and heteroaryl radicals to additionally contain an oxo radical;

R2 represents a hydrogen atom or an alkyl radical;

R3 represents an alkyl radical optionally substituted with one or more halogen atoms;

R4 represents a hydrogen atom or a halogen atom;

NRxRy being such that Rx represents a hydrogen atom or an alkyl radical and Ry represents a hydrogen atom or a cycloalkyl radical or an alkyl radical optionally substituted with one or more radicals, which may be identical or different, chosen from hydroxyl, alkoxy, NRvRw and heterocycloalkyl radicals; or Rx and Ry form, with the nitrogen atom to which they are attached, a cyclic radical containing from 3 to 10 ring members and optionally one or more other heteroatoms chosen from O, S, NH and N-alkyl, this cyclic radical being optionally substituted;

NRvRw being such that Rv represents a hydrogen atom or an alkyl radical and Rw represents a hydrogen atom or a cycloalkyl radical or an alkyl radical optionally substituted with one or more radicals, which may be identical or different, chosen from hydroxyl, alkoxy and heterocycloalkyl radicals; or Rv and Rw form, with the nitrogen atom to which they are attached, a cyclic radical containing from 3 to 10 ring members and optionally one or more other heteroatoms chosen from O, S, NH and N-alkyl, this cyclic radical being optionally substituted;

the cyclic radicals that Rx and Ry or Rv and Rw, respectively, can form with the nitrogen atom to which they are attached, being optionally substituted with one or more radicals, which may be identical or different, chosen from halogen atoms, and alkyl, hydroxyl, oxo, alkoxy, NH2, NHalk and N(alk)2 radicals;

Rz represents the values of Ry except for hydrogen;

Rx, Ry and Rz, in the —NRxCORy, —CORy and NRxCO₂Rz radicals, being chosen from the meanings indicated above for Rx, Ry and Rz;

said products of formula (I) being in all the possible racemic, enantiomeric and diastereoisomeric isomer forms, and also the addition salts with inorganic and organic acids or with inorganic and organic bases of said products of formula (I).

In the products of formula (I):

the term "alkyl (or alk) radical" denotes the linear, and where appropriate branched, radicals methyl, ethyl, propyl, isopropyl, butyl, isobutyl, sec-butyl, tert-butyl, pentyl, isopentyl, hexyl, isohexyl and also heptyl, octyl, nonyl and decyl, and also the linear or branched positional isomers thereof: the alkyl radicals containing from 1 to 6 carbon atoms and more particularly the alkyl radicals containing from 1 to 4 carbon atoms of the above list are preferred;

the term "alkoxy radical" denotes the linear, and where appropriate branched, radicals methoxy, ethoxy, propoxy, isopropoxy, linear, secondary or tertiary butoxy, pentoxy or hexoxy, and also the linear or branched positional isomers thereof: the alkoxy radicals containing from 1 to 4 carbon atoms of the above list are preferred;

the term "alkylthio radical" denotes the linear, and where appropriate branched, radicals methylthio, ethylthio, propylthio, isopropylthio, linear, secondary or tertiary butylthio, pentylthio or hexylthio, and also the linear or branched positional isomers thereof: the alkylthio radicals containing from 1 to 4 carbon atoms of the above list are preferred;

the term "halogen atom" denotes chlorine, bromine, iodine or fluorine atoms, and preferably the chlorine, bromine or fluorine atom;

the term "cycloalkyl radical" denotes a saturated carbocyclic radical containing 3 to 10 carbon atoms and thus denotes in particular cyclopropyl, cyclobutyl, cyclopentyl and cyclohexyl radicals, and most particularly cyclopropyl, cyclopentyl and cyclohexyl radicals;

in the —O-cycloalkyl radical, cycloalkyl is as defined above;

the term "heterocycloalkyl radical" thus denotes a monocyclic or bicyclic carbocyclic radical containing from 3 to 10 ring members, interrupted with one or more heteroatoms, which may be identical or different, chosen from oxygen, nitrogen or sulphur atoms: mention may, for example, be made of morpholinyl, thiomorpholinyl, homomorpholinyl, aziridyl, azetidyl, piperazinyl, piperidyl, homopiperazinyl, pyrrolidinyl, imidazolidinyl, pyrazolidinyl, tetrahydrofuryl, tetrahydrothienyl, tetrahydropyran, oxodihydropyridazinyl or else oxetanyl radicals, all these radicals being optionally substituted; mention may in particular be made of morpholinyl, thiomorpholinyl, homomorpholinyl, piperazinyl, piperidyl, homopiperazinyl or else pyrrolidinyl radicals;

the terms "aryl" and "heteroaryl" denote monocyclic or bicyclic, respectively carbocyclic and heterocyclic, unsaturated or partially unsaturated radicals containing at most 12 ring members, that may optionally contain a —C(O) ring member, the heterocyclic radicals containing one or more heteroatoms, which may be identical or different, chosen from O, N, or S, with N, where appropriate, being optionally substituted;

the term "aryl radical" thus denotes monocyclic or bicyclic radicals containing 6 to 12 ring members, such as, for example, phenyl, naphthyl, biphenyl, indenyl, fluorenyl and anthracenyl radicals, more particularly phenyl and naphthyl radicals, and even more particularly the phenyl radical. It may be noted that a carbocyclic radical containing a —C(O) ring member is, for example, the tetralone radical;

the term "heteroaryl radical" thus denotes monocyclic or bicyclic radicals containing 5 to 12 ring members: monocyclic heteroaryl radicals such as, for example, the radicals: thienyl, such as 2-thienyl and 3-thienyl, furyl, such as 2-furyl or 3-furyl, pyranyl, pyrrolyl, pyrrolinyl, pyrazolinyl, imidazolyl, pyrazolyl, pyridyl, such as 2-pyridyl, 3-pyridyl and 4-pyridyl, pyrazinyl, pyrimidinyl, pyridazinyl, oxazolyl, thiazolyl, isothiazolyl, diazolyl, thiadiazolyl, thiatriazolyl, oxadiazolyl, isoxazolyl, such as 3- or 4-isoxazolyl, furazanyl, free or salified tetrazolyl, all these radicals being optionally substituted, among which are more particularly the radicals: thienyl, such as 2-thienyl and 3-thienyl, furyl, such as 2-furyl, pyrrolyl, pyrrolinyl, pyrazolinyl, imidazolyl, pyrazolyl, oxazolyl, isoxazolyl, pyridyl and pyridazinyl, these radicals being optionally substituted; bicyclic heteroaryl radicals such as, for example, the radicals: benzothienyl, such as 3-benzothienyl, benzothiazolyl, quinolyl, isoquinolyl, dihydroquinolyl, quinolone, tetralone, adamentyl, benzofuryl, isobenzofuryl, dihydrobenzofuran, ethylenedioxyphenyl, thianthrenyl, benzopyrrolyl, benzimidazolyl, benzoxazolyl, thionaphthyl, indolyl, azaindolyl, indazolyl, purinyl, thienopyrazolyl, tetrahydroindazolyl, tetrahydrocyclopentapyrazolyl, dihydrofuropyrazolyl, tetrahydropyrrolopyrazolyl, oxotetrahydropyrrolopyrazolyl, tetrahydropyranopyrazolyl, tetrahydropyridinopyrazolyl or oxodihydropyridinopyrazolyl, all these radicals being optionally substituted.

As examples of heteroaryl or bicyclic radicals, mention may more particularly be made of pyrimidinyl, pyridyl, pyrrolyl, azaindolyl, indazolyl or pyrazolyl, benzothiazolyl or benzimidazolyl radicals optionally substituted with one or more substituents, which may be identical or different, as indicated above.

The carboxyl radical(s) of the products of formula (I) may be salified or esterified with the various groups known to those skilled in the art, among which mention may be made, for example of:

among the salification compounds, inorganic bases such as, for example, an equivalent of sodium, of potassium, of lithium, of calcium, of magnesium or of ammonium, or organic bases such as, for example, methylamine, propylamine, trimethylamine, diethylamine, triethylamine, N,N-dimethylethanolamine, tris (hydroxymethyl)aminomethane, ethanolamine, pyridine, picoline, dicyclohexylamine, morpholine, benzylamine, procaine, lysine, arginine, histidine and N-methylglucamine;

among the esterification compounds, the alkyl radicals for forming alkoxycarbonyl groups, such as, for example, methoxycarbonyl, ethoxycarbonyl, tert-butoxycarbonyl or benzyloxycarbonyl, it being possible for these alkyl radicals to be substituted with radicals chosen, for example, from halogen atoms and hydroxyl, alkoxy, acyl, acyloxy, alkylthio, amino or aryl radicals, such as, for example, in chloromethyl, hydroxypropyl, methoxymethyl, propionyloxymethyl, methylthiomethyl, dimethylaminoethyl, benzyl or phenethyl groups.

The addition salts with inorganic or organic acids of the products of formula (I) may, for example, be the salts formed with hydrochloric acid, hydrobromic acid, hydroiodic acid, nitric acid, sulphuric acid, phosphoric acid, propionic acid, acetic acid, trifluoroacetic acid, formic acid, benzoic acid, maleic acid, fumaric acid, succinic acid, tartaric acid, citric acid, oxalic acid, glyoxylic acid, aspartic acid, ascorbic acid, alkoylmonosulphonic acids such as, for example, methanesulphonic acid, ethanesulphonic acid or propanesulphonic acid, alkoyldisulphonic acids such as, for example, methanedisulphonic acid or alpha, beta-ethanedisulphonic acid, arylmonosulphonic acids such as benzenesulphonic acid, and aryldisulphonic acids.

It may be recalled that stereoisomerism can be defined in its broad sense as the isomerism of compounds having the same structural formulae, but the various groups of which are arranged differently in space, such as in particular in monosubstituted cyclohexanes in which the substituent may be in the axial or equatorial position, and the various possible rotational conformations of ethane derivatives. However, another type of stereoisomerism exists, due to the different spatial arrangements of fixed substituents, on double bonds or on rings, which is often referred to as geometrical isomerism or cis-transisomerism. The term "stereoisomers" is used in the present application in its broadest sense and therefore relates to all the compounds indicated above.

A subject of the present invention is the products of formula (I) as defined above, in which:

R1 represents an -L-phenyl or -L-heteroaryl radical, such that L represents:

either a linear or branched alkyl radical containing from 1 to 6 carbon atoms and optionally substituted with a hydroxyl radical, or a CO group, or an L'-X group, where L' represents a linear or branched alkyl radical containing from 1 to 6 carbon atoms, and X an oxygen or sulphur atom;

the phenyl and heteroaryl radicals being optionally substituted with one or more radicals, which may be identical or different, chosen from halogen atoms and —NRxRy, alkoxy and alkyl radicals;

the latter alkoxy and alkyl radicals being themselves optionally substituted with one or more radicals chosen from halogen atoms;

R2 represents an alkyl radical;

R3 represents an alkyl radical optionally substituted with one or more halogen atoms;

R4 represents a hydrogen atom or a fluorine atom;

NRxRy being such that Rx represents a hydrogen atom or an alkyl radical and Ry represents a hydrogen atom or an alkyl radical; or Rx and Ry form, with the nitrogen atom to which they are attached, a morpholino radical;

all the above alkyl(alk) or alkoxy radicals being linear or branched and containing from 1 to 6 carbon atoms, said products of formula (I) being in all the possible racemic, enantiomeric and diastereoisomeric isomer forms, and also the addition salts with inorganic and organic acids or with inorganic and organic bases of said products of formula (I).

In particular, when NRxRy or NRvRw forms a ring as defined above, such an amine ring may be chosen in particular from pyrrolidinyl, pyrazolidinyl, pyrazolinyl, piperidyl, azepinyl, morpholinyl, homomorpholinyl, piperazinyl or homopiperazinyl radicals, these radicals being themselves optionally substituted as indicated above or hereinafter.

The NRxRy or NRvRw ring may more particularly be chosen from the radicals: pyrrolidinyl, morpholinyl optionally substituted with one or two alkyl radicals or piperazinyl optionally substituted on the second nitrogen atom with an alkyl, phenyl or CH2-phenyl radical, themselves optionally substituted with one or more radicals, which may be identical or different, chosen from halogen atoms and alkyl, hydroxyl and alkoxy radicals.

A subject of the present invention is most particularly the products of formula (I) as defined above, corresponding to the following formulae:

(2S)-1-[2-(4-methoxyphenyl)ethyl]-2-methyl-7-(morpholin-4-yl)-2-(trifluoromethyl)-2,3-dihydroimidazo[1,2-a]pyrimidin-5(1H)one 1-[2-(4-methoxyphenyl)ethyl]-2-methyl-7-(morpholin-4-yl)-2-(trifluoro methyl)-2,3-dihydroimidazo[1,2-a]pyrimidin-5(1H)one (2S)-1-benzyl-2-methyl-7-(morpholin-4-yl)-2-(trifluoromethyl)-2,3-dihydroimidazo[1,2-a]pyrimidin-5(1H)one (2S)-2-methyl-7-(morpholin-4-yl)-1-(2-phenylethyl)-2-(trifluoromethyl)-2,3-dihydroimidazo[1,2-a]pyrimidin-5(1H)one (2S)-2-methyl-7-(morpholin-4-yl)-1-(3-phenylpropyl)-2-(trifluoromethyl)-2,3-dihydroimidazo[1,2-a]pyrimidin-5(1H)one (2S)-2-methyl-7-(morpholin-4-yl)-1-(2-phenoxyethyl)-2-(trifluoromethyl)-2,3-dihydroimidazo[1,2-a]pyrimidin-5(1H)one (2S)-2-methyl-7-(morpholin-4-yl)-1-[2-(phenylsulfanyl)ethyl]-2-(trifluoromethyl)-2,3-dihydroimidazo[1,2-a]pyrimidin-5(1H)one (2S)-2-methyl-7-(morpholin-4-yl)-1-[(2R)-2-phenylpropyl]-2-(trifluoromethyl)-2,3-dihydroimidazo[1,2-a]pyrimidin-5(1H)one (2S)-2-methyl-7-(morpholin-4-yl)-1-[(2S)-2-phenylpropyl]-2-(trifluoromethyl)-2,3-dihydroimidazo[1,2-a]pyrimidin-5(1H)one (2S)-1-[(2S)-2-hydroxy-2-phenylethyl]-2-methyl-7-(morpholin-4-yl)-2-(trifluoromethyl)-2,3-dihydroimidazo[1,2-a]pyrimidin-5(1H)one (2S)-1-[(2R)-2-hydroxy-2-phenylethyl]-2-methyl-7-(morpholin-4-yl)-2-(trifluoromethyl)-2,3-dihydroimidazo[1,2-a]pyrimidin-5(1H)one (2S)-2-methyl-7-(morpholin-4-yl)-1-[(2S)-1-phenylpropan-2-yl]-2-(trifluoromethyl)-2,3-dihydroimidazo[1,2-a]pyrimidin-5(1H)one (2S)-2-methyl-7-(morpholin-4-yl)-1-[(1S)-1-phenylpropyl]-2-(trifluoromethyl)-2,3-dihydroimidazo[1,2-a]pyrimidin-5(1H)one (2S)-2-methyl-7-(morpholin-4-yl)-1-[(1R)-1-phenylpropyl]-2-(trifluoromethyl)-2,3-dihydroimidazo[1,2-a]pyrimidin-5(1H)one (2S)-2-methyl-7-(morpholin-4-yl)-1-{2-[4-(morpholin-4-yl)phenyl]ethyl}-2-(trifluoromethyl)-2,3-dihydroimidazo[1,2-a]pyrimidin-5(1H)one (2S)-2-methyl-7-(morpholin-4-yl)-1-(1-phenylethyl)-2-(trifluoromethyl)-2,3-dihydroimidazo[1,2-a]pyrimidin-5(1H)one 1-[2-(4-methoxyphenyl)ethyl]-2,2-dimethyl-7-(morpholin-4-yl)-2,3-dihydroimidazo[1,2-a]pyrimidin-5(1H)one and also the addition salts with inorganic and organic acids or with inorganic and organic bases, of said products of formula (I).

A subject of the present invention is in particular the products of formula (I) as defined above, corresponding to the following formulae:

(2S)-6-fluoro-1-[2-(4-methoxyphenyl)ethyl]-2-methyl-7-(morpholin-4-yl)-2-(trifluoromethyl)-2,3-dihydroimidazo[1,2-a]pyrimidin-5(1H)one (2S)-1-benzyl-6-fluoro-2-methyl-7-(morpholin-4-yl)-2-(trifluoromethyl)-2,3-dihydroimidazo[1,2-a]pyrimidin-5(1H)one (2S)-6-fluoro-1-[2-(4-methoxyphenyl)ethyl]-2-methyl-7-(morpholin-4-yl)-2-(trifluoromethyl)-2,3-dihydroimidazo[1,2-a]pyrimidin-5(1H)one (2S)-1-benzyl-6-fluoro-2-methyl-7-(morpholin-4-yl)-2-(trifluoromethyl)-2,3-dihydroimidazo[1,2-a]pyrimidin-5(1H)one (2S)-1-[(5-chloro-1-benzothiophen-3-yl)methyl]-2-methyl-7-(morpholin-4-yl)-2-(trifluoromethyl)-2,3-dihydroimidazo[1,2-a]pyrimidin-5(1H)one (2S)-2-methyl-7-(morpholin-4-yl)-1-(phenylcarbonyl)-2-(trifluoromethyl)-2,3-dihydroimidazo[1,2-a]pyrimidin-5(1H)one (2S)-1-[(1R or 1S)-1-(3-fluorophenyl)ethyl]-2-methyl-7-(morpholin-4-yl)-2-(trifluoromethyl)-2,3-dihydroimidazo[1,2-a]pyrimidin-5(1H)one (2S)-1-{[4-chloro-2-(trifluoromethyl)quinolein-6-yl]methyl}-2-methyl-7-(morpholin-4-yl)-2-(trifluoromethyl)-2,3-dihydroimidazo[1,2-a]pyrimidin-5(1H)one trifluoroacetate (2S)-1-(3-bromo-4-fluorobenzyl)-2-methyl-7-(morpholin-4-yl)-2-(trifluoromethyl)-2,3-dihydroimidazo[1,2-a]pyrimidin-5(1H)one (2S)-1-(2,3-difluorobenzyl)-2-methyl-7-(morpholin-4-yl)-2-(trifluoromethyl)-2,3-dihydroimidazo[1,2-a]pyrimidin-5(1H)one (2S)-1-[2-(3-methoxyphenyl)ethyl]-2-methyl-7-(morpholin-4-yl)-2-(trifluoromethyl)-2,3-dihydroimidazo[1,2-a]pyrimidin-5(1H)one (2S)-1-[2-(2-chlorophenyl)ethyl]-2-methyl-7-(morpholin-4-yl)-2-(trifluoromethyl)-2,3-dihydroimidazo[1,2-a]pyrimidin-5(1H)one (2S)-1-[2-(4-chlorophenyl)ethyl]-2-methyl-7-(morpholin-4-yl)-2-(trifluoromethyl)-2,3-dihydroimidazo[1,2-a]pyrimidin-5(1H)one (2S)-1-[2-(3-chlorophenyl)ethyl]-2-methyl-7-(morpholin-4-yl)-2-(trifluoromethyl)-2,3-dihydroimidazo[1,2-a]pyrimidin-5(1H)one (2S)-1-(1,3-benzoxazol-2-ylmethyl)-2-methyl-7-(morpholin-4-yl)-2-(trifluoromethyl)-2,3-dihydroimidazo[1,2-a]pyrimidin-5(1H)one (2S)-2-methyl-7-(morpholin-4-yl)-1-[(1R or 1S)-1-phenylethyl]-2-(trifluoromethyl)-2,3-dihydroimidazo[1,2-a]pyrimidin-5(1H)one (2S)-2-methyl-7-(morpholin-4-yl)-1-[(1R or 1S)-1-phenylethyl]-2-(trifluoromethyl)-2,3-dihydroimidazo[1,2-a]pyrimidin-5(1H)one (2S)-1-(1H-indol-3-ylmethyl)-2-methyl-7-(morpholin-4-yl)-2-(trifluoromethyl)-2,3-dihydroimidazo[1,2-a]pyrimidin-5(1H)one (2S)-1-[(2-chlorophenyl)carbonyl]-2-methyl-7-(morpholin-4-yl)-2-(trifluoromethyl)-2,3-dihydroimidazo[1,2-a]pyrimidin-5(1H)one (2S)-2-methyl-1-[(2-methylphenyl)carbonyl]-7-(morpholin-4-yl)-2-(trifluoromethyl)-2,3-dihydroimidazo[1,2-a]pyrimidin-5(1H)one (2S)-1-[(1R or 1S)-1-(2-fluorophenyl)ethyl]-2-methyl-7-(morpholin-4-yl)-2-(trifluoromethyl)-2,3-dihydroimidazo[1,2-a]pyrimidin-5(1H)one (2S)-1-[(1R or 1S)-1-(2-fluorophenyl)ethyl]-2-methyl-7-(morpholin-4-yl)-2-(trifluoromethyl)-2,3-dihydroimidazo[1,2-a]pyrimidin-5(1H)one (S)-1-[2-(2-fluoro-4,5-dimethoxyphenyl)-2-hydroxyethyl]-2-methyl-7-morpholin-4-yl-2-trifluoromethyl-2,3-dihydro-1H-imidazo[1,2-a]pyrimidin-5-one (S)-1-[(S)-2-hydroxy-2-(2-methoxyphenyl)ethyl]-2-methyl-7-morpholin-4-yl-2-trifluoromethyl-2,3-dihydro-1H-imidazo[1,2-a]pyrimidin-5-one (S)-1-[(S)-2-(4-chloro-2-methoxyphenyl)-2-hydroxyethyl]-2-methyl-7-morpholin-4-yl-2-trifluoromethyl-2,3-dihydro-1H-imidazo[1,2-a]pyrimidin-5-one (S)-1-[(S)-2-(4-fluoro-2-methoxyphenyl)-2-hydroxyethyl]-2-methyl-7-morpholin-4-yl-2-trifluoromethyl-2,3-dihydro-1H-imidazo[1,2-a]pyrimidin-5-one (S)-1-[(S)-2-(2-chloro-4-methoxyphenyl)-2-hydroxyethyl]-2-methyl-7-morpholin-4-yl-2-trifluoromethyl-2,3-dihydro-1H-imidazo[1,2-a]pyrimidin-5-one and also the addition salts with inorganic and organic acids or with inorganic and organic bases of said products of formula (I).

A subject of the present invention is also any process for preparing the products of formula (I) as defined above.

The products according to the invention can be prepared using conventional organic chemistry methods.

Preparation of Compounds of Formula (I)

General Scheme 1 below illustrates the methods used for preparing the products of formula (I). In this respect, they cannot constitute a limitation of the scope of the invention, as regards the methods for preparing the claimed compounds.

The products of formula (I) as defined above according to the present invention may thus in particular be prepared according to the process described in General Scheme 1.

A subject of the present invention is thus also the process for preparing products of formula (I) according to General Scheme 1 as defined hereinafter.

General Scheme 1:

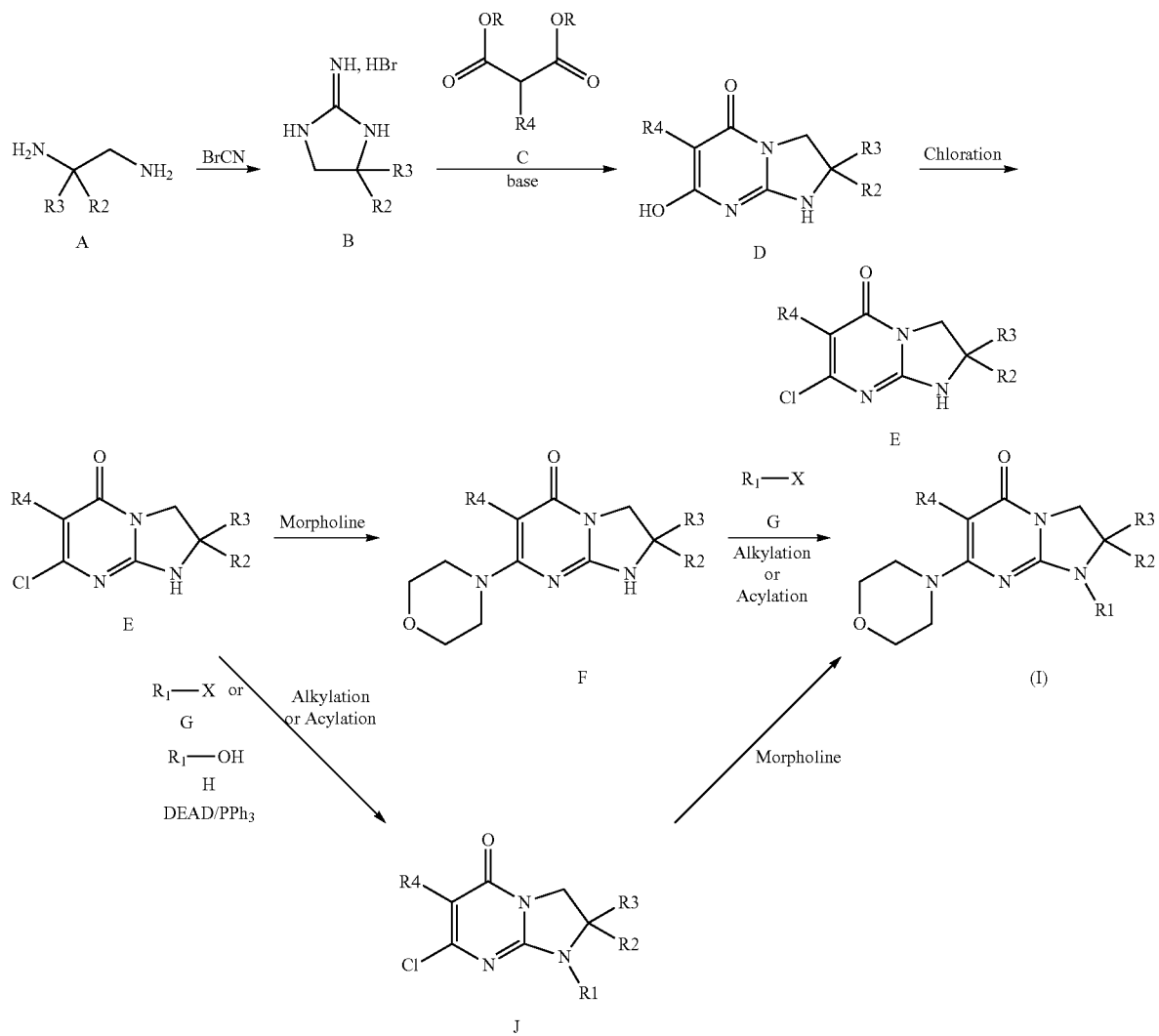

In General Scheme 1:

The diamines A are either commercially available or are prepared, in the chiral or racemic version, according to the process described by T. Brigaud, et al., in J. Org. Chem. 2006, 71(18), 7075-7078, when R2=CF$_3$ and R3=Me or by analogy with this same reference in the other cases.

The guanidines B can be obtained by reacting a diamine A and cyanogen bromide in a solvent such as water or acetonitrile, at a temperature of between 0° C. and the boiling point of the solvent, according to the conditions described, for example, by T. Gallet, et al, (EP1340761 2003).

The compounds D can be obtained by condensation of a guanidine B with a dialkyl (preferably diethyl) malonate C, in the presence of a base such as sodium methoxide, at a temperature of between 60° C. and 100° C., as described, for example, by Badawey E.-S.A.M. et al. (Eur J Med Chem, 1998, 33(5), 349-361.

The compounds E can be obtained from a compound D by treatment with a chlorinating agent such as phosphorus oxychloride in the absence of solvent, at a temperature of between 20° C. and 120° C., or in the presence of a solvent such as dichloroethane, at a temperature between 20° C. and the boiling point of the solvent, for instance under the conditions described by Yamashita, A. et al. (Syn. Commun. (2004), 34(5), 795-803).

The compounds F can be obtained from a compound E by reaction with morpholine, in the absence of solvent, at a temperature between 20° C. and 120° C., or in the presence of a solvent such as acetonitrile, at a temperature of between 20° C. and the reflux temperature of the solvent, as described, for example, by Aliabiev S. B. (Lett. Org. Chem. (2007), 4(4), 273-280.

The compounds (I) can be obtained by means of an alkylation or acylation reaction, by addition of a compound G (R1-X with R1=L-aryl or heteroaryl as defined above and X=Cl, Br, I or OTf in the case of an alkylation and X=Cl in the case of an acylation) to a mixture of a compound F and of a base such as sodium hydride or caesium carbonate in excess, in a solvent such as tetrahydrofuran, N,N-dimethylformamide or acetonitrile, at a temperature between 0° C. and 80° C., as described, for example, by Ting P. C. et al. (J. Med. Chem. (1990), 33(10), 2697-2706) in the case of the alkylation reaction.

According to the procedure described by E. P. Seest et al., in Tet. Assymetry 17 (2006) 2154-2182, the compounds G corresponding to chiral 1-aryl-2-chloroethanols or 1-heteroaryl-2-chloroethanols were synthesized from the corresponding chloroketone derivatives, which are themselves derived from the chlorination, under standard conditions, of the commercially available acetyl derivatives.

Alternatively, the compounds (1) can be obtained from a compound J by reaction with morpholine, in the absence of solvent, at a temperature between 20° C. and 120° C., or in the presence of a solvent such as acetonitrile, at a temperature of between 20° C. and the reflux temperature of the solvent, as described, for example, by Aliabiev S. B. (Lett. Org. Chem. (2007), 4(4), 273-280.

The compounds J can be obtained by means of an alkylation or acylation reaction, by addition of a compound G (R1-X with R1=L-aryl or heteroaryl as defined above and X=Cl, Br, I or OTf in the case of an alkylation and X=Cl in the case of an acylation) to a mixture of a compound F and of a base such as sodium hydride or caesium carbonate in excess, in a solvent such as tetrahydrofuran, N,N-dimethylformamide or acetonitrile, at a temperature of between 0° C. and 80° C., as described, for example, by Ting P. C. et al. (J. Med. Chem. (1990), 33(10), 2697-2706) in the case of the alkylation reaction.

Alternatively, the compounds J can be obtained by means of a Mitsunobu reaction between a compound E and an alcohol H, in the presence of diethyl azodicarboxylate and of triphenylphosphine (optionally supported on a resin), in a solvent such as tetrahydrofuran, at a temperature of between 0° C. and 65° C., as described, for example, by Mitsunobu O. et al. (Synthesis (1981), 1-28).

When R2 is different from R3 and if the synthesis is not stereoselective, the enantiomers or the possible diastereoisomers of the synthesis intermediates or of the compounds (I) can be separated by chromatography on a chiral support.

The following examples of products of formula (I) illustrate the invention without, however, limiting it.

Among the starting products of formula A, B or C, some are known and can be obtained either commercially or according to the usual methods known to those skilled in the art, for example starting from commercially available products.

It is understood, for those skilled in the art, that, in order to implement the processes according to the invention, described above, it may be necessary to introduce protective groups for amino, carboxyl and alcohol functions in order to prevent side reactions.

The following nonexhaustive list of examples of protection of reactive functions may be mentioned:
  hydroxyl groups can be protected, for example, with alkyl radicals such as tert-butyl, trimethylsilyl, tert-butyldimethylsilyl, methoxymethyl, tetrahydropyranyl, benzyl or acetyl,
  amino groups can be protected, for example, with acetyl, trityl, benzyl, tert-butoxycarbonyl, BOC, benzyloxycarbonyl or phthalimido radicals or other radicals known in peptide chemistry.

Acid functions can be protected, for example, in the form of esters formed with readily cleavable esters such as benzyl or tert-butyl esters, or esters known in peptide chemistry.

A list of various protective groups that can be used will be found in the manuals known to those skilled in the art, and for example in patent BF 2 499 995.

It may be noted that it is possible, if desired and if necessary, to subject intermediate products or products of formula (I) thus obtained by means of the processes indicated above, in order to obtain other intermediates or other products of formula (I), to one or more conversion reactions known to those skilled in the art, such as, for example:

a) a reaction for esterification of an acid function,
b) a reaction for saponification of an ester function to give an acid function,
c) a reaction for reduction of the free or esterified carboxyl function to give an alcohol function,
d) a reaction for conversion of an alkoxy function to give a hydroxyl function, or else of a hydroxyl function to give an alkoxy function,
e) a reaction for removal of the protective groups that the protected reactive functions may be carrying,
f) a reaction for salification with an inorganic or organic acid or with a base so as to obtain the corresponding salt,
g) a reaction for resolving the racemic forms to give resolved products,
said products of formula (I) thus obtained being in all the possible racemic, enantiomeric and diastereoisomeric isomer forms.

The reactions a) to g) can be carried out under the usual conditions known to those skilled in the art, such as, for example, those indicated hereinafter.

a) The products described above may, if desired, be the subject, on the possible carboxyl functions, of esterification reactions which can be carried out according to the usual methods known to those skilled in the art.
b) The possible conversions of ester functions to give acid functions of the products described above may, if desired, be carried out under the usual conditions known to those skilled in the art, in particular by acid or alkaline hydrolysis, for example with sodium hydroxide or potassium hydroxide in an alcohol medium such as, for example, in methanol, or else with hydrochloric acid or sulphuric acid.

The saponification reaction can be carried out according to the usual methods known to those skilled in the art, such as, for example, in a solvent such as methanol or ethanol, dioxane or dimethoxyethane, in the presence of sodium hydroxide or of potassium hydroxide.

c) The possible free or esterified carboxyl functions of the products described above may, if desired, be reduced to give alcohol functions by means of the methods known to those skilled in the art: the possible esterified carboxyl functions may, if desired, be reduced to give alcohol functions by means of the methods known to those skilled in the art, and in particular with lithium aluminium hydride in a solvent such as, for example, tetrahydrofuran, or else dioxane or ethyl ether.

The possible free carboxyl functions of the products described above may, if desired, be reduced to give alcohol functions in particular with boron hydride.

d) The possible alkoxy functions, such as in particular methoxy functions, of the products described above may, if necessary, be converted to hydroxyl functions under the usual conditions known to those skilled in the art, for example with boron tribromide in a solvent such as, for example, methylene chloride, with pyridine hydrobromide or hydrochloride or else with hydrobromic acid or hydrochloric acid in water or trifluoroacetic acid at reflux.

e) The removal of protective groups such as, for example, those indicated above can be carried out under the usual conditions known to those skilled in the art, in particular by acid hydrolysis carried out with an acid such as hydrochloric acid, benzenesulphonic acid, para-toluenesulphonic acid, formic acid or trifluoroacetic acid, or else by catalytic hydrogenation.

The phthalimido group may be removed with hydrazine.

f) The products described above may, if desired, be the subject of salification reactions, for example with an inorganic or organic acid or with an inorganic or organic base, according to the usual methods known to those skilled in the art: such a salification reaction can be carried out, for example, in the presence of hydrochloric acid, or else of tartaric acid, citric acid or methanesulphonic acid, in an alcohol such as, for example, ethanol or methanol.

g) The possible optically active forms of the products described above can be prepared by resolving the racemic mixtures according to the usual methods known to those skilled in the art.

The products of formula (I) as defined above, and also the addition salts thereof with acids, have advantageous pharmacological properties, in particular due to their kinase-inhibiting properties, as is indicated above.

The products of the present invention are in particular of use in tumour therapy.

The products of the invention may also thus increase the therapeutic effects of commonly used antitumour agents.

These properties justify the use thereof in therapy, and a subject of the invention is in particular, as medicaments, the products of formula (I) as defined above, said products of formula (I) being in all the possible racemic, enantiomeric and diastereoisomeric isomer forms, and also the pharmaceutically acceptable addition salts with inorganic and organic acids or with inorganic and organic bases, of said products of formula (I).

A subject of the invention is most particularly, as medicaments, the products corresponding to the following formulae:

(2S)-1-[2-(4-methoxyphenyl)ethyl]-2-methyl-7-(morpholin-4-yl)-2-(trifluoromethyl)-2,3-dihydroimidazo[1,2-a]pyrimidin-5(1H)one 1-[2-(4-methoxyphenyl)ethyl]-2-methyl-7-(morpholin-4-yl)-2-(trifluoromethyl)-2,3-dihydroimidazo[1,2-a]pyrimidin-5(1H)one (2S)-1-benzyl-2-methyl-7-(morpholin-4-yl)-2-(trifluoromethyl)-2,3-dihydroimidazo[1,2-a]pyrimidin-5(1H)one (2S)-2-methyl-7-(morpholin-4-yl)-1-(2-phenylethyl)-2-(trifluoromethyl)-2,3-dihydroimidazo[1,2-a]pyrimidin-5(1H)one (2S)-2-methyl-7-(morpholin-4-yl)-1-(3-phenylpropyl)-2-(trifluoromethyl)-2,3-dihydroimidazo[1,2-a]pyrimidin-5(1H)one (2S)-2-methyl-7-(morpholin-4-yl)-1-(2-phenoxyethyl)-2-(trifluoromethyl)-2,3-dihydroimidazo[1,2-a]pyrimidin-5(1H)one (2S)-2-methyl-7-(morpholin-4-yl)-1-[2-(phenylsulfanyl)ethyl]-2-(trifluoromethyl)-2,3-dihydroimidazo[1,2-a]pyrimidin-5(1H)one (2S)-2-methyl-7-(morpholin-4-yl)-1-[(2R)-2-phenylpropyl]-2-(trifluoromethyl)-2,3-dihydroimidazo[1,2-a]pyrimidin-5(1H)one (2S)-2-methyl-7-(morpholin-4-yl)-1-[(2S)-2-phenylpropyl]-2-(trifluoromethyl)-2,3-dihydroimidazo[1,2-a]pyrimidin-5(1H)one (2S)-1-[(2S)-2-hydroxy-2-phenylethyl]-2-methyl-7-(morpholin-4-yl)-2-(trifluoromethyl)-2,3-dihydroimidazo[1,2-a]pyrimidin-5(1H)one (2S)-1-[(2R)-2-hydroxy-2-phenylethyl]-2-methyl-7-(morpholin-4-yl)-2-(trifluoromethyl)-2,3-dihydroimidazo[1,2-a]pyrimidin-5(1H)one (2S)-2-methyl-7-(morpholin-4-yl)-1-[(2S)-1-phenylpropan-2-yl]-2-(trifluoromethyl)-2,3-dihydroimidazo[1,2-a]pyrimidin-5(1H)one (2S)-2-methyl-7-(morpholin-4-yl)-1-[(1S)-1-phenylpropyl]-2-(trifluoromethyl)-2,3-dihydroimidazo[1,2-a]pyrimidin-5(1H)one (2S)-2-methyl-7-(morpholin-4-yl)-1-[(1R)-1-phenylpropyl]-2-(trifluoromethyl)-2,3-dihydroimidazo[1,2-a]pyrimidin-5(1H)one (2S)-2-methyl-7-(morpholin-4-yl)-1-{2-[4-(morpholin-4-yl)phenyl]ethyl}-2-(trifluoromethyl)-2,3-dihydroimidazo[1,2-a]pyrimidin-5(1H)one (2S)-2-methyl-7-(morpholin-4-yl)-1-(1-phenylethyl)-2-(trifluoromethyl)-2,3-dihydroimidazo[1,2-a]pyrimidin-5(1H)one 1-[2-(4-methoxyphenyl)ethyl]-2,2-dimethyl-7-(morpholin-4-yl)-2,3-dihydroimidazo[1,2-a]pyrimidin-5(1H)one (2S)-6-fluoro-1-[2-(4-methoxyphenyl)ethyl]-2-methyl-7-(morpholin-4-yl)-2-(trifluoromethyl)-2,3-dihydroimidazo[1,2-a]pyrimidin-5(1H)one (2S)-1-benzyl-6-fluoro-2-methyl-7-(morpholin-4-yl)-2-(trifluoromethyl)-2,3-dihydroimidazo[1,2-a]pyrimidin-5(1H)one (2S)-1-[(5-chloro-1-benzothiophen-3-yl)methyl]-2-methyl-7-(morpholin-4-yl)-2-(trifluoromethyl)-2,3-dihydroimidazo[1,2-a]pyrimidin-5(1H)one (2S)-2-methyl-7-(morpholin-4-yl)-1-(phenylcarbonyl)-2-(trifluoromethyl)-2,3-dihydroimidazo[1,2-a]pyrimidin-5(1H)one (2S)-1-[(1R or 1S)-1-(3-fluorophenyl)ethyl]-2-methyl-7-(morpholin-4-yl)-2-(trifluoromethyl)-2,3-dihydroimidazo[1,2-a]pyrimidin-5(1H)one (2S)-1-{[4-chloro-2-(trifluoromethyl)quinolein-6-yl]methyl}-2-methyl-7-(morpholin-4-yl)-2-(trifluoromethyl)-2,3-dihydroimidazo[1,2-a]pyrimidin-5(1H)one trifluoroacetate (2S)-1-(3-bromo-4-fluorobenzyl)-2-methyl-7-(morpholin-4-yl)-2-(trifluoromethyl)-2,3-dihydroimidazo[1,2-a]pyrimidin-5(1H)one (2S)-1-(2,3-difluorobenzyl)-2-methyl-7-(morpholin-4-yl)-2-(trifluoromethyl)-2,3-dihydroimidazo[1,2-a]pyrimidin-5(1H)one (2S)-1-[2-(3-methoxyphenyl)ethyl]-2-methyl-7-(morpholin-4-yl)-2-(trifluoromethyl)-2,3-dihydroimidazo[1,2-a]pyrimidin-5(1H)one (2S)-1-[2-(2-chlorophenyl)ethyl]-2-methyl-7-(morpholin-4-yl)-2-(trifluoromethyl)-2,3-dihydroimidazo[1,2-a]pyrimidin-5(1H)one (2S)-1-[2-(4-chlorophenyl)ethyl]-2-methyl-7-(morpholin-4-yl)-2-(trifluoromethyl)-2,3-dihydroimidazo[1,2-a]pyrimidin-5(1H)one (2S)-1-[2-(3-chlorophenyl)ethyl]-2-methyl-7-(morpholin-4-yl)-2-(trifluoromethyl)-2,3-dihydroimidazo[1,2-a]pyrimidin-5(1H)one (2S)-1-(1,3-benzoxazol-2-ylmethyl)-2-methyl-7-(morpholin-4-yl)-2-(trifluoromethyl)-2,3-dihydroimidazo[1,2-a]pyrimidin-5(1H)one (2S)-2-methyl-7-(morpholin-4-yl)-1-[(1R or 1S)-1-phenylethyl]-2-(trifluoromethyl)-2,3-dihydroimidazo[1,2-a]pyrimidin-5(1H)one (2S)-2-methyl-7-(morpholin-4-yl)-1-[(1R or 1S)-1-phenylethyl]-2-(trifluoromethyl)-2,3-dihydroimidazo[1,2-a]pyrimidin-5(1H)one (2S)-1-(1H-indol-3-ylmethyl)-2-methyl-7-(morpholin-4-yl)-2-(trifluoromethyl)-2,3-dihydroimidazo[1,2-a]pyrimidin-5(1H)one (2S)-1-[(2-chlorophenyl)carbonyl]-2-methyl-7-(morpholin-4-yl)-2-(trifluoromethyl)-2,3-dihydroimidazo[1,2-a]pyrimidin-5(1H)one (2S)-2-methyl-1-[(2-methylphenyl)carbonyl]-7-(morpholin-4-yl)-2-(trifluoromethyl)-2,3-dihydroimidazo[1,2-a]pyrimidin-5(1H)one (2S)-1-[(1R or 1S)-1-(2-fluorophenyl)ethyl]-2-methyl-7-(morpholin-4-yl)-2-(trifluoromethyl)-2,3-dihydroimidazo[1,2-a]pyrimidin-5(1H)one (2S)-1-[(1R or 1S)-1-(2-fluorophenyl)ethyl]-2-methyl-7-(morpholin-4-yl)-2-(trifluoromethyl)-2,3-dihydroimidazo[1,2-a]pyrimidin-5(1H)one (S)-1-[2-(2-fluoro-4,5-dimethoxyphenyl)-2-hydroxyethyl]-2-methyl-7-morpholin-4-yl-2-trifluoromethyl-2,3-dihydro-1H-imidazo[1,2-a]pyrimidin-5-one (S)-1-[(S)-2-hydroxy-2-(2-methoxyphenyl)ethyl]-2-methyl-7-morpholin-4-yl-2-trifluoromethyl-2,3-dihydro-1H-imidazo[1,2-a]pyrimidin-5-one (S)-1-[(S)-2-(4-chloro-2-methoxyphenyl)-2-hydroxyethyl]-2-methyl-7-morpholin-4-yl-2-trifluoromethyl-2,3-dihydro-1H-imidazo[1,2-a]pyrimidin-5-one (S)-1-[(S)-2-(4-fluoro-2-methoxyphenyl)-2-hydroxyethyl]-2-methyl-7-morpholin-4-yl-2-trifluoromethyl-2,3-dihydro-1H-imidazo[1,2-a]pyrimidin-5-one (S)-1-[(S)-2-(2-chloro-4-methoxyphenyl)-2-hydroxyethyl]-2-methyl-7-morpholin-4-yl-2-trifluoromethyl-2,3-dihydro-1H-imidazo[1,2-a]pyrimidin-5-one and also the pharmaceutically acceptable addition salts with inorganic and organic acids or with inorganic and organic bases, of said products of formula (I).

The invention also relates to pharmaceutical compositions containing, as active ingredient, at least one of the products of formula (I) as defined above or a pharmaceutically acceptable salt of this product or a prodrug of this product and, where appropriate, a pharmaceutically acceptable carrier.

The invention thus extends to the pharmaceutical compositions containing, as active ingredient, at least one of the medicaments as defined above.

Such pharmaceutical compositions of the present invention may also, where appropriate, contain active ingredients of other antimitotic medicaments, such as in particular those based on taxol, cis-platin, DNA intercalating agents, and the like.

These pharmaceutical compositions may be administered orally, parenterally or locally by topical application to the skin or the mucous membranes, or by intravenous or intramuscular injection.

These compositions may be solid or liquid and may be in all the pharmaceutical forms commonly used in human medicine, for instance simple or sugar-coated tablets, pills, lozenges, gel capsules, drops, granules, injectable preparations, ointments, creams or gels; they are prepared according to the usual methods. The active ingredient may be incorporated therein in excipients normally used in these pharmaceutical compositions, such as talc, gum arabic, lactose, starch, magnesium stearate, cocoa butter, aqueous or nonaqueous carriers, fatty substances of animal or plant origin, paraffin derivatives, glycols, various wetting agents, dispersants or emulsifiers, or preservatives.

The usual dosage, which is variable depending on the product used, the individual treated and the condition in question, may, for example, be from 0.05 to 5 g per day in adults, or preferably from 0.1 to 2 g per day.

A subject of the present invention is also the use of products of formula (I) as defined above, for the preparation of a medicament for use in the treatment or prevention of a disease characterized by the disregulation of the activity of a protein or lipid kinase.

A subject of the present invention is in particular the use of a product of formula (I) as defined above, for the preparation of a medicament for use in the prevention or treatment of various diseases, such as cardiovascular diseases, including in particular thrombosis.

Such a medicament may in particular be intended for use in the treatment or prevention of a disease in a mammal.

A subject of the present invention is in particular the use of a product of the formula (I) as defined above, for the preparation of a medicament for use in the prevention or treatment of diseases associated with an uncontrolled proliferation.

A subject of the present invention is thus most particularly the use of a product of formula (I) as defined above, for the preparation of a medicament for use in the treatment or prevention of diseases in oncology, and in particular for use in the treatment of cancers.

Among these cancers, the focus is on the treatment of solid or liquid tumours, and on the treatment of cancers resistant to cytotoxic agents.

The cited products of the present invention may especially be used for the treatment of primary tumours and/or metastases, in particular in gastric, hepatic, renal, ovarian, colon, prostate, endometrial and lung (NSCLC and SCLC) cancers, glioblastomas, thyroid, bladder and breast cancers, in melanoma, in lymphoid or myeloid haematopoietic tumours, in sarcomas, in brain, larynx and lymphatic system cancers, bone and pancreatic cancers, and in hamartomas. Also involved are, in particular, diseases which exhibit genetic anomalies that result in the activation of the PI3K/AKT/mTOR pathway and/or in the activation of the MAP kinase pathway.

A subject of the present invention is also the use of the products of formula (I) as defined above, for the preparation of medicaments for use in cancer chemotherapy.

A subject of the present invention is thus the products of formula (I) as defined above, for the use thereof in the treatment of cancers.

A subject of the present invention is the products of formula (I) as defined above, for the use thereof in the treatment of solid or liquid tumours.

A subject of the present invention is therefore the products of formula (I) as defined above, for the use thereof in the treatment of cancers resistant to cytotoxic agents.

A subject of the present invention is therefore the products of formula (I) as defined above, for the use thereof in the treatment of primary tumours and/or metastases, in particular in gastric, hepatic, renal, ovarian, colon, prostate, endometrial and lung (NSCLC and SCLC) cancers, glioblastomas, thyroid, bladder and breast cancers, in melanoma, in lymphoid or myeloid haematopoietic tumours, in sarcomas, in brain, larynx and lymphatic system cancers, bone and pancreatic cancers, and in hamartomas.

A subject of the present invention is therefore the products of formula (I) as defined above, for the use thereof in cancer chemotherapy.

A subject of the present invention is therefore the products of formula (I) as defined above, for the use thereof in cancer chemotherapy, alone or in combination.

Such medicaments for use in cancer chemotherapy may be used alone or in combination.

The products of the present invention may in particular be administered alone or in combination with chemotherapy or radiotherapy or else in combination, for example, with other therapeutic agents.

Such therapeutic agents may be commonly used antitumour agents.

A therapeutic benefit can in particular be expected by administering the products of the present application in combinations with varied targeted therapies. These targeted therapies are in particular the following: i) therapies which inhibit the MAP kinase signalling pathway, for instance therapies which inhibit RAS, RAF, MEK or ERK; ii) targeted therapies which inhibit the kinases or pseudokinases of the PI3K/AKT/mTOR pathway, for instance EGFR, HER2, HER3, ALK, MET, PI3K, PDK1, AKT, mTOR and S6K.

A subject of the present invention is in particular the use of a product of formula (I) as defined above, for the preparation of a medicament for use in the prevention or treatment of lysosomal diseases such as glycogenosis type II or Pompe disease. Such medicaments for use in the treatment of lysosomal diseases can be used alone or in combination, for example, with other therapeutic agents.

A subject of the present invention is thus the products of formula (I) as defined above, for the prevention or treatment of lysosomal diseases such as glycogenosis type II or Pompe disease.

A subject of the present invention is thus the use of the products of formula (I) as defined above, for the preparation of a medicament for use in the prevention or treatment of lysosomal diseases such as glycogenosis type II or Pompe disease.

A subject of the present invention is thus the use as defined above, in which said products of formula (I) are alone or in combination.

A subject of the present invention is also the use of a product of formula (I) as defined above, for the preparation of a medicament for use in the treatment of parasitic diseases such as malaria, sleeping sickness, Chagas disease or leishmaniasis. Such medicaments for use in the treatment of parasitic infections can be used alone or in combination, for example, with other therapeutic agents.

A subject of the present invention is thus the products of formula (I) as defined above, for the treatment of parasitic diseases such as malaria, sleeping sickness, Chagas disease or leishmaniasis.

A subject of the present invention is thus the use of the products of formula (I) as defined above, for the preparation of a medicament for the treatment of parasitic diseases such as malaria, sleeping sickness, Chagas disease or leishmaniasis.

A subject of the present invention is also, as novel industrial products, the synthesis intermediates of formulae D, E, F and J as defined above and recalled hereinafter:

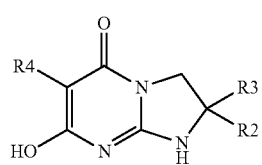

D

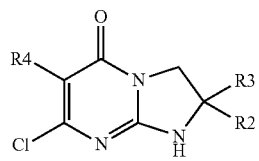

E

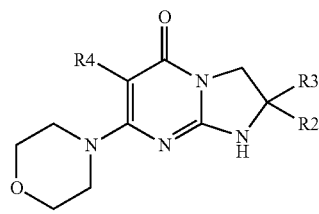

F

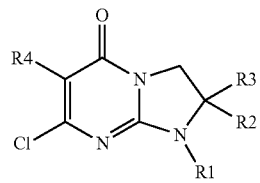

J in which R1, R2, R3 and R4 have the definitions indicated in either one of claims 1 and 2.

The following examples, which are products of formula (I), illustrate the invention without, however, limiting it.

Experimental Section

The nomenclature of the compounds of this present invention was carried out with the ACDLABS software, version 10.0.

The microwave oven used is a Biotage, Initiator™ 2.0, 400W max, 2450 MHz, instrument.

The $^1$H NMR spectra at 400 MHz and $^1$H spectra at 500 MHz were performed on a Bruker Avance DRX-400 or Bruker Avance DPX-500 spectrometer with the chemical shifts (δ in ppm) in the solvent dimethyl sulphoxide-$d_6$ (DMSO-$d_6$) referenced at 2.5 ppm at a temperature of 303K.

The mass spectra (MS) were obtained either by method A or by method B or by method E:

Method A:

Waters HPLC-SQD instrument; ionisation: positive and/or negative mode electrospray (ES+/−); chromatographic conditions: column: Acquity BEH C18 1.7 μm-2.1×50 mm; solvents: A: H$_2$O (0.1% formic acid) B: CH$_3$CN (0.1% formic acid); column temperature: 50° C.; flow rate: 1 ml/min; gradient (2 min): from 5% to 50% of B in 0.8 min; 1.2 min: 100% of B; 1.85 min: 100% of B; 1.95: 5% of B; retention time=Tr (min).

Method B:

Waters ZQ instrument; ionisation: positive and/or negative mode electrospray (ES+/−); chromatographic conditions: column: XBridge C$_{18}$ 2.5 μm-3×50 mm; solvents: A: H$_2$O (0.1% formic acid) B: CH$_3$CN (0.1% formic acid); column temperature: 70° C.; flow rate: 0.9 ml/min; gradient (7 min): from 5% to 100% of B in 5.3 min; 5.5 min: 100% of B; 6.3 min: 5% of B; retention time=Tr (min).

Method E:

Waters HPLC-SQD instrument; ionisation: positive and/or negative mode electrospray (ES+/−); chromatographic conditions: column: Ascentis express C18 2.7 μm-2.1×50 mm; solvents: A: H$_2$O (0.02% trifluoroacetic acid) B: CH$_3$CN (0.014% trifluoroacetic acid); column temperature: 55° C.; flow rate: 1 ml/min; gradient T0min 2% B, T1 min 98% B, T1.3 min 98% B, T1.33 min 2% B, T1.5 other injection; retention time=Tr (min).

The optical rotations (OR) were measured on a polarimeter model 341 from Perkin Elmer. Wavelength: α line of sodium (589 nanometres).

Purifications by preparative HPLC/MS:

Method C

SunFire C18 reverse phase column (Waters) 30×100, 5μ.

Gradient of acetonitrile (+0.07% TFA) in water (+0.07% TFA)

T0: 20% acetonitrile (+0.07% TFA)
T1: 20% acetonitrile (+0.07% TFA)
T11.5: 95% acetonitrile (+0.07% TFA)
T15: 95% acetonitrile (+0.07% TFA)
T15.5: 20% acetonitrile (+0.07% TFA)

Flow rate: 30 ml/min
Mass: 130_800 AMU=; ESP+ESP
Method D
SunFire C18 reverse phase column (Waters) 30×100, 5μ.
Gradient of acetonitrile (+0.07% TFA) in water (+0.07% TFA)
T0: 15% acetonitrile (+0.07% TFA)
T1: 15% acetonitrile (+0.07% TFA)
T11: 90% acetonitrile (+0.07% TFA)
T11.5: 95% acetonitrile (+0.07% TFA)
T14: 95% acetonitrile (+0.07% TFA)
T15: 10% acetonitrile (+0.07% TFA)
Flow rate: 30 ml/min
Mass: 130_800 AMU=; ESP+ESP

EXAMPLE 1

(S)-1-[2-(4-Methoxyphenyl)ethyl]-2-methyl-7-morpholin-4-yl-2-trifluoromethyl-2,3-dihydro-1H-imidazo[1,2-a]pyrimidin-5-one

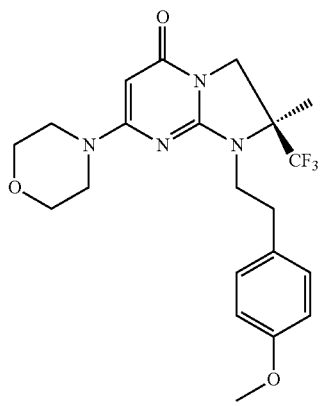 [SMILES: COc1ccc(CCN2c3nc(N4CCOCC4)cc(=O)n3C[C@@]2(C)C(F)(F)F)cc1]

Stage k: (S)-1-[2-(4-Methoxyphenyl)ethyl]-2-methyl-7-morpholin-4-yl-2-trifluoromethyl-2,3-dihydro-1H-imidazo[1,2-a]pyrimidin-5-one 20 mg of sodium hydride are added, at ambient temperature, under an argon atmosphere, to a solution of 60 mg of (S)-2-methyl-7-morpholin-4-yl-2-trifluoromethyl-2,3-dihydro-1H-imidazo[1,2-a]pyrimidin-5-one in 3 ml of anhydrous N,N-dimethylformamide. The reaction mixture obtained is then heated to 60° C. 0.04 ml of 4-methoxyphenethyl bromide is subsequently added. After heating for one hour and after verification by TLC (CH$_2$Cl$_2$/MeOH: 95/05), the reaction is partial. 10 mg of sodium hydride and 0.04 ml of 4-methoxyphenethyl bromide are then added and the heating is maintained at 60° C. After a further two hours of heating and after verification by TLC (CH$_2$Cl$_2$/MeOH: 95/05), the reaction is complete.

After cooling, 10 ml of cold water and 20 ml of ethyl acetate are added to the mixture obtained. The organic phase is then separated and then dried over magnesium sulphate, filtered, and concentrated under reduced pressure. The residue obtained is purified by silica chromatography (eluent: CH$_2$Cl$_2$/MeOH: 98/02) so as to give 54 mg of (S)-1-[2-(4-methoxyphenyl)ethyl]-2-methyl-7-morpholin-4-yl-2-trifluoromethyl-2,3-dihydro-1H-imidazo[1,2-a]pyrimidin-5-one, in the form of an off-white foam, the characteristics of which are the following:

$^1$H NMR spectrum
1.52 (s, 3 H); 2.79 (m, 1 H); 2.95 (m, 1 H); 3.30 to 3.60 (m, 6 H); 3.65 (t, J=4.9 Hz, 4 H); 3.72 (s, 3 H); 3.84 (d, J=12.6 Hz, 1 H); 4.11 (d, J=12.6 Hz, 1 H); 4.88 (s, 1 H); 6.87 (d, J=8.6 Hz, 2 H); 7.14 (d, J=8.6 Hz, 2 H).
Mass spectrometry: method B
Retention time Tr (min)=4.07
[M+H]+: m/z 439
Optical rotation: OR=+89; C=0.710 mg/0.5 ml DMSO.

Stage j: (S)-2-Methyl-7-morpholin-4-yl-2-trifluoromethyl-2,3-dihydro-1H-imidazo[1,2-a]pyrimidin-5-one

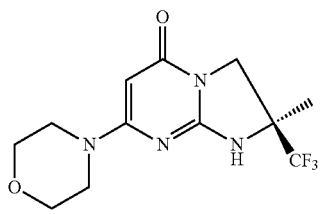 [SMILES: C[C@@]1(C(F)(F)F)Cn2c(nc(N3CCOCC3)cc2=O)N1]

A mixture of 2.2 g of (S)-7-chloro-2-methyl-2-trifluoromethyl-2,3-dihydro-1H-imidazo[1,2-a]pyrimidin-5-one in 60 ml of morpholine is heated to 120° C. After heating for one hour and after verification by LC/MS, the reaction is complete.

After cooling, the reaction mixture is concentrated under reduced pressure. 30 ml of cold water and 150 ml of ethyl acetate are added to the residue obtained. The organic phase is then separated, dried over magnesium sulphate, filtered, and then concentrated under reduced pressure so as to give 2.6 g of (S)-2-methyl-7-morpholin-4-yl-2-trifluoromethyl-2,3-dihydro-1H-imidazo[1,2-a]pyrimidin-5-one, the characteristics of which are the following:
Mass spectrometry: method B
Retention time Tr (min)=2.53
[M+H]+: m/z 305; [M−H]−: m/z 303
Optical rotation: OR=−9.0+/−0.6; C=1.996710 mg/0.5 ml DMSO.

Stage i: (S)-7-Chloro-2-methyl-2-trifluoromethyl-2,3-dihydro-1H-imidazo-[1,2-a]pyrimidin-5-one

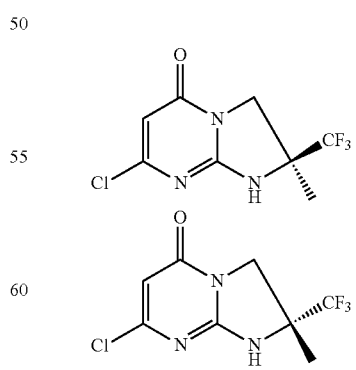

The two enantiomers of 7-chloro-2-methyl-2-trifluoromethyl-2,3-dihydro-1H-imidazo[1,2-a]pyrimidin-5-one (9.22 g) were separated by chiral chromatography:

Stationary phase: Chiralpak AD; mobile phase: EtOH (05%)/MeOH (05%)/heptane (90%).

The dextrorotary enantiomer is concentrated so as to obtain 4.56 g of (R)-7-chloro-2-methyl-2-trifluoromethyl-2,3-dihydro-1H-imidazo[1,2-a]pyrimidin-5-one.

The levorotatory enantiomer is concentrated so as to obtain 4.47 g of (S)-7-chloro-2-methyl-2-trifluoromethyl-2,3-dihydro-1H-imidazo[1,2-a]pyrimidin-5-one, in the form of a white powder, the characteristics of which are the following:

Optical rotation: OR=−70.9+/−1.1; C=2.623 mg/0.5 ml DMSO.

Mass spectrometry: method A

Retention time Tr (min)=0.51

[M+H]+: m/z 254; [M−H]−: m/z 252.

Stage h: (R,S)-7-Chloro-2-methyl-2-trifluoromethyl-2,3-dihydro-1H-imidazo[1,2-a]pyrimidin-5-one

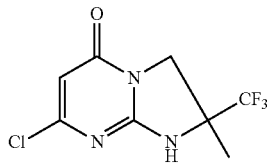 [SMILES: CC1(C(F)(F)F)Cn2c(nc(Cl)cc2=O)N1]

20 ml of phosphorus oxychloride are added, at ambient temperature and under an argon atmosphere, to a suspension of 20 g of (R,S)-7-hydroxy-2-methyl-2-trifluoromethyl-2,3-dihydro-1H-imidazo[1,2-a]pyrimidin-5-one in 400 ml of 1,2-dichloroethane. The reaction mixture is then heated to 65° C. After stirring for two hours and after verification of LC/MS, the reaction is complete.

After cooling, the pale yellow solid formed is filtered off so as to give 4.05 g of a first batch of the chlorinated product S1. The resulting filtrate is evaporated to dryness under reduced pressure and the residue obtained is taken up with 20 ml of cold water and 200 ml of ethyl acetate. 32% sodium hydroxide is added to the mixture obtained, until pH=5-6. The organic phase is then separated, dried over magnesium sulphate, filtered and then concentrated under reduced pressure so as to give a yellow foam. The latter is purified by silica chromatography (eluent: CH$_2$Cl$_2$/MeOH: 98/02) so as to give 12.24 g of a solid S2.

The two batches, S1 and S2, which are identical by TLC, are combined so as to give 16.29 g of (R,S)-7-chloro-2-methyl-2-trifluoromethyl-2,3-dihydro-1H-imidazo[1,2-a]pyrimidin-5-one, the characteristics of which are the following:

Mass spectrometry: method A

Retention time Tr (min)=0.51

[M+H]+: m/z 254; [M−H]−: m/z 252.

Stage g: (R,S)-7-Hydroxy-2-methyl-2-trifluoromethyl-2,3-dihydro-1H-imidazo[1,2-a]pyrimidin-5-one

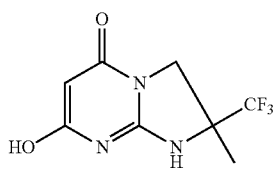 [SMILES: CC1(C(F)(F)F)Cn2c(nc(O)cc2=O)N1]

31.6 g of 4-methyl-4-trifluoromethylimidazolidin-2-ylidene amine hydrobromide and 13.7 g of sodium methoxide are added to a mixture of 20.4 g of diethyl malonate in 320 ml of methanol. The resulting mixture is brought to reflux for 18 hours.

After cooling, the reaction mixture is concentrated to dryness under reduced pressure. 100 ml of cold water are added to the residue obtained. 25% hydrochloric acid is added to the resulting thick suspension, until pH=5. The suspension obtained is stirred in an ice bath for two hours and then filtered through sintered glass. The insoluble material is rinsed with water (2 times 15 ml) and then dried, so as to give 30 g of (R,S)-7-hydroxy-2-methyl-2-trifluoromethyl-2,3-dihydro-1H-imidazo[1,2-a]pyrimidin-5-one, in the form of a white solid, the characteristics of which are the following:

Mass spectrometry: method B

Retention time Tr (min)=1.29

[M+H]+: m/z 236; [M−H]−: m/z 234.

Stage f: (R,S)-4-Methyl-4-trifluoromethylimidazolidin-2-ylidene amine hydrobromide

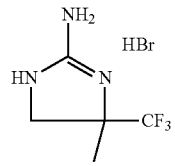

3.72 g of cyanogen bromide are added, while maintaining the temperature between 5 and 10° C., to a solution, cooled to 5° C., of 5 g of (R,S)-3,3,3-trifluoro-2-methylpropane-1,2-diamine in 30 ml of water. Once the addition is complete, the reaction mixture is left at 5° C. for 30 minutes. The ice bath is then removed and the reaction mixture is stirred at ambient temperature for 3 hours.

The reaction mixture is then concentrated under reduced pressure. The residue obtained is taken up twice with 200 ml of EtOH, and then twice with 200 ml of toluene, with evaporation to dryness each time. The resulting solid is triturated with ethyl ether and then filtered so as to give 7 g of (R,S)-4-methyl-4-trifluoromethylimidazolidin-2-ylidene amine hydrobromide, in the form of a white solid, the characteristics of which are the following:

Mass spectrometry: method A

[M+H]+: m/z=168.

Stage e:
(R,S)-3,3,3-Trifluoro-2-methylpropane-1,2-diamine

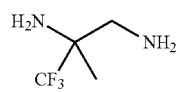

27 g of (R,S)-3,3,3-trifluoro-2-methylpropane-1,2-diamine hydrochloride, 15 ml of water and 400 ml of ethyl ether are introduced into a round-bottomed flask. 25 ml of 32% sodium hydroxide are added, dropwise, with magnetic stirring, to the mixture obtained, until pH=12. The aqueous phase is then separated by settling out and then extracted with 4 times 200 ml of ethyl ether.

The organic phases are combined, dried over magnesium sulphate, filtered and then concentrated under reduced pressure (300 mbar/bath temperature=25° C.) so as to give 21.9 g of (R,S)-3,3,3-trifluoro-2-methylpropane-1,2-diamine, in the form of a light yellow oil, the characteristics of which are the following:
Mass spectrometry: method A
[M+H]+: m/z=143.

Stage d:
(R,S)-3,3,3-Trifluoro-2-methylpropane-1,2-diamine dihydrochloride, 2HCl

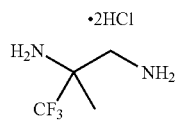

8 g of 20% palladium hydroxide, 58 g of (R,S)-N-benzyl-3,3,3-trifluoro-2-methylpropane-1,2-diamine in 200 ml of methanol and 183 ml of 3N hydrochloric acid are introduced into an autoclave. The resulting mixture is hydrogenated at a hydrogen pressure of 5 bar, at 22° C., for 48 hours.

The resulting mixture is then filtered and the filtrate is then concentrated under reduced pressure. The residue obtained is taken up twice with 300 ml of EtOH, then twice with 300 ml of toluene, with evaporation to dryness each time. 50 g of (R,S)-3,3,3-trifluoro-2-methylpropane-1,2-diamine dihydrochloride are thus obtained in the form of an off-white foam, the characteristics of which are the following:
Mass spectrometry: method A
[M+H]+: m/z=143.

Stage c: (R,S)-N-Benzyl-3,3,3-trifluoro-2-methylpropane-1,2-diamine

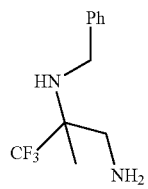

In a three-necked flask under argon, 15.5 g of lithium aluminium hydride are added, in small portions, to a solution of 23 g of (R,S)-N-benzylamino-3,3,3-trifluoro-2-methylpropionitrile in 1000 ml of anhydrous ethyl ether cooled to 4° C. A substantial release of gas with an increase in the temperature to 8° C. is observed.

Once the addition is complete, the temperature is allowed to rise to ambient temperature and the mixture is left to stirring at ambient temperature for 18 h. The resulting reaction mixture is cooled to 4° C., before adding 20 ml of water, dropwise and very slowly. A substantial release of gas with an increase in the temperature up to 12° C. is observed.

Still at 4° C., 20 ml of 15% potassium hydroxide are added, dropwise and very slowly, to the mixture obtained, followed, still dropwise and very slowly, by 40 ml of water.

The resulting white precipitate is filtered off and the filtrate is dried over magnesium sulphate and then concentrated under reduced pressure to give 22.5 g of (R,S)-N-benzyl-3,3,3-trifluoro-2-methylpropane-1,2-diamine, in the form of a colourless oil, the characteristics of which are the following:
Mass spectrometry: method A
[M+H]+: m/z=233.

Stage b: 2-Benzylamino-3,3,3-trifluoro-2-methylpropionitrile

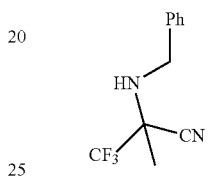

In a three-necked flask and under an argon atmosphere, 59.17 g of trimethylsilyl cyanide are added, dropwise, to a solution of 80 g of (R,S)-N-benzyl-[2,2,2-trifluoro-1-methyleth-(E)-ylidene]amine in 800 ml of dichloromethane, cooled to −70° C., followed, dropwise, by 84.65 g of boron trifluoroetherate. The temperature increases to −63° C. and the solution turns orange. After addition, the reaction mixture is stirred at −63° C. for 30 min.

The dry-ice bath is then removed so as to allow the temperature to rise again to ambient temperature. The reaction mixture is then left to stir at ambient temperature overnight.

A saturated solution of sodium bicarbonate is then added to the resulting mixture, to pH=8. The organic phase is then separated and then dried over magnesium sulphate, filtered, and concentrated under reduced pressure. The residue obtained is purified by filtration through silica (eluent: dichloromethane/cyclohexane: 25/75) so as to give 48 g of (R,S)-2-benzylamino-3,3,3-trifluoro-2-methylpropionitrile, in the form of a colourless oil, the characteristics of which are the following:
Mass spectrometry:
The spectra were performed by electron impact on a Waters GCTOF instrument (direct introduction without LC).
EI: [M]+: m/z 228; m/z 91 (base peak)

Stage a: Benzyl-[2,2,2-trifluoro-1-methyleth-(E)-ylidene]amine

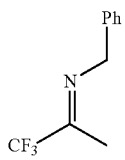

In a three-necked flask, 100 g of benzylamine are added, dropwise, to a solution of 157 g of trifluoroacetone in 600 ml of toluene, cooled to 5° C. The temperature rises to 25° C.

9.4 g of pyridinium para-toluenesulphonate are then added in a single step. The resulting reaction mixture is stirred at ambient temperature for 30 minutes. A condenser surmounted by a Dean-Stark apparatus is then installed and the reaction mixture is refluxed for 4 hours, during which time 25 ml of water are recovered.

After cooling, the solid form is filtered off and the filtrate is concentrated under reduced pressure so as to give 150 g of [2,2,2-trifluoro-1-methyleth-(E)ylidene]amine, in the form of a colourless liquid, the characteristics of which are the following:

Mass spectrometry:

The spectrum were performed by electron impact on a Waters GCTOF instrument (direct introduction without LC).

EI: [M]+: m/z 201; m/z 91 (base peak).

Alternatively, the (S)-7-chloro-2-methyl-2-trifluoromethyl-2,3-dihydro-1H-imidazo[1,2-a]pyrimidin-5-one can be prepared in the following way:

Stage h': (S)-7-Chloro-2-methyl-2-trifluoromethyl-2,3-dihydro-1H-imidazo[1,2-a]pyrimidin-5-one

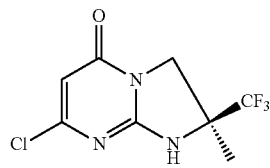 [SMILES: C[C@@]1(C(F)(F)F)Cn2c(nc(Cl)cc2=O)N1]

11 ml of phosphorus oxychloride are added, at ambient temperature and under an argon atmosphere, to a suspension of 5.6 g of (S)-7-hydroxy-2-methyl-2-trifluoromethyl-2,3-dihydro-1H-imidazo[1,2-a]pyrimidin-5-one in 100 ml of 1,2-dichloroethane. The resulting mixture is then heated to 70° C. After stirring for two hours and after verification of LC/MS, the reaction is complete.

After cooling, the reaction mixture is evaporated to dryness under reduced pressure. The residue obtained is taken up with 5 ml of cold water and 200 ml of ethyl acetate. 32% sodium hydroxide is added to the mixture obtained, until pH=6. The organic phase is then separated and then dried over magnesium sulphate, filtered and concentrated under reduced pressure so as to give 6 g of (S)-7-chloro-2-methyl-2-trifluoromethyl-2,3-dihydro-1H-imidazo[1,2-a]pyrimidin-5-one, the characteristics of which are the following:

Mass spectrometry:
Method A
Retention time Tr (min)=0.51
[M+H]+: m/z 254; [M−H]−: m/z 252
Optical rotation: OR=−64.8+/−1.1; C=2.2 ring/0.5 ml DMSO.

Stage g': (S)-7-Hydroxy-2-methyl-2-trifluoromethyl-2,3-dihydro-1H-imidazo[1,2-a]pyrimidin-5-one

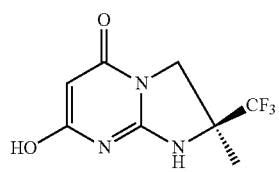 [SMILES: C[C@@]1(C(F)(F)F)Cn2c(nc(O)cc2=O)N1]

8.4 g of (S)-4-methyl-4-trifluoromethylimidazolidin-2-ylidene amine hydrobromide and 2.16 g of sodium methoxide are added to a mixture of 5.4 g of diethyl malonate in 50 ml of methanol.

The resulting mixture is brought to reflux for 18 hours. After cooling, the mixture obtained is concentrated to dryness under reduced pressure. 20 ml of cold water are added to the residue obtained, so as to obtain a thick suspension to which 25% hydrochloric acid is added until pH=5.

The resulting suspension is stirred in an ice bath for two hours and then filtered through sintered glass. The insoluble material obtained is rinsed with water (twice 4 ml) and then dried so as to give 5.6 g of (S)-7-hydroxy-2-methyl-2-trifluoromethyl-2,3-dihydro-1H-imidazo[1,2-a]pyrimidin-5-one, in the form of a white solid, the characteristics of which are the following:

Mass spectrometry: method A
Retention time Tr (min)=0.32
[M+H]+: m/z 236; [M−H]−: m/z 234
Optical rotation: OR=−5.6+/−0.6; C=1.789 mg/0.5 ml MeOH.

Stage f': (S)-4-Methyl-4-trifluoromethylimidazolidin-2-ylidene amine hydrobromide

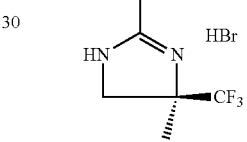

1.7 g of cyanogen bromide are added, in small amounts, while maintaining the temperature between 5° C. and 10° C., to a solution, cooled to 5° C., of 2.3 g of (S)-3,3,3-trifluoro-2-methylpropane-1,2-diamine in 10 ml of water. Once the addition is complete, the reaction mixture is left at 5° C. for 30 minutes. The ice bath is then removed and the mixture obtained is stirred at ambient temperature for 3 hours.

The resulting mixture is then concentrated under reduced pressure. The residue obtained is taken up twice with 100 ml of ethanol and then twice with 100 ml of toluene, with evaporation to dryness each time. The solid obtained is triturated with ethyl ether and then filtered so as to give 4.5 g of (S)-4-methyl-4-trifluoromethylimidazolidin-2-ylidene amine hydrobromide, in the form of a white solid, the characteristics of which are the following:

Mass spectrometry: method A
Retention time Tr (min)=0.14
[M+H]+: m/z 168
Optical rotation: OR=−5.2+/−0.3; C=4.909 mg/0.5 ml DMSO.

Stage e':
(S)-3,3,3-Trifluoro-2-methylpropane-1,2-diamine

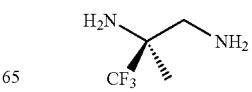

4.8 g of (S)-3,3,3-trifluoro-2-methylpropane-1,2-diamine hydrochloride, 2.5 ml of water and 100 ml of ethyl ether are introduced into a round-bottomed flask. 4.5 ml of 32% sodium hydroxide are added, dropwise, to the resulting mixture, until pH=12. The aqueous phase is subsequently separated by settling out and then extracted with 4 times 200 ml of ethyl ether.

The organic phases are combined, dried over magnesium sulphate, filtered, and then concentrated under reduced pressure (300 mbar/bath temperature=25° C.) so as to give 2.3 g of 3,3,3-trifluoro-2-methylpropane-1,2-diamine, in the form of a light yellow oil, the characteristics of which are the following:

Mass spectrometry: method B

Retention time Tr (min)=0.34

[M+H]+: m/z 143; base peak: m/z 126

Optical rotation: OR=−4.3+/−0.6; C=1.778 mg/0.5 ml DMSO.

Stage d':
(S)-3,3,3-Trifluoro-2-methylpropane-1,2-diamine dihydrochloride

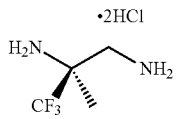

In an autoclave, a mixture of 7 g of (R)-2-(S)-1-aminomethyl-2,2,2-trifluoro-1-methylethylamino)-2-phenylethanol in 40.5 ml of methanol, 23.5 ml of 3N hydrochloric acid and 0.94 g of Pd(OH)₂/C (20% w/w) is hydrogenated at 22° C., under a hydrogen pressure of 5 bar and for 18 hours. The mixture obtained is subsequently filtered and the filtrate is evaporated to dryness. The oil obtained is taken up with a 3N solution of hydrochloric acid (50 ml). The mixture obtained is extracted with diethyl ether (3×50 ml). The aqueous phase is subsequently evaporated to dryness, taken up with methanol, and then again evaporated to dryness. The yellowish solid obtained is dried under vacuum so as to give 5.54 g (79%) of (S)-3,3,3-trifluoro-2-methylpropane-1,2-diamine dihydrochloride, in the form of an off-white solid, the characteristics of which are the following:

¹H NMR spectrum (400 MHz, D2O): 1.55 (s, 3 H), 3.40 (d, J=14.6 Hz, 1 H), 3.51 (d, J=14.6 Hz, 1 H).

¹⁹F NMR (400 MHz, D2O): −81.08 (not calibrated with C6F6)

[□]D: +4.65 (C 2.2, CH₃OH).

Stage c': (R)-2-((S)-1-Aminomethyl-2,2,2-trifluoro-1-methylethylamino)-2-phenylethanol

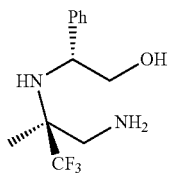

In a three-necked flask under argon, 1.6 g of lithium aluminium hydride are added, in small portions, to a solution, cooled to 4° C., of 2.5 g of (S)-3,3,3-trifluoro-2-((R)-2-hydroxy-1-phenylethylamino)-2-methylpropionitrile in 250 ml of anhydrous ethyl ether. A substantial release of gas with an increase in the temperature to 8° C. is observed.

Once the addition is complete, the temperature is allowed to rise back up to ambient temperature and then the reaction mixture is left stirring for 18 h. The mixture obtained is cooled to 4° C. before the addition, dropwise and very slowly, of 2 ml of water. A substantial release of gas with an increase in the temperature to 12° C. is observed.

2 ml of 15% potassium hydroxide are added, dropwise and very slowly, to the resulting mixture maintained at 4° C., followed, still dropwise and very slowly, by 4 ml of water.

The white precipitate formed is filtered off and the filtrate obtained is dried over magnesium sulphate and then concentrated under reduced pressure so as to give 2.2 g of (R)-2-((S)-1-aminomethyl-2,2,2-trifluoro-1-methylethylamino)-2-phenylethanol, the characteristics of which are the following:

Mass spectrometry: method A

Retention time Tr (min)=0.43

[M+H]+: m/z 263

Optical rotation: OR=−51.2+/−1.3; C=1.576 mg/0.5 ml DMSO.

Stage b': (S)-3,3,3-Trifluoro-2-((R)-2-hydroxy-1-phenylethylamino)-2-methylpropionitrile

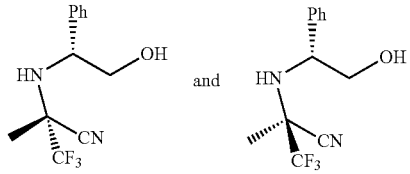 [SMILES: C[C@](C#N)(N[C@@H](CO)c1ccccc1)C(F)(F)F ; C[C@@](C#N)(N[C@@H](CO)c1ccccc1)C(F)(F)F]

In a three-necked flask under argon, 3.4 g of trimethylsilyl cyanide are added, dropwise, to a solution, cooled to 0° C., of 5.3 g of (R)-2-methyl-4-phenyl-2-trifluoromethyloxazolidine in 100 ml of dichloromethane, followed, dropwise, by 4.9 g of boron trifluoroetherate. The cold bath is subsequently removed so as to allow the temperature to rise back up to ambient temperature. The resulting mixture is left stirring at ambient temperature for 18 hours before the addition of a saturated solution of sodium bicarbonate until pH=8.

The organic phase is separated and then dried over magnesium sulphate, filtered and concentrated under reduced pressure.

The residue obtained is purified by silica chromatography (eluent: cyclohexane/AcOEt:80/20) so as to give 3 g of (R)-3,3,3-trifluoro-2-((R)-2-hydroxy-1-phenylethylamino)-2-methylpropionitrile, in the form of a colourless oil, and 2.5 g of (S)-3,3,3-trifluoro-2-((R)-2-hydroxy-1-phenylethylamino)-2-methylpropionitrile, in the form of a white solid, the characteristics of which are:

Mass spectrometry: method A

Retention time Tr (min)=0.86

[M+H]+: m/z 259; [M−H+HCO2H]−: m/z 303

Optical rotation: OR=−89.0+/−1.4; C=2.440 mg/0.5 ml CHCl₃, and

OR=−77.6+/−1.4; C=1.818 mg/0.5 ml DMSO.

Stage a': (R,S)-2-Methyl-4-(R)-phenyl-2-trifluoromethyloxazolidine

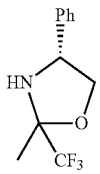

In a three-necked flask surmounted by a Dean-Stark apparatus, 4.8 g of (R)-phenylglycinol and then, in a single step, 0.8 g of pyridinium para-toluenesulphonate are added to a solution of 5 g of trifluoroacetone in 180 ml of toluene. The mixture obtained is subsequently refluxed for 18 hours, during which time 0.3 ml of water is recovered.

After cooling, the reaction mixture is concentrated under reduced pressure. The residue obtained is purified by filtration through silica (eluent: dichloromethane) so as to give 5.3 g of (R,S)-2-methyl-4-(R)-phenyl-2-trifluoromethyloxazolidine, in the form of a colourless liquid, the characteristics of which are the following:

Mass spectrometry: method A
Retention time Tr (min)=0.96
[M+H]+: m/z 232
Optical rotation: OR=−23.4+/−0.8; C=1.794 mg/0.5 ml CH₃OH.

EXAMPLE 2

(R,S)-1-[2-(4-methoxyphenyl)ethyl]-2-methyl-7-(morpholin-4-yl)-2-(trifluoromethyl)-2,3-dihydroimidazo[1,2-a]pyrimidin-5(1H)-one

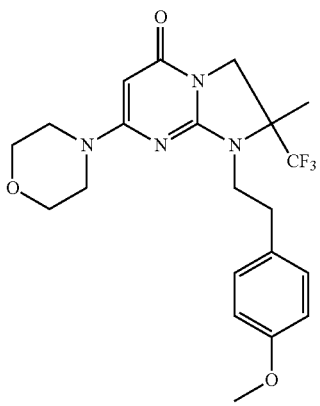 [SMILES: COc1ccc(CCN2c3nc(N4CCOCC4)cc(=O)n3CC2(C)C(F)(F)F)cc1]

The product is prepared according to the procedure described in Example 1, using 120 mg of (R,S)-2-methyl-7-morpholin-4-yl-2-trifluoromethyl-2,3-dihydro-1H-imidazo[1,2-a]pyrimidin-5-one (prepared according to the protocol of Example 1j but using the (R,S)-7-chloro-2-methyl-2-trifluoromethyl-2,3-dihydro-1H-imidazo[1,2-a]pyrimidin-5-one described in Example 1 h) and 420 mg of 4-methoxyphenethyl bromide. After purification by silica chromatography (eluent: gradient of 0% to 20% of the eluent CH₂Cl₂/MeOH/NH₄OH 28% 38/17/2 in dichloromethane), 80 mg of (R,S)-1-[2-(4-methoxyphenyl)ethyl]-2,6-dimethyl-7-morpholin-4-yl-2-trifluoromethyl-2,3-dihydro-1H-imidazo[1,2-a]pyrimidin-5-one are obtained, the characteristics of which are the following:

¹H NMR spectrum:
1.52 (broad s, 3 H); 2.73 to 2.84 (m, 1 H); 2.90 to 3.01 (m, 1 H); 3.36 to 3.59 (m, 6 H); 3.61 to 3.68 (m, 4 H); 3.72 (s, 3 H); 3.84 (broad d, J=12.5 Hz, 1 H); 4.11 (d, J=12.5 Hz, 1 H); 4.88 (s, 1 H); 6.87 (d, J=8.6 Hz, 2 H); 7.14 (d, J=8.6 Hz, 2 H).
Mass spectrometry: method A
Retention time Tr (min)=0.96
[M+H]+: m/z 439

EXAMPLE 3

(S)-1-Benzyl-2-methyl-7-morpholin-4-yl-2-trifluoromethyl-2,3-dihydro-1H-imidazo[1,2-a]pyrimidin-5-one

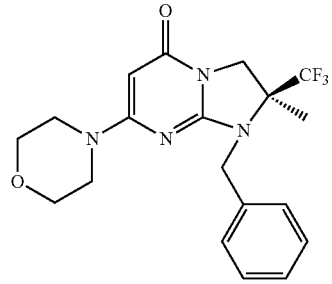 [SMILES: C[C@@]1(C(F)(F)F)Cn2c(nc(N3CCOCC3)cc2=O)N1Cc1ccccc1]

The product is prepared according to the procedure described in Example 1, using 100 mg of (S)-2-methyl-7-morpholin-4-yl-2-trifluoromethyl-2,3-dihydro-1H-imidazo[1,2-a]pyrimidin-5-one (Example 1j) and 281 mg of benzyl bromide, replacing the sodium hydride with caesium carbonate and adding 10 mg of benzyltriethylammonim chloride (BTEAC). After purification by silica column chromatography (eluent: dichloromethane/methanol 98/02), 70 mg of (S)-1-benzyl-2-methyl-7-morpholin-4-yl-2-trifluoromethyl-2,3-dihydro-1H-imidazo[1,2-a]pyrimidin-5-one are obtained, the characteristics of which are the following:

¹H NMR spectrum:
1.60 (s, 3 H); 3.34 (m partially masked, 4 H); 3.54 (m, 4 H); 3.97 (d, J=12.5 Hz, 1 H); 4.16 (d, J=12.5 Hz, 1 H); 4.57 (d, J=16.4 Hz, 1 H); 4.77 (d, J=16.4 Hz, 1 H); 4.89 (s, 1 H); 7.20 to 7.45 (m, 5 H).
Mass spectrometry: method B
Retention time Tr (min)=3.89
[M+H]+: m/z 395
Optical rotation: OR=−20.9+/−0.8; C=1.829 mg/0.5 ml DMSO.

EXAMPLE 4

(S)-2-Methyl-7-morpholin-4-yl-1-phenethyl-2-trifluoromethyl-2,3-dihydro-1H-imidazo[1,2-a]pyrimidin-5-one

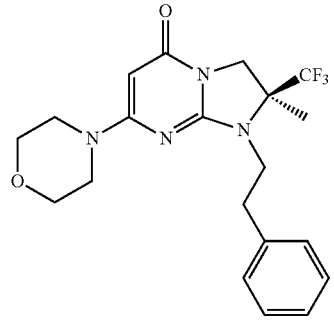 [SMILES: C[C@@]1(C(F)(F)F)Cn2c(nc(N3CCOCC3)cc2=O)N1CCc1ccccc1]

The product is prepared according to the procedure described in Example 1, using 100 mg of (S)-2-methyl-7-morpholin-4-yl-2-trifluoromethyl-2,3-dihydro-1H-imidazo[1,2-a]pyrimidin-5-one (Example 1j) and 304 mg of (2-bromoethyl)benzene, replacing the sodium hydride with caesium carbonate and adding 10 mg of benzyltriethylammonium chloride (BTEAC). After purification by silica column chromatography (eluent: dichloromethane/methanol 98/02), 120 mg of (S)-2-methyl-7-morpholin-4-yl-1-phenethyl-2-trifluoromethyl-2,3-dihydro-1H-imidazo[1,2-a]pyrimidin-5-one are obtained, the characteristics of which are the following:

¹H NMR spectrum (400 MHz, δ in ppm, DMSO-d6): 1.52 (s, 3 H); 2.79 to 2.91 (m, 1 H); 2.97 to 3.08 (m, 1 H); 3.40 to 3.51 (m, 5 H); 3.54 to 3.68 (m, 1 H); 3.64 (t, J=4.8 Hz, 4 H); 3.84 (d, J=12.5 Hz, 1 H); 4.11 (d, J=12.5 Hz, 1 H); 4.88 (s, 1 H); 7.20 to 7.26 (m, 3 H); 7.27 to 7.37 (m, 2 H).

Mass spectrometry: method B

Retention time Tr (min)=4.14

[M+H]+: m/z 409

Optical rotation: OR=−34.8+/−0.8; C=2.558 mg/0.5 ml DMSO.

EXAMPLE 5

(S)-2-Methyl-7-morpholin-4-yl-1-(3-phenylpropyl)-2-trifluoromethyl-2,3-dihydro-1H-imidazo[1,2-a]pyrimidin-5-one

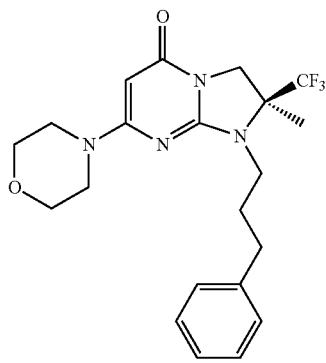 [SMILES: C[C@@]1(C(F)(F)F)Cn2c(nc(N3CCOCC3)cc2=O)N1CCCc1ccccc1]

The product is prepared according to the procedure described in Example 1, using 100 mg of (S)-2-methyl-7-morpholin-4-yl-2-trifluoromethyl-2,3-dihydro-1H-imidazo[1,2-a]pyrimidin-5-one (Example 1j) and 131 mg of 1-bromo-3-phenylpropane, replacing the sodium hydride with caesium carbonate. After purification by silica column chromatography (eluent: dichloromethane/methanol 97/03), 100 mg of (S)-2-methyl-7-morpholin-4-yl-1-(3-phenylpropyl)-2-trifluoromethyl-2,3-dihydro-1H-imidazo[1,2-a]pyrimidin-5-one are obtained, the characteristics of which are the following:

¹H NMR spectrum:

1.61 (s, 3 H); 1.83 to 2.02 (m, 2 H); 2.62 (t, J=7.3 Hz, 2 H); 3.26 to 3.42 (m partially masked, 6 H); 3.56 to 3.62 (m, 4 H); 3.86 (d, J=12.5 Hz, 1 H); 4.08 (d, J=12.5 Hz, 1 H); 4.82 (s, 1 H); 7.14 to 7.23 (m, 3 H); 7.24 to 7.33 (m, 2 H).

Mass spectrometry: method B
Retention time Tr (min)=4.27
[M+H]+: m/z 423
Optical rotation: OR=−1.5+/−0.4; C=2.576 mg/0.5 ml DMSO.

EXAMPLE 6

(S)-2-Methyl-7-morpholin-4-yl-1-(2-phenoxyethyl)-2-trifluoromethyl-2,3-dihydro-1H-imidazo[1,2-a]pyrimidin-5-one

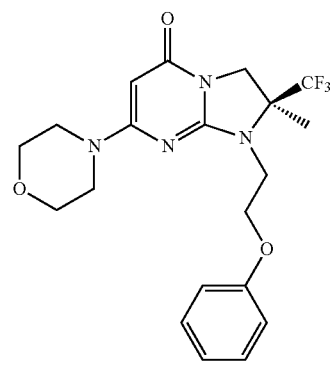 [SMILES: C[C@@]1(C(F)(F)F)Cn2c(nc(N3CCOCC3)cc2=O)N1CCOc1ccccc1]

The product is prepared according to the procedure described in Example 1, using 100 mg of (S)-2-methyl-7-morpholin-4-yl-2-trifluoromethyl-2,3-dihydro-1H-imidazo[1,2-a]pyrimidin-5-one (Example 1j) and 143 mg of (2-bromoethyl)phenyl ether, replacing the sodium hydride with caesium carbonate. After purification by silica column chromatography (eluent: dichloromethane/methanol 97/03), 124 mg of (S)-2-methyl-7-morpholin-4-yl-1-(2-phenoxyethyl)-2-trifluoromethyl-2,3-dihydro-1H-imidazo[1,2-a]pyrimidin-5-one are obtained, the characteristics of which are the following:

¹H NMR spectrum:
1.69 (s, 3 H); 3.35 to 3.44 (m, 4 H); 3.59 (t, J=4.7 Hz, 4 H); 3.63 to 3.73 (m, 1 H); 3.74 to 3.86 (m, 1 H); 3.92 (d, J=12.5 Hz, 1 H); 4.10 to 4.30 (m, 3 H); 4.88 (s, 1 H); 6.83 to 7.00 (m, 3 H); 7.24 to 7.32 (m, 2 H).

Mass spectrometry: method A
Retention time Tr (min)=0.95
[M+H]+: m/z 425.

EXAMPLE 7

(S)-2-Methyl-7-morpholin-4-yl-1-(2-phenylsulfanylethyl)-2-trifluoromethyl-2,3-dihydro-1H-imidazo[1,2-a]pyrimidin-5-one

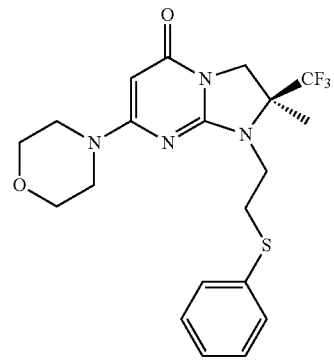 [SMILES: C[C@@]1(C(F)(F)F)Cn2c(nc(N3CCOCC3)cc2=O)N1CCSc1ccccc1]

The product is prepared according to the procedure described in Example 1, using 100 mg of (S)-2-methyl-7-morpholin-4-yl-2-trifluoromethyl-2,3-dihydro-1H-imidazo[1,2-a]pyrimidin-5-one (Example 1j) and 143 mg of 2-bromoethylphenyl sulphide, replacing the sodium hydride with caesium carbonate. After purification by silica column chromatography (eluent: dichloromethane/methanol 97/03), 96 mg of (S)-2-methyl-7-morpholin-4-yl-1-(2-phenylsulfanyl-ethyl)-2-trifluoromethyl-2,3-dihydro-1H-imidazo[1,2-a]pyrimidin-5-one are obtained, the characteristics of which are the following:

¹H NMR spectrum:
1.62 (s, 3 H); 3.05 to 3.17 (m, 1 H); 3.20 to 3.34 (m, 5 H); 3.40 to 3.51 (m, 1 H); 3.55 to 3.64 (s, 5 H); 3.83 (d, J=12.5 Hz, 1 H); 4.10 (d, J=12.5 Hz, 1 H); 4.86 (s, 1 H); 7.26 (t, J=7.5 Hz, 1 H); 7.34 (t, J=7.5 Hz, 2 H); 7.44 (d, J=7.5 Hz, 2 H).

Mass spectrometry: method A
Retention time Tr (min)=1.01
[M+H]+: m/z 441.

EXAMPLE 8

(S)-2-Methyl-7-morpholin-4-yl-1-((R)-2-phenylpropyl)-2-trifluoromethyl-2,3-dihydro-1H-imidazo[1,2-a]pyrimidin-5-one

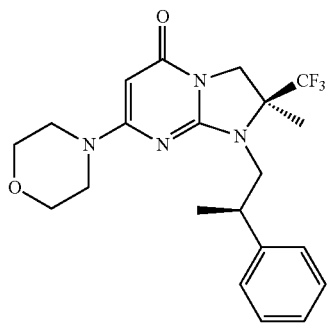 [SMILES: C[C@@H](CN1c2nc(N3CCOCC3)cc(=O)n2C[C@@]1(C)C(F)(F)F)c1ccccc1]

The product is prepared according to the procedure described in Example 1, using 100 mg of (S)-2-methyl-7-morpholin-4-yl-2-trifluoromethyl-2,3-dihydro-1H-imidazo[1,2-a]pyrimidin-5-one (Example 1j) and 143 mg of 1-bromo-2-phenylpropane, replacing the sodium hydride with caesium carbonate. After purification by silica column chromatography (eluent: dichloromethane/methanol 97/03), 100 mg of (2S)-2-methyl-7-morpholin-4-yl-1-((R and S)-2-phenylpropyl)-2-trifluoromethyl-2,3-dihydro-1H-imidazo[1,2-a]pyrimidin-5-one are obtained.

The two diastereoisomers of (2S)-2-methyl-7-morpholin-4-yl-1-(2-phenylpropyl)-2-trifluoromethyl-2,3-dihydro-1H-imidazo[1,2-a]pyrimidin-5-one were separated by chiral chromatography:

Stationary phase: Chiralpak AD, mobile phase: EtOH (04%)/MeOH (01%)/heptane (95%).

The first diastereoisomer is concentrated so as to give 17 mg of (S)-2-methyl-7-morpholin-4-yl-1-((R)-2-phenylpropyl)-2-trifluoromethyl-2,3-dihydro-1H-imidazo[1,2-a]pyrimidin-5-one, the characteristics of which are the following:

¹H NMR spectrum:
1.25 (d, J=6.4 Hz, 3 H); 1.68 (s, 3 H); 3.32 to 3.51 (m, 7 H); 3.60 to 3.67 (m, 4 H); 3.91 (d, J=12.4 Hz, 1 H); 4.12 (d, J=12.4 Hz, 1 H); 4.87 (s, 1 H); 7.20 to 7.24 (m, 1 H); 7.25 to 7.36 (m, 4 H).

Mass spectrometry: method A
Retention time Tr (min)=1.01
[M+H]+: m/z 423.

EXAMPLE 9

(S)-2-Methyl-7-morpholin-4-yl-1-((S)-2-phenylpropyl)-2-trifluoromethyl-2,3-dihydro-1H-imidazo[1,2-a]pyrimidin-5-one

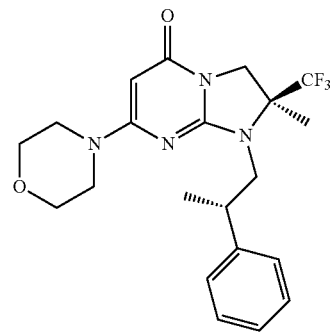 [SMILES: C[C@H](CN1c2nc(N3CCOCC3)cc(=O)n2C[C@@]1(C)C(F)(F)F)c1ccccc1]

The second diastereoisomer obtained in Example 8 is concentrated so as to give 19 mg of (S)-2-methyl-7-morpholin-4-yl-1-((S)-2-phenylpropyl)-2-trifluoromethyl-2,3-dihydro-1H-imidazo[1,2-a]pyrimidin-5-one, the characteristics of which are the following:

¹H NMR spectrum:
1.08 (s, 3 H); 1.26 (d, J=6.8 Hz, 3 H); 3.35 to 3.70 (m, 12 H); 4.05 (d, J=12.7 Hz, 1 H); 4.88 (s, 1 H); 7.18 to 7.25 (m, 3 H); 7.27 to 7.34 (m, 2 H).

Mass spectrometry: method A
Retention time Tr (min)=1.01
[M+H]+: m/z 423.

EXAMPLE 10

(S)-1-(S)-2-Hydroxy-2-phenylethyl)-2-methyl-7-morpholin-4-yl-2-trifluoromethyl-2,3-dihydro-1H-imidazo[1,2-a]pyrimidin-5-one

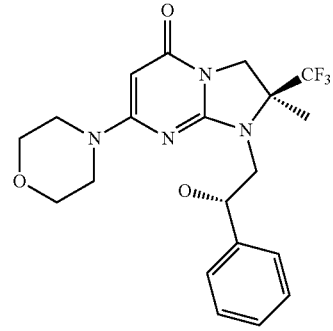 [SMILES: C[C@@]1(C(F)(F)F)Cn2c(nc(N3CCOCC3)cc2=O)N1C[C@@H](O)c1ccccc1]

The product is prepared according to the procedure described in Example 1, using 200 mg of (R,S)-2-methyl-7-morpholin-4-yl-2-trifluoromethyl-2,3-dihydro-1H-imidazo[1,2-a]pyrimidin-5-one (prepared according to the protocol in Example 1j but using the (R,S)-7-chloro-2-methyl-2-trifluoromethyl-2,3-dihydro-1H-imidazo[1,2-a]pyrimidin-5- one described in Example 1 h) and 0.4 ml of (S)-2-chloro-1-phenylethanol, replacing the sodium hydride with caesium carbonate and adding 10 mg of benzyltriethylammonium chloride (BTEAC). After purification by preparative LC/MS and then returning to the base by passing through a silica column (eluent: dichloromethane/methanol/triethylamine 98/02/0.5), 100 mg of (S)-1-((S)-2-hydroxy-2-phenylethyl)-2-methyl-7-morpholin-4-yl-2-trifluoromethyl-2,3-dihydro-1H-imidazo[1,2-a]pyrimidin-5-one are obtained, the characteristics of which are the following:

¹H NMR spectrum:

1.71 (s, 3 H); 3.17 (dd, J=9.7 and 14.4 Hz, 1 H); 3.40 to 3.52 (m, 4 H); 3.56 (dd, J=2.9 and 14.4 Hz, 1 H); 3.65 (t, J=4.9 Hz, 4 H); 3.85 (d, J=12.5 Hz, 1 H); 4.18 (d, J=12.5 Hz, 1 H); 4.90 (s, 1 H); 5.06 to 5.15 (m, 1 H); 5.60 (d, J=4.4 Hz, 1 H); 7.23 to 7.43 (m, 5 H).

Mass spectrometry: method A

Retention time Tr (min)=0.85

[M+H]+: m/z 425; [MHCO₂ H–H]–: m/z 469

Optical rotation: OR=–45.1+/–1.0; C=2.151 mg/0.5 ml DMSO.

The above purifications also produce 36 mg of the second diastereoisomer, (R)-1-((S)-2-hydroxy-2-phenylethyl)-2-methyl-7-morpholin-4-yl-2-trifluoromethyl-2,3-dihydro-1H-imidazo[1,2-a]pyrimidin-5-one.

EXAMPLE 11

(S)-1-(((R)-2-Hydroxy-2-phenylethyl)-2-methyl-7-morpholin-4-yl-2-trifluoromethyl-2,3-dihydro-1H-imidazo[1,2-a]pyrimidin-5-one

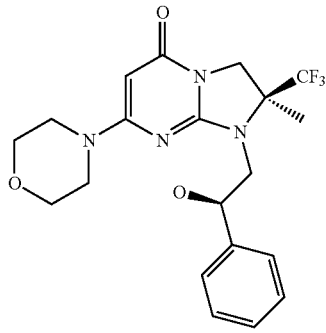 [SMILES: C[C@@]1(C(F)(F)F)Cn2c(nc(N3CCOCC3)cc2=O)N1C[C@H](O)c1ccccc1]

The product is prepared according to the procedure described in Example 1, using 275 mg of (R,S)-2-methyl-7-morpholin-4-yl-2-trifluoromethyl-2,3-dihydro-1H-imidazo[1,2-a]pyrimidin-5-one (prepared according to the protocol of Example 1j but using the (R,S)-7-chloro-2-methyl-2-trifluoromethyl-2,3-dihydro-1H-imidazo[1,2-a]pyrimidin-5-one described in Example 1 h) and 0.155 ml of (R)-2-chloro-1-phenylethanol. After purification by silica gel chromatography (eluent: dichloromethane/methanol 97/03) and then purification by preparative LC/MS and returning to the base by passing through a silica column (eluent: dichloromethane/methanol/triethylamine 98/02/0.5), 40 mg of (S)-1-((R)-2-hydroxy-2-phenylethyl)-2-methyl-7-morpholin-4-yl-2-trifluoromethyl-2,3-dihydro-1H-imidazo[1,2-a]pyrimidin-5-one are obtained, the characteristics of which are the following:

¹H NMR spectrum:

1.10 (s, 3 H); 3.25 (dd, J=6.8 and 13.5 Hz, 1 H); 3.38 to 3.49 (m, 4 H); 3.64 (m, 6 H); 4.07 (d, J=12.5 Hz, 1 H); 4.88 (s, 1 H); 5.05 to 5.13 (m, 1 H); 5.55 (d, =4.2 Hz, 1 H); 7.20 to 7.45 (m, 5 H).

Mass spectrometry: method B

Retention time Tr (min)=3.48

[M+H]+: m/z 425; [M+HCO₂H–H]–: m/z 469

Optical rotation: OR=+75.0+/–1.4; C=1.794 mg/0.5 ml DMSO.

The above purifications also produce a second diastereoisomer, (R)-1-((R)-2-hydroxy-2-phenylethyl)-2-methyl-7-morpholin-4-yl-2-trifluoromethyl-2,3-dihydro-1H-imidazo[1,2-a]pyrimidin-5-one.

EXAMPLE 12

(2S)-2-Methyl-1-((R) or (S)-1-methyl-2-phenylethyl)-7-morpholin-4-yl-2-trifluoromethyl-2,3-dihydro-1H-imidazo[1,2-a]pyrimidin-5-one

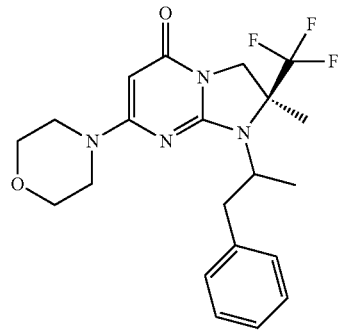 [SMILES: CC(Cc1ccccc1)N1c2nc(N3CCOCC3)cc(=O)n2C[C@@]1(C)C(F)(F)F]

A solution of 800 mg of sodium hydroxide in 5 ml of water and then 90 mg of tetrabutylammonium hydrogen sulphate and 524 mg of (R,S)-2-bromo-1-phenylpropane in 5 ml of tetrahydrofuran are added, at ambient temperature and under an argon atmosphere, to a solution of 400 mg of (S)-2-methyl-7-morpholin-4-yl-2-trifluoromethyl-2,3-dihydro-1H-imidazo[1,2-a]-pyrimidin-5-one (Example 1j) in 5 ml of toluene. The mixture obtained is then heated at 60° C. for eighteen hours. After cooling, 50 ml of ethyl acetate and a saturated aqueous solution of sodium chloride are added to the resulting mixture. The organic phase is separated and then dried over magnesium sulphate, filtered and concentrated under reduced pressure. The residue obtained is purified by silica chromatography (eluent: CH₂Cl₂/MeOH: 97/03) so as to give 110 mg of a residue which is purified on a chiral column:

Conditions: stationary phase: Chiralpak IA; mobile phase: EtOH (05%)/heptane (95%) then, second stationary phase: Hypersil C18 Elite, mobile phase: ACN (40%)/H₂O (60%).

8.2 mg of (S)-2-methyl-1-(1-methyl-2-phenylethyl)-7-morpholin-4-yl-2-trifluoromethyl-2,3-dihydro-1H-imidazo[1,2-a]pyrimidin-5-one are thus obtained in the form of a single diastereoisomer of undetermined configuration on the phenethyl chain and the characteristics of which are the following:

¹H NMR spectrum:

1.31 (d, J=6.8 Hz, 3 H); 1.66 (s, 3 H); 3.01 to 3.13 (m, 1 H); 3.35 to 3.43 (m, 1 H); 3.45 to 3.49 (m, 4 H); 3.65 to 3.71 (m,

4 H); 3.74 (s, 1 H); 3.87 (d, J=12.2 Hz, 1 H); 4.06 (d, J=12.2 Hz, 1 H); 4.86 to 4.92 (m, 1 H); 7.15 to 7.25 (m, 3 H); 7.28 to 7.35 (m, 2 H).

Mass spectrometry: method B
Retention time Tr (min)=4.30
[M+H]+: m/z 423.

EXAMPLE 13

(S)-2-Methyl-7-morpholin-4-yl-1-((R) or (S)-1-phenylpropyl)-2-trifluoromethyl-2,3-dihydro-1H-imidazo[1,2-a]pyrimidin-5-one

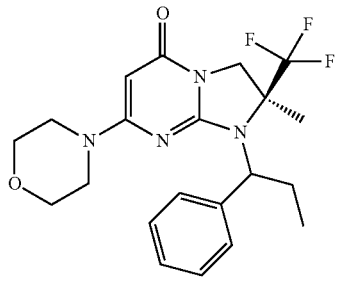 [SMILES: CCC(c1ccccc1)N1c2nc(N3CCOCC3)cc(=O)n2C[C@@]1(C)C(F)(F)F]

The chromatographic separation described above, in Example 12, also gave 11.2 mg of a first diastereosiomer of (S)-2-methyl-7-morpholin-4-yl-1-(1-phenylpropyl)-2-trifluoromethyl-2,3-dihydro-1H-imidazo[1,2-a]pyrimidin-5-one, of undetermined configuration on the benzyl chain and the characteristics of which are the following:

¹H NMR spectrum:
0.90 (t, J=7.5 Hz, 3 H); 1.57 (s, 3 H); 2.34 to 2.47 (m, 2 H); 3.39 (m, 4 H); 3.62 (m, 4 H); 3.86 (d, J=12.7 Hz, 1 H); 4.13 (d, J=12.7 Hz, 1 H); 4.48 (t, J=7.5 Hz, 1 H); 4.88 (s, 1 H); 7.25 (t, J=7.5 Hz, 1 H); 7.30 to 7.36 (t, J=7.5 Hz, 2 H); 7.55 (d, J=7.5 Hz, 2 H).

Mass spectrometry: method B
Retention time Tr (min)=4.25
[M+H]+: m/z 423.

EXAMPLE 14

(S)-2-Methyl-7-morpholin-4-yl-1-((S) or (R)-1-phenylpropyl)-2-trifluoromethyl-2,3-dihydro-1H-imidazo[1,2-a]pyrimidin-5-one

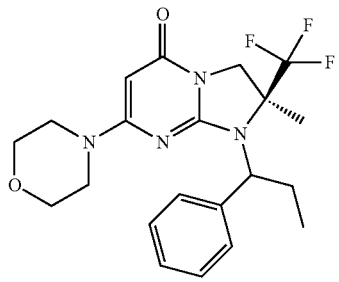 [SMILES: CCC(c1ccccc1)N1c2nc(N3CCOCC3)cc(=O)n2C[C@@]1(C)C(F)(F)F]

The chiral separation described above, in Example 12, also gave 40.5 mg of the second diastereoisomer of (S)-2-methyl-7-morpholin-4-yl-1-(1-phenylpropyl)-2-trifluoromethyl-2,3-dihydro-1H-imidazo[1,2-a]pyrimidin-5-one, of undetermined configuration on the benzyl chain and the characteristics of which are the following:

¹H NMR spectrum:
0.89 (t, J=7.5 Hz, 3 H); 1.71 (s, 3 H); 1.94 to 2.08 (m, 1 H); 2.52 to 2.59 (m, 1 H); 3.38 (m, 4 H); 3.61 (m, 4 H); 3.98 (d, J=12.7 Hz, 1 H); 4.12 (d, J=12.7 Hz, 1 H); 4.50 (dd, J=7.1 and 8.6 Hz, 1 H); 4.92 (s, 1 H); 7.21 (t, J=7.5 Hz, 1 H); 7.29 (t, J=7.5 Hz, 2 H); 7.55 (d, J=7.5 Hz, 2 H).

Mass spectrometry: method B
Retention time Tr (min)=4.14
[M+H]+: m/z 423.

EXAMPLE 15

(S)-2-Methyl-7-morpholin-4-yl-1-[2-(4-morpholin-4-ylphenyl)ethyl]-2-trifluoromethyl-2,3-dihydro-1H-imidazo[1,2-a]pyrimidin-5-one

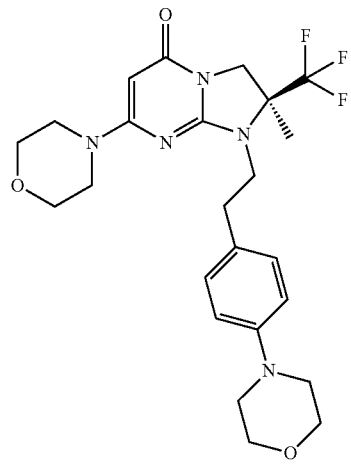 [SMILES: C[C@@]1(C(F)(F)F)Cn2c(nc(N3CCOCC3)cc2=O)N1CCc1ccc(N2CCOCC2)cc1]

135 mg of 2-(4-morpholinophenyl)ethanol and 223 mg of polymer-supported triphenylphosphine (3 mmol/g) are added to a solution of 100 mg of (S)-2-methyl-7-morpholin-4-yl-2-trifluoromethyl-2,3-dihydro-1H-imidazo[1,2-a]-pyrimidin-5-one (Example 1j) in 5 ml of tetrahydrofuran. After stirring for five minutes at ambient temperature, 0.12 ml of diethyl azodicarboxylate is added. The resulting reaction mixture is then stirred overnight at ambient temperature. After filtration, the filtrate is evaporated under reduced pressure. The residue obtained is purified by silica column chromatography (eluent: dichloromethane/methanol 97/03), so as to give 40 mg of (S)-2-methyl-7-morpholin-4-yl-1-[2-(4-morpholin-4-ylphenyl)ethyl]-2-trifluoromethyl-2,3-dihydro-1H-imidazo[1,2-a]pyrimidin-5-one, the characteristics of which are the following:

¹H NMR spectrum:
1.53 (s, 3 H); 2.70 to 2.81 (m, 1 H); 2.86 to 2.98 (m, 1 H); 3.02 to 3.08 (m, 4 H); 3.35 to 3.58 (m, 6 H); 3.62 to 3.67 (m, 4 H); 3.70 to 3.75 (m, 4 H); 3.84 (d, J=12.5 Hz, 1 H); 4.11 (d, J=12.5 Hz, 1 H); 4.88 (s, 1 H); 6.88 (d, J=8.6 Hz, 2 H); 7.08 (d, J=8.6 Hz, 2 H).

Mass spectrometry: method A
Retention time Tr (min)=0.87
[M+H]+: m/z 494; [M+2H]2+: m/z 247.5 (base peak).

EXAMPLE 16

(2S)-2-Methyl-7-(morpholin-4-yl)-1-((R) and (S)-1-phenylethyl)-2-(trifluoromethyl)-2,3-dihydroimidazo[1,2-a]pyrimidin-5(1H)-one

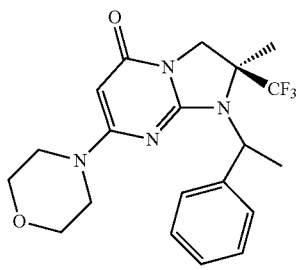 [SMILES: CC(c1ccccc1)N1c2nc(N3CCOCC3)cc(=O)n2C[C@@]1(C)C(F)(F)F]

Stage b:

190 mg of (S)-7-chloro-2-methyl-1-(1-phenylethyl)-2-(trifluoromethyl)-2,3-dihydroimidazo[1,2-a]pyrimidin-5(1H)-one and 3 ml of morpholine are introduced into a round-bottomed flask. The resulting mixture is heated at 80° C. for 30 minutes. After cooling, the reaction mixture is concentrated under reduced pressure. The residue is purified by silica chromatography (eluent: $CH_2Cl_2$/MeOH 97.5/2.5) so as to give 28 mg of a 1/2 mixture of the two diastereoisomers of (2S)-2-methyl-7-(morpholin-4-yl)-1-(1-phenylethyl)-2-(trifluoromethyl)-2,3-dihydroimidazo[1,2-a]pyrimidin-5(1H)-one, the characteristics of which are the following:

$^1$H NMR spectrum:

2/3-1/3 mixture of diastereoisomers with: 1.74 to 1.79 (m, 5 H); 1.82 (d, J=7.0 Hz, 1 H); 3.16 to 3.26 (m, 4 H); 3.41 to 3.56 (m, 4 H); 3.91 to 4.02 (m, 1 H); 4.13 (d, J=12.5 Hz, 0.65 H); 4.17 (d, J=12.5 Hz, 0.35 H); 4.79 (s, 0.65 H); 4.85 (s, 0.35 H); 4.86 to 4.94 (m, 1 H); 7.16 to 7.26 (m, 1 H); 7.27 to 7.35 (m, 2 H); 7.42 (d, J=7.8 Hz, 1.3 H); 7.46 (d, J=7.8 Hz, 0.7; H).

Mass spectrometry: method A

Retention time Tr (min)=0.93 and 0.94 with 2/3-1/3 mixture of diastereoisomers

[M+H]+: m/z 409

Stage a:

200 mg of (S)-7-chloro-2-methyl-2-trifluoromethyl-2,3-dihydro-1H-imidazo[1,2-a]pyrimidin-5-one prepared (Example 11) in 5 ml of tetrahydrofuran, 192 mg of (R,S)-phenylethanol and 537 mg of polymer-supported triphenylphosphine (3 mmol/g) are introduced into a round-bottomed flask. After having stirred for 5 minutes at ambient temperature, 275 mg of diethyl (E)-diazene-1,2-dicarboxylate (DIAD) are added. The reaction mixture is subsequently stirred for 4 hours at ambient temperature before filtration. The filtrate is then concentrated under reduced pressure and the residue is purified by silica chromatography (eluent: $CH_2Cl_2$/AcOEt: 96/04) so as to give 200 mg of a 90/10 mixture of the two diastereoisomers of (S)-7-chloro-2-methyl-1-(1-phenylethyl)-2-(trifluoromethyl)-2,3-dihydroimidazo[1,2-a]pyrimidin-5(1H)-one, the characteristics of which are the following:

Mass spectrometry: method B

Retention time Tr (min)=4.56 and 4.47 (90%-10% mixture of diastereoisomers).

[M+H]+: m/z 358.

EXAMPLE 17

1-[2-(4-Methoxyphenyl)ethyl]-2,2-dimethyl-7-morpholin-4-yl-2,3-dihydro-1H-imidazo[1,2-a]pyrimidin-5-one

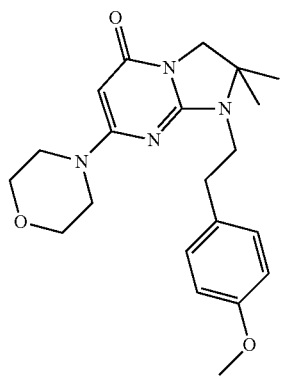 [SMILES: COc1ccc(CCN2c3nc(N4CCOCC4)cc(=O)n3CC2(C)C)cc1]

Stage e: 1-[2-(4-Methoxyphenyl)ethyl]-2,2-dimethyl-7-morpholin-4-yl-2,3-dihydro-1H-imidazo[1,2-a]pyrimidin-5-one The product is prepared according to the procedure described in Example 1, using 100 mg of 2,2-dimethyl-7-morpholin-4-yl-2,3-dihydro-1H-imidazo[1,2-a]pyrimidin-5-one and 0.94 ml of 4-methoxyphenethyl bromide, replacing the sodium hydride with caesium carbonate. After purification by silica column chromatography (eluent: dichloromethane/methanol: 98/02), 39 mg of 1-[2-(4-methoxyphenyl)ethyl]-2,2-dimethyl-7-morpholin-4-yl-2,3-dihydro-1H-imidazo[1,2-a]pyrimidin-5-one are obtained, the characteristics of which are the following:

$^1$H NMR spectrum:

1.21 (s, 6 H); 2.83 (t, J=7.7 Hz, 2 H); 3.32 to 3.38 (m, 2 H); 3.40 to 3.45 (m, 4 H); 3.59 (s, 2 H); 3.61 to 3.65 (m, 4 H); 3.72 (s, 3 H); 4.78 (s, 1 H); 6.86 (d, J=8.6 Hz, 2 H); 7.14 (d, J=8.6 Hz, 2 H).

Mass spectrometry: method A

Retention time Tr (min)=0.84

[M+H]+: m/z 385.

Stage d: 2,2-Dimethyl-7-morpholin-4-yl-2,3-dihydro-1H-imidazo[1,2-a]-pyrimidin-5-one

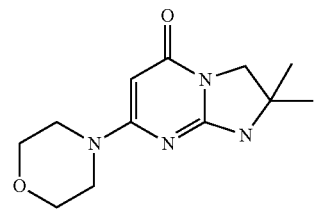 [SMILES: CC1(C)Cn2c(nc(N3CCOCC3)cc2=O)N1]

A mixture of 1 g of 7-chloro-2,2-dimethyl-2,3-dihydro-1H-imidazo[1,2-a]pyrimidin-5-one and 10 ml of morpholine is heated at 120° C. for 1 hour. After cooling, the reaction mixture is concentrated under reduced pressure. The residue obtained is purified by silica chromatography (eluent: CH₂Cl₂/MeOH 97/03) so as to give 650 mg of 2,2-dimethyl-7-morpholin-4-yl-2,3-dihydro-1H-imidazo[1,2-a]pyrimidin-5-one, the characteristics of which are the following:
Mass spectrometry: method A
[M+H]+: m/z 251.

Stage c: 7-Chloro-2,2-dimethyl-2,3-dihydro-1H-imidazo[1,2-a]pyrimidin-5-one

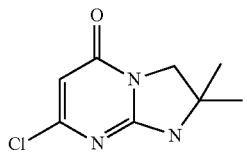

4.5 g of 7-hydroxy-2,2-dimethyl-2,3-dihydro-1H-imidazo[1,2-a]pyrimidin-5-one and 35 ml of phosphorus oxychloride are introduced into a round-bottomed flask. The resulting mixture is then heated at 120° C. for three hours. After cooling, the reaction mixture is concentrated to dryness under reduced pressure. Ice is added to the residue obtained, and then concentrated sodium hydroxide is added until a pH in the region of 5-6 is obtained. The solid formed is filtered off so as to give 1 g of 7-chloro-2,2-dimethyl-2,3-dihydro-1H-imidazo[1,2-a]pyrimidin-5-one, in the form of a brown solid, the characteristics of which are the following:
Mass spectrometry: method B
[M+H]+: m/z 200; [M−H]−: m/z 198.

Stage b: 7-Hydroxy-2,2-dimethyl-2,3-dihydro-1H-imidazo[1,2-a]pyrimidin-5-one

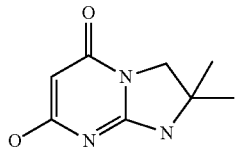

The process is carried out according to the procedure described in stage g of Example 1, using 5 g of 4,4-dimethylimidazolidin-2-ylideneamine hydrobromide, 4 ml of diethyl malonate and 2.8 g of sodium methoxide. 4.5 g of 7-hydroxy-2,2-dimethyl-2,3-dihydro-1H-imidazo[1,2-a]pyrimidin-5-one are thus obtained in the form of a white solid.

Stage a: 4,4-Dimethylimidazolidin-2-ylideneamine hydrobromide

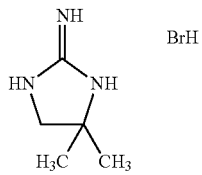

The process is carried out according to the procedure described in stage f of Example 1, using 21 g of 1,2-diamino-2-methylpropane and 25.3 g of cyanogen bromide. 46 g of 4,4-dimethylimidazolidin-2-ylideneamine hydrobromide are thus obtained, in the form of a white solid, the characteristics of which are the following:
Mass spectrometry: method B
[M+H]+: m/z 114.

EXAMPLE 18

(2S)-6-Fluoro-1-[2-(4-methoxyphenyl)ethyl]-2-methyl-7-(morpholin-4-yl)-2-(trifluoromethyl)-2,3-dihydroimidazo[1,2-a]pyrimidin-5(1H)-one Stage e:

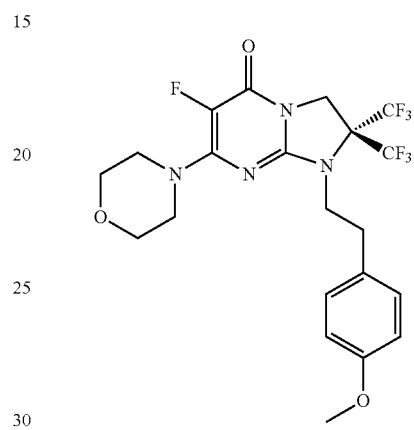

The two enantiomers of (2R,2S)-6-fluoro-1-[2-(4-methoxyphenyl)ethyl]-2-methyl-7-(morpholin-4-yl)-2-(trifluoromethyl)-2,3-dihydroimidazo[1,2-a]-pyrimidin-5(1H)-one were separated by chiral chromatography using 130 mg of the racemic mixture:
Stationary phase: Chiralcel OJ 20 μm; mobile phase: EtOH (100%).
62 mg of (2S)-6-fluoro-1-[2-(4-methoxyphenyl)ethyl]-2-methyl-7-(morpholin-4-yl)-2-(trifluoromethyl)-2,3-dihydroimidazo[1,2-a]pyrimidin-5(1H)-one are thus obtained, the characteristics of which are the following:
¹H NMR spectrum (500 MHz):
1.55 (s, 3 H); 2.79 (m, 1 H); 2.93 (m, 1 H); 3.41 (m, 1 H); 3.52 (m, 1 H); 3.59 (m, 4 H); 3.69 (m, 4 H); 3.74 (s, 3 H); 3.94 (d, J=12.3 Hz, 1 H); 4.17 (d, J=12.3 Hz, 1 H); 6.89 (d, J=8.2 Hz, 2 H); 7.15 (d, J=8.2 Hz, 2 H)
Mass spectrometry: method A
Retention time Tr (min)=1.01
[M+H]+: m/z 457.

Stage d: (2R,2S)-6-Fluoro-1-[2-(4-methoxyphenyl)ethyl]-2-methyl-7-(morpholin-4-yl)-2-(trifluoromethyl)-2,3-dihydroimidazo[1,2-a]pyrimidin-5(1H)-one

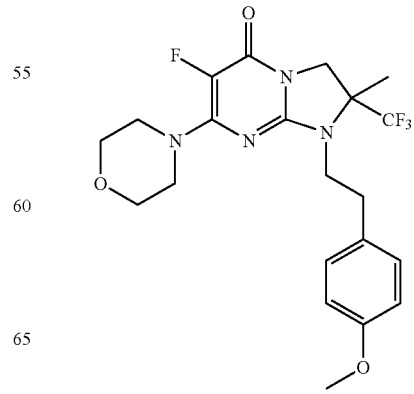

243 mg of caesium carbonate and 120 mg of 4-methoxyphenethyl bromide are added to a solution of 120 mg of (2R,2S)-6-fluoro-2-methyl-7-(morpholin-4-yl)-2-(trifluoromethyl)-2,3-dihydroimidazo[1,2-a]pyrimidin-5(1H)one in 5 ml of acetonitrile. The reaction mixture is then heated at 60° C. for seven hours. After cooling, the reaction mixture is concentrated under reduced pressure. 5 ml of cold water and 20 ml of ethyl acetate are added to the residue obtained. The organic phase is separated, dried over magnesium sulphate, filtered and then concentrated under reduced pressure. The residue obtained is purified by silica chromatography (eluent: dichloromethane/methanol: 97.5/2.5) so as to give 130 mg of (2R,2S)-6-fluoro-1-[2-(4-methoxyphenyl)ethyl]-2-methyl-7-(morpholin-4-yl)-2-(trifluoromethyl)-2,3-dihydroimidazo[1,2-a]pyrimidin-5(1H)-one, the characteristics of which are the following:
Mass spectrometry: method B
Retention time Tr (min)=4.27
[M+H]+: m/z 457.

Stage c: (2R,2S)-6-Fluoro-2-methyl-7-(morpholin-4-yl)-2-(trifluoromethyl)-2,3-dihydroimidazo[1,2-a]pyrimidin-5(1H)-one

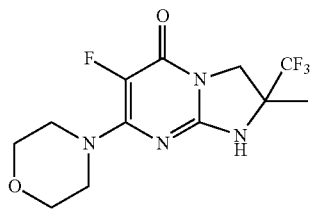 [SMILES: CC1(C(F)(F)F)Cn2c(nc(N3CCOCC3)c(F)c2=O)N1]

A mixture of 220 mg of (2R,2S)-7-chloro-6-fluoro-2-methyl-2-(trifluoromethyl)-2,3-dihydroimidazo[1,2-a]pyrimidin-5(1H)-one in 3 ml of morpholine is heated at 60° C. for three hours. After cooling, the reaction mixture is concentrated under reduced pressure. 5 ml of cold water and 20 ml of ethyl acetate are added to the residue obtained. The organic phase is separated, dried over magnesium sulphate, filtered and then concentrated under reduced pressure so as to give 220 mg of (2R,2S)-6-fluoro-2-methyl-7-(morpholin-4-yl)-2-(trifluoromethyl)-2,3-dihydroimidazo[1,2-a]pyrimidin-5(1H)-one, the characteristics of which are the following:
Mass spectrometry: method A
Retention time Tr (min)=0.55
[M+H]+: m/z 323; [M−H]−: m/z 321.

Stage b: (2R,2S)-7-Chloro-6-fluoro-2-methyl-2-(trifluoromethyl)-2,3-dihydroimidazo[1,2-a]pyrimidin-5(1H)-one

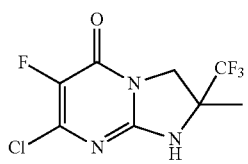 [SMILES: CC1(C(F)(F)F)Cn2c(nc(Cl)c(F)c2=O)N1]

The product is prepared according to the procedure described in stage h of Example 1, using 430 mg of (2R,2S)-6-fluoro-7-hydroxy-2-methyl-2-(trifluoromethyl)-2,3-dihydroimidazo[1,2-a]pyrimidin-5(1H)-one (as isolated in stage (a) below) in place of the (2R,2S)-7-hydroxy-2-methyl-2-trifluoromethyl-2,3-dihydro-1H-imidazo[1,2-a]pyrimidin-5-one and 0.800 ml of phosphorus oxychloride. After purification by silica column chromatography (eluent: dichloromethane/methanol 97/03), 220 mg of (2R,2S)-7-chloro-6-fluoro-2-methyl-2-(trifluoromethyl)-2,3-dihydroimidazo[1,2-a]pyrimidin-5(1H)-one are obtained, the characteristics of which are the following:
Mass spectrometry: method B
Retention time Tr (min)=2.92
[M+H]+: m/z 272; [M−H]−: m/z 270.

Stage a: (2R,2S)-6-Fluoro-7-hydroxy-2-methyl-2-(trifluoromethyl)-2,3-dihydroimidazo[1,2-a]pyrimidin-5(1H)-one

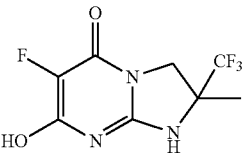 [SMILES: CC1(C(F)(F)F)Cn2c(nc(O)c(F)c2=O)N1]

The product is prepared according to the procedure described in stage g of Example 1, using 1 g of 4-methyl-4-trifluoromethylimidazolidin-2-ylideneamine, 605 mg of dimethyl fluoropropanedioate in place of the diethyl malonate and 440 mg of sodium methoxide. 490 mg of a mixture containing 50% of (2R,2S)-6-fluoro-7-hydroxy-2-methyl-2-(trifluoromethyl)-2,3-dihydroimidazo[1,2-a]pyrimidin-5(1H)-one are thus obtained, said product being used as it is in the next stage.

EXAMPLE 19

(2S)-1-Benzyl-6-fluoro-2-methyl-7-(morpholin-4-yl)-2-(trifluoromethyl)-2,3-dihydroimidazo[1,2-a]pyrimidin-5(1H)-one Stage b:

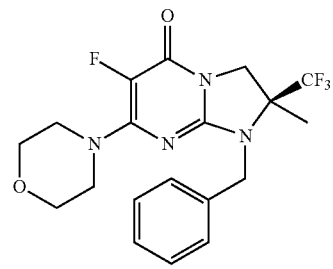 [SMILES: C[C@@]1(C(F)(F)F)Cn2c(nc(N3CCOCC3)c(F)c2=O)N1Cc1ccccc1]

The two enantiomers of (R,S)-1-benzyl-6-fluoro-2-methyl-7-(morpholin-4-yl)-2-(trifluoromethyl)-2,3-dihydroimidazo[1,2-a]pyrimidin-5(1H)-one were separated by chiral chromatography using 75 mg of the racemic mixture:
Stationary phase: Whelk 01 RR
Mobile phase: 80% heptane 20% EtOH.
35 mg of (2S)-1-benzyl-6-fluoro-2-methyl-7-(morpholin-4-yl)-2-(trifluoromethyl)-2,3-dihydroimidazo[1,2-a]pyrimidin-5(1H)-one are thus obtained, the characteristics of which are the following:
$^1$H NMR spectrum (400 MHz):

1.63 (s, 3 H); 3.45 (m, 4 H); 3.53 (m, 4 H); 4.06 (d, J=12.2 Hz, 1 H); 4.21 (d, J=12.2 Hz, 1 H); 4.55 (d, J=16.5 Hz, 1 H); 4.61 (d, J=16.5 Hz, 1 H); 7.22 to 7.28 (m, 1 H); 7.29 to 7.38 (m, 4 H).
Mass spectrometry: method A
Retention time Tr (min)=0.95
[M+H]+: m/z 413.

Stage a: (R,S)-1-Benzyl-6-fluoro-2-methyl-7-(morpholin-4-yl)-2-(trifluoromethyl)-2,3-dihydroimidazo[1,2-a]pyrimidin-5(1H)-one

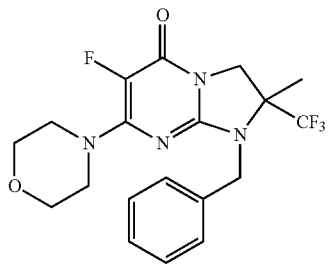 [SMILES: CC1(C(F)(F)F)Cn2c(nc(N3CCOCC3)c(F)c2=O)N1Cc1ccccc1]

121 mg of caesium carbonate and 0.074 ml of benzyl bromide are added to a solution of 100 mg of (R,S)-6-fluoro-2-methyl-7-(morpholin-4-yl)-2-(trifluoromethyl)-2,3-dihydroimidazo[1,2-a]pyrimidin-5(1H)-one (prepared according to the protocol of Example 18c) in 5 ml of acetonitrile. The reaction mixture is then stirred at ambient temperature for one hour. The resulting reaction mixture is concentrated under reduced pressure. 5 ml of cold water and 20 ml of ethyl acetate are added to the residue obtained. The organic phase is separated, dried over magnesium sulphate, filtered and then concentrated under reduced pressure. The residue obtained is purified by silica chromatography (eluent: CH₂Cl₂/MeOH: 97.5/2.5) so as to give 75 mg of (R,S)-1-benzyl-6-fluoro-2-methyl-7-(morpholin-4-yl)-2-(trifluoromethyl)-2,3-dihydroimidazo[1,2-a]pyrimidin-5(1H)-one, the characteristics of which are the following:
Mass spectrometry: method B
Retention time Tr (min)=4.10
[M+H]+: m/z 413.

EXAMPLE 20

(2S)-1-[(5-Chloro-1-benzothiophen-3-yl)methyl]-2-methyl-7-(morpholin-4-yl)-2-(trifluoromethyl)-2,3-dihydroimidazo[1,2-a]pyrimidin-5(1H)-one

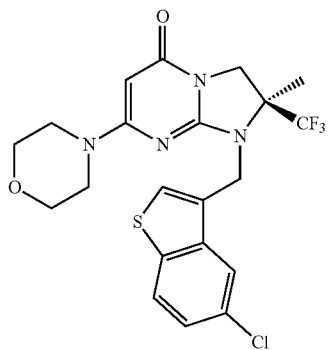 [SMILES: C[C@@]1(C(F)(F)F)Cn2c(nc(N3CCOCC3)cc2=O)N1Cc1csc2ccc(Cl)cc12]

The product is prepared according to the procedure described in stage k of Example 1, using 100 mg of (2S)-2-methyl-7-morpholin-4-yl-2-trifluoromethyl-2,3-dihydro-1H-imidazo[1,2-a]pyrimidin-5-one (Example 1j) and 103 mg of 3-(bromomethyl)-5-chloro-1-benzothiophene, replacing the sodium hydride with caesium carbonate. After purification by preparative HPLC/MS (method C), 49 mg of (2S)-1-[(5-chloro-1-benzothiophen-3-yl)methyl]-2-methyl-7-(morpholin-4-yl)-2-(trifluoromethyl)-2,3-dihydroimidazo[1,2-a]pyrimidin-5(1H)-one are obtained in the form of a brown solid, the characteristics of which are the following:
¹H NMR spectrum (400 MHz):
1.65 (s, 3 H); 3.31 to 3.36 (m, 4 H); 3.53 (m, 4 H); 3.98 (d, J=12.5 Hz, 1 H); 4.17 (d, J=12.5 Hz, 1 H); 4.82 (d, J=16.5 Hz, 1 H); 4.90 to 4.98 (m, 2 H); 7.41 (dd, J=2.0 and 8.6 Hz, 1 H); 7.79 (s, 1 H); 8.03 (d, J=8.6 Hz, 1 H); 8.16 (d, J=2.0 Hz, 1 H)
Mass spectrometry: method A
Retention time Tr (min)=1.06
[M+H]+: m/z 485.

EXAMPLE 21

(2S)-2-Methyl-7-(morpholin-4-yl)-1-(phenylcarbonyl)-2-(trifluoromethyl)-2,3-dihydroimidazo[1,2-a]pyrimidin-5(1H)-one

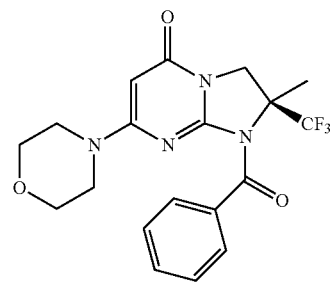 [SMILES: C[C@@]1(C(F)(F)F)Cn2c(nc(N3CCOCC3)cc2=O)N1C(=O)c1ccccc1]

14.2 mg of sodium hydride are added to a solution of 150 mg of (2S)-2-methyl-7-morpholin-4-yl-2-trifluoromethyl-2,3-dihydro-1H-imidazo[1,2-a]-pyrimidin-5-one (Example 1j), in 3 ml of tetrahydrofuran. After stirring for 25 minutes at a temperature in the region of 20° C., 0.092 ml of benzoyl chloride is added. The reaction medium is stirred for 1 hour at ambient temperature before the addition of 1.5 ml of a saturated solution of sodium bicarbonate and ethyl acetate. The organic phase is successively separated, washed with a saturated aqueous solution of sodium chloride, dried over magnesium sulphate, filtered, and then concentrated under reduced pressure. After purification by silica column chromatography (eluent: dichloromethane/methanol: 98/02), 49 mg of (2S)-2-methyl-7-(morpholin-4-yl)-1-(phenylcarbonyl)-2-(trifluoromethyl)-2,3-dihydroimidazo[1,2-a]pyrimidin-5(1H)one are obtained in the form of a brown solid, the characteristics of which are the following:
¹H NMR spectrum:
1.96 (s, 3 H); 2.72 to 2.92 (m, 4 H); 3.24 to 3.36 (m, partially masked, 4 H); 4.12 (d, J=12.5 Hz, 1 H); 4.34 (d, J=12.5 Hz, 1 H); 5.01 (s, 1 H); 7.45 (t, J=7.6 Hz, 2 H); 7.53 (t, J=7.6 Hz, 1 H); 7.63 (d, J=7.6 Hz, 2 H)
Mass spectrometry: method B
Retention time Tr (min)=3.76
[M+H]+: m/z 409.

EXAMPLE 22

(2S)-1-[(1R or 1S)-1-(3-Fluorophenyl)ethyl]-2-methyl-7-(morpholin-4-yl)-2-(trifluoromethyl)-2,3-dihydroimidazo[1,2-a]pyrimidin-5(1H)-one

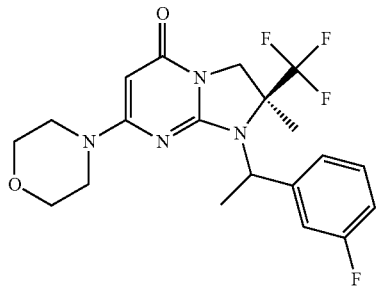 [SMILES: CC(c1cccc(F)c1)N1c2nc(N3CCOCC3)cc(=O)n2C[C@@]1(C)C(F)(F)F]

Stage b:

The two diastereoisomers of (2S)-1-[1-(3-fluorophenyl)ethyl]-2-methyl-7-(morpholin-4-yl)-2-(trifluoromethyl)-2,3-dihydroimidazo[1,2-a]pyrimidin-5(1H)-one were separated by chiral chromatography using 66 mg of a 65/35 mixture of the two diastereoisomers:

Stationary phase: Chiralpak AD 20 µm 8×35 cm;
Mobile phase: 85% heptane 15% EtOH.

21 mg of (2S)-1-[(1R or 1S)-1-(3-fluorophenyl)ethyl]-2-methyl-7-(morpholin-4-yl)-2-(trifluoromethyl)-2,3-dihydroimidazo[1,2-a]pyrimidin-5(1H)-one are thus obtained, the characteristics of which are the following:

$^1$H NMR spectrum (500 MHz):
1.76 (s, 3 H); 1.80 (d, J=6.8 Hz, 3 H); 3.16 to 3.28 (m, 4 H); 3.41 to 3.55 (m, 4 H); 4.03 (d, J=12.7 Hz, 1 H); 4.17 (d, J=12.7 Hz, 1 H); 4.82 (s, 1 H); 4.90 (q, J=6.8 Hz, 1 H); 7.07 (dt, J=2.0 and 8.3 Hz, 1 H); 7.27 to 7.40 (m, 3 H)

Mass spectrometry: method B
Retention time Tr (min)=4.07
[M+H]+: m/z 427

Stage a: (2S)-1-[(1R and 1S)-1-(3-Fluorophenyl)ethyl]-2-methyl-7-(morpholin-4-yl)-2-(trifluoromethyl)-2,3-dihydroimidazo[1,2-a]pyrimidin-5(1H)-one The product can be prepared according to the procedure described in stage d of Example 18, but using 300 mg of (2S)-2-methyl-7-(morpholin-4-yl)-2-(trifluoromethyl)-2,3-dihydroimidazo[1,2-a]pyrimidin-5(1H)-one, 643 mg of caesium carbonate and 234 mg of 1-(1-chloroethyl)-3-fluorobenzene in 13 ml of acetonitrile. After purification by silica column chromatography (eluent: dichloromethane/methanol: 97/03), 66 mg of a 65/35 mixture of the two diastereoisomers of (2S)-1-[(1R and 1S)-1-(3-fluorophenyl)ethyl]-2-methyl-7-(morpholin-4-yl)-2-(trifluoromethyl)-2,3-dihydroimidazo[1,2-a]pyrimidin-5(1H)-one are obtained in the form of a pale yellow sticky residue, the characteristics of which are the following:

Mass spectrometry: method A
Retention time Tr (min)=0.59 and 0.67; mixture of the diastereoisomers
[M+H]+: m/z 427; [M−H]−: m/z 425.

EXAMPLE 23

(2S)-1-{[4-Chloro-2-(trifluoromethyl)quinolin-6-yl]methyl}-2-methyl-7-(morpholin-4-yl)-2-(trifluoromethyl)-2,3-dihydroimidazo[1,2-a]pyrimidin-5(1H)-one trifluoroacetate

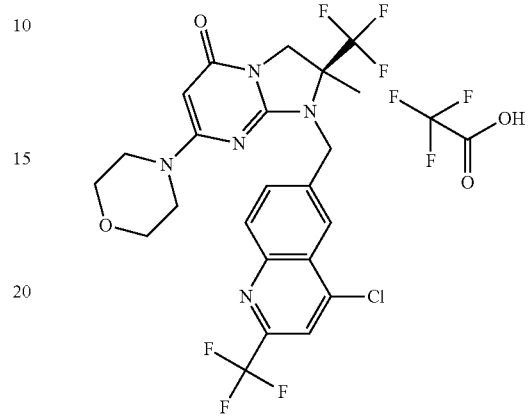

The product is prepared according to the procedure described in stage k of Example 1, using 95 mg of (2S)-2-methyl-7-(morpholin-4-yl)-2-(trifluoromethyl)-2,3-dihydroimidazo[1,2-a]pyrimidin-5(1H)-one (Example 1j) and 101 mg of 6-(bromomethyl)-4-chloro-2-(trifluoromethyl)quinoline, replacing the sodium hydride with 203 g of caesium carbonate. After purification by preparative HPLC/MS (method C), 40 mg of (2S)-1-{[4-chloro-2-(trifluoromethyl)quinolin-6-yl]methyl}-2-methyl-7-(morpholin-4-yl)-2-(trifluoromethyl)-2,3-dihydroimidazo[1,2-a]pyrimidin-5(1H)-one, in the form of a trifluoroacetic acid salt, are obtained in the form of a beige powder, the characteristics of which are the following:

$^1$H NMR spectrum (400 MHz):
1.74 (s, 3 H); 3.26 to 3.31 (m, 4 H); 3.45 to 3.50 (m, 4 H); 4.03 (d, J=12.7 Hz, 1 H); 4.21 (d, J=12.7 Hz, 1 H); 4.90 (s, 1 H); 4.93 (s, 2 H); 8.03 (dd, J=2.0 and 8.8 Hz, 1 H); 8.25 (d, J=8.8 Hz, 1 H); 8.28 (s, 1 H); 8.36 (d, J=2.0 Hz, 1 H)

Mass spectrometry: method A
Retention time Tr (min)=1.08
[M+H]+: m/z 548.

EXAMPLE 24

(2S)-1-(3-Bromo-4-fluorobenzyl)-2-methyl-7-(morpholin-4-yl)-2-(trifluoromethyl)-2,3-dihydroimidazo[1,2-a]pyrimidin-5(1H)-one Chiral

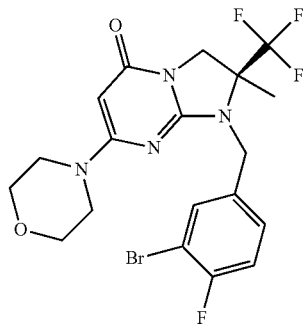

The product is prepared according to the procedure described in stage k of Example 1, using 100 mg of (2S)-2-methyl-7-(morpholin-4-yl)-2-(trifluoromethyl)-2,3-dihydroimidazo[1,2-a]pyrimidin-5(1H)-one (Example 1j) and 106 mg of 2-bromo-4-(bromomethyl)-1-fluorobenzene, replacing the sodium hydride with 214 mg of caesium carbonate. After purification by preparative HPLC/MS (method C), 50 mg of (2S)-1-(3-bromo-4-fluorobenzyl)-2-methyl-7-(morpholin-4-yl)-2-(trifluoromethyl)-2,3-dihydroimidazo[1,2-a]pyrimidin-5(1H)-one are obtained in the form of a off-white semi-solid, the characteristics of which are the following:

$^1$H NMR spectrum (400 MHz):

1.66 (s, 3 H); 3.29 to 3.41 (m, 4 H); 3.49 to 3.60 (m, 4 H); 3.98 (d, J=12.7 Hz, 1 H); 4.16 (d, J=12.7 Hz, 1 H); 4.60 (s, 2 H); 4.89 (s, 1 H); 7.33 (t, J=8.8 Hz, 1 H); 7.38 to 7.46 (m, 1 H); 7.76 (dd, J=2.0 and 6.8 Hz, 1 H)

Mass spectrometry: method A

Retention time Tr (min)=1.00

[M+H]+: m/z 491.

EXAMPLE 25

(2S)-1-(2,3-Difluorobenzyl)-2-methyl-7-(morpholin-4-yl)-2-(trifluoromethyl)-2,3-dihydroimidazo[1,2-a]pyrimidin-5(1H)-one

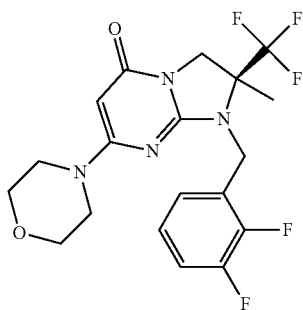

The product is prepared according to the procedure described in stage k of Example 1, using 100 mg of (2S)-2-methyl-7-(morpholin-4-yl)-2-(trifluoromethyl)-2,3-dihydroimidazo[1,2-a]pyrimidin-5(1H)-one (Example 1j) and 82 mg of 1-(bromomethyl)-2,3-difluorobenzene, replacing the sodium hydride with 214 mg of caesium carbonate. After purification by preparative HPLC/MS (method C), 90 mg of (2S)-1-(2,3-difluorobenzyl)-2-methyl-7-(morpholin-4-yl)-2-(trifluoromethyl)-2,3-dihydroimidazo[1,2-a]pyrimidin-5(1H)one are obtained in the form of a white semi-solid, the characteristics of which are the following:

$^1$H NMR spectrum (400 MHz):

1.67 (s, 3 H); 3.26 to 3.35 (m, 4 H); 3.49 to 3.58 (m, 4 H); 3.99 (d, J=12.7 Hz, 1 H); 4.18 (d, J=12.7 Hz, 1 H); 4.69 (s, 2 H); 4.89 (s, 1 H); 7.18 (m, 1 H); 7.25 (m, 1 H); 7.34 (m, 1 H)

Mass spectrometry: method A

Retention time Tr (min)=0.94

[M+H]+: m/z 431.

EXAMPLE 26

(2S)-1-[2-(3-Methoxyphenyl)ethyl]-2-methyl-7-(morpholin-4-yl)-2-(trifluoromethyl)-2,3-dihydroimidazo[1,2-a]pyrimidin-5(1H)-one

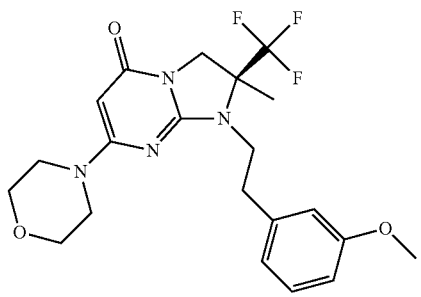

The product is prepared according to the procedure described in stage k of Example 1, using 100 mg of (2S)-2-methyl-7-(morpholin-4-yl)-2-(trifluoromethyl)-2,3-dihydroimidazo[1,2-a]pyrimidin-5(1H)-one (Example 1j) and 85 mg of 1-(2-bromoethyl)-3-methoxybenzene, replacing the sodium hydride with 214 mg of caesium carbonate. After purification by preparative HPLC/MS (method C), 65 mg of (2S)-1-[2-(3-methoxyphenyl)ethyl]-2-methyl-7-(morpholin-4-yl)-2-(trifluoromethyl)-2,3-dihydroimidazo[1,2-a]pyrimidin-5(1H)-one are obtained in the form of an oil, the characteristics of which are the following:

$^1$H NMR spectrum (400 MHz):

1.55 (s, 3 H); 2.82 (m, 1 H); 2.98 (m, 1 H); 3.39 to 3.52 (m, 5 H); 3.54 to 3.67 (m, 5 H); 3.73 (s, 3 H); 3.84 (d, J=12.7 Hz, 1 H); 4.12 (d, J=12.7 Hz, 1 H); 4.88 (s, 1 H); 6.79 (m, 3 H); 7.22 (m, 1 H)

Mass spectrometry: method A

Retention time Tr (min)=0.96

[M+H]+: m/z 439.

EXAMPLE 27

(2S)-1-[2-(2-Chlorophenyl)ethyl]-2-methyl-7-(morpholin-4-yl)-2-(trifluoromethyl)-2,3-dihydroimidazo[1,2-a]pyrimidin-5(1H)-one

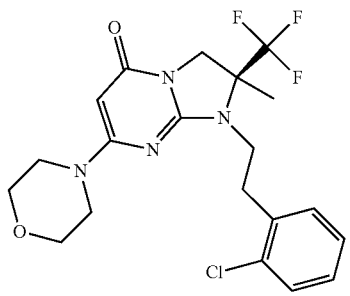

The product is prepared according to the procedure described in stage k of Example 1, using 100 mg of (2S)-2- methyl-7-(morpholin-4-yl)-2-(trifluoromethyl)-2,3-dihydroimidazo[1,2-a]pyrimidin-5(1H)-one (Example 1j) and 87 mg of 1-(2-bromoethyl)-2-chlorobenzene, replacing the sodium hydride with 214 mg of caesium carbonate. After purification by preparative HPLC/MS (method C), 40 mg of (2S)-1-[2-(2-chlorophenyl)ethyl]-2-methyl-7-(morpholin-4-yl)-2-(trifluoromethyl)-2,3-dihydroimidazo[1,2-a]pyrimidin-5(1H)one are obtained in the form of an off-white solid, the characteristics of which are the following:

$^1$H NMR spectrum (400 MHz):

1.56 (s, 3 H); 3.02 (m, 1 H); 3.16 (m, 1 H); 3.31 to 3.53 (m, partially masked, 5 H); 3.57 to 3.67 (m, 5 H); 3.86 (d, J=12.5 Hz, 1 H); 4.12 (d, J=12.5 Hz, 1 H); 4.87 (s, 1 H); 7.24 to 7.36 (m, 3 H); 7.41 to 7.47 (m, 1 H)

Mass spectrometry: method A

Retention time Tr (min)=1.04

[M+H]+: m/z 443.

EXAMPLE 28

(2S)-1-[2-(4-Chlorophenyl)ethyl]-2-methyl-7-(morpholin-4-yl)-2-(trifluoromethyl)-2,3-dihydroimidazo[1,2-a]pyrimidin-5(1H)-one

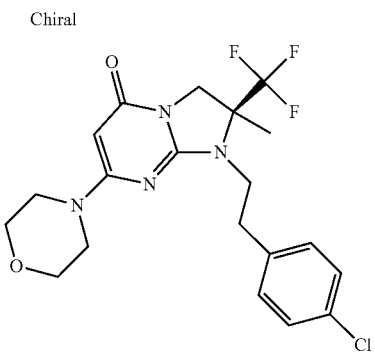 [SMILES: C[C@@]1(C(F)(F)F)Cn2c(nc(N3CCOCC3)cc2=O)N1CCc1ccc(Cl)cc1]

The product is prepared according to the procedure described in stage k of Example 1, using 100 mg of (2S)-2-methyl-7-(morpholin-4-yl)-2-(trifluoromethyl)-2,3-dihydroimidazo[1,2-a]pyrimidin-5(1H)-one (Example 1j) and 87 mg of 1-(2-bromoethyl)-4-chlorobenzene, replacing the sodium hydride with 214 mg of caesium carbonate. After purification by preparative HPLC/MS (method C), 65 mg of (2S)-1-[2-(4-chlorophenyl)ethyl]-2-methyl-7-(morpholin-4-yl)-2-(trifluoromethyl)-2,3-dihydroimidazo[1,2-a]pyrimidin-5(1H)-one are obtained in the form of a white powder, the characteristics of which are the following:

$^1$H NMR spectrum:

1.53 (s, 3 H); 2.81 to 2.91 (m, 1 H); 2.95 to 3.06 (m, 1 H); 3.32 to 3.51 (m, partially masked, 5 H); 3.55 to 3.67 (m, 5 H); 3.85 (d, J=12.5 Hz, 1 H); 4.11 (d, J=12.5 Hz, 1 H); 4.87 (s, 1 H); 7.26 (d, J=8.3 Hz, 2 H); 7.36 (d, J=8.3 Hz, 2 H)

Mass spectrometry: method A

Retention time Tr (min)=1.05

[M+H]+: m/z 443.

EXAMPLE 29

(2S)-1-[2-(3-Chlorophenyl)ethyl]-2-methyl-7-(morpholin-4-yl)-2-(trifluoromethyl)-2,3-dihydroimidazo[1,2-a]pyrimidin-5(1H)-one

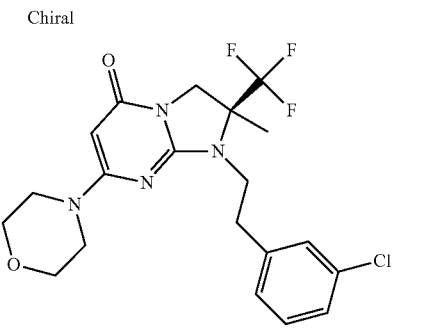 [SMILES: C[C@@]1(C(F)(F)F)Cn2c(nc(N3CCOCC3)cc2=O)N1CCc1cccc(Cl)c1]

The product is prepared according to the procedure described in stage k of Example 1, using 100 mg of (2S)-2-methyl-7-(morpholin-4-yl)-2-(trifluoromethyl)-2,3-dihydroimidazo[1,2-a]pyrimidin-5(1H)-one (Example 1j) and 87 mg of 1-(2-bromoethyl)-3-chlorobenzene, replacing the sodium hydride with 214 mg of caesium carbonate. After purification by preparative HPLC/MS (method C), 38 mg of (2S)-1-[2-(3-chlorophenyl)ethyl]-2-methyl-7-(morpholin-4-yl)-2-(trifluoromethyl)-2,3-dihydroimidazo[1,2-a]pyrimidin-5(1H)one are obtained in the form of an oil, the characteristics of which are the following:

$^1$H NMR spectrum:

1.56 (s, 3 H); 2.83 to 2.93 (m, 1 H); 2.96 to 3.05 (m, 1 H); 3.31 to 3.55 (m, partially masked, 5 H); 3.58 to 3.68 (m, 5 H); 3.85 (d, J=12.5 Hz, 1 H); 4.12 (d, J=12.5 Hz, 1 H); 4.88 (s, 1 H); 7.19 (broad d, J=7.5 Hz, 1 H); 7.26 to 7.39 (m, 3 H)

Mass spectrometry: method A

Retention time Tr (min)=1.04

[M+H]+: m/z 443.

EXAMPLE 30

(2S)-1-(1,3-Benzoxazol-2-ylmethyl)-2-methyl-7-(morpholin-4-yl)-2-(trifluoromethyl)-2,3-dihydroimidazo[1,2-a]pyrimidin-5(1H)-one

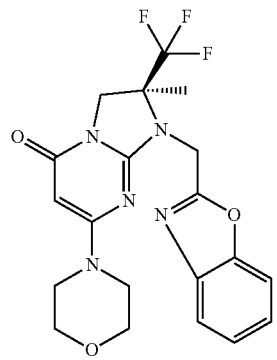 [SMILES: C[C@@]1(C(F)(F)F)Cn2c(nc(N3CCOCC3)cc2=O)N1Cc1nc2ccccc2o1]

Stage b 210 mg of (2S)-1-(1,3-benzoxazol-2-ylmethyl)-7-chloro-2-methyl-2-(trifluoromethyl)-2,3-dihydroimidazo[1,2-a]pyrimidin-5(1H)-one in 2 ml of morpholine are placed in a microwave oven. After microwave irradiation for 18 min at a temperature of 85° C., the reaction mixture is diluted with ethyl acetate. The mixture obtained is washed with water and then with a saturated aqueous solution of sodium chloride, before being dried over anhydrous magnesium sulphate, filtered and concentrated to dryness under reduced pressure. After purification by silica column chromatography (eluent: dichloromethane/methanol: gradient of 0 to 50% of MeOH), 112 mg of (2S)-1-(1,3-benzoxazol-2-ylmethyl)-2-methyl-7-(morpholin-4-yl)-2-(trifluoromethyl)-2,3-dihydroimidazo[1,2-a]pyrimidin-5(1H)-one are obtained in the form of a yellow foam, the characteristics of which are the following:

$^1$H NMR spectrum (400 MHz):

1.76 (s, 3 H); 3.17 to 3.24 (m, 4 H); 3.32 to 3.41 (m, 4 H); 4.02 (d, J=12.5 Hz, 1 H); 4.24 (d, J=12.5 Hz, 1 H); 4.85 (s, 1 H); 4.95 (s, 2 H); 7.32 to 7.42 (m, 2 H); 7.66 to 7.75 (m, 2 H)

Mass spectrometry: method A

Retention time Tr (min)=0.81

[M+H]+: m/z 436; [M−H]−: m/z 434.

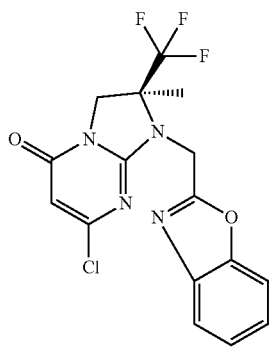 [SMILES: C[C@@]1(C(F)(F)F)Cn2c(nc(Cl)cc2=O)N1Cc1nc2ccccc2o1]

Stage a: (2S)-1-(1,3-Benzoxazol-2-ylmethyl)-2-methyl-7-chloro-2-(trifluoromethyl)-2,3-dihydroimidazo[1,2-a]pyrimidin-5(1H)-one The product is prepared according to the procedure described in stage k of Example 1, using 160 mg of (2S)-7-chloro-7-methyl-2-trifluoromethyl-2,3-dihydro-1H-imidazo[1,2-a]pyrimidin-5-one (Example 1, stage h'), and 106 mg of 2-(chloromethyl)-1,3-benzoxazole, replacing the sodium hydride with 360 mg of caesium carbonate. After reaction for 15 hours at a temperature in the region of 20° C. and treatment as described in Example 1k, 211 mg of (2S)-1-(1,3-benzoxazol-2-ylmethyl)-7-chloro-2-methyl-2-(trifluoromethyl)-2,3-dihydroimidazo[1,2-a]pyrimidin-5(1H)-one are obtained in the form of a brown foam, the characteristics of which are the following:

Mass spectrometry: method A

[M+H]+: m/z 385

Retention time Tr (min)=1.30 min.

EXAMPLE 31

(2S)-2-Methyl-7-(morpholin-4-yl)-1-[(1R or 1S)-1-phenylethyl]-2-(trifluoromethyl)-2,3-dihydroimidazo[1,2-a]pyrimidin-5(1H)-one

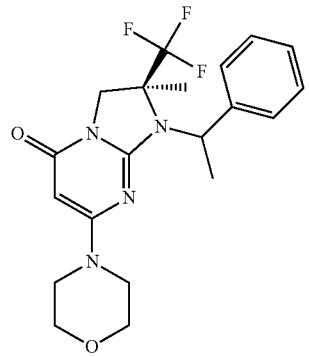 [SMILES: CC(c1ccccc1)N1c2nc(N3CCOCC3)cc(=O)n2C[C@@]1(C)C(F)(F)F]

Stage b:

The two diastereoisomers of (2S)-2-methyl-7-(morpholin-4-yl)-1-[(1R and 1S)-1-phenylethyl)-2-(trifluoromethyl)-2,3-dihydroimidazo[1,2-a]pyrimidin-5(1H)-one were separated by chiral chromatography using 60 mg of a 65/35 mixture of the two diastereoisomers:

Stationary phase: Chiralpak AD 20 μm 8×35 cm

Mobile phase: heptane (90%) EtOH (5% MeOH (5%).

16.4 mg of (2S)-2-methyl-7-(morpholin-4-yl)-1-[(1R or 1S)-1-phenylethyl)-2-(trifluoromethyl)-2,3-dihydroimidazo[1,2-a]pyrimidin-5(1H)-one are thus obtained, the characteristics of which are the following:

$^1$H NMR spectrum (400 MHz):

1.76 (s, 3 H); 1.82 (d, J=6.8 Hz, 3 H); 3.12 to 3.25 (m, 4 H); 3.37 to 3.55 (m, 4 H); 3.99 (d, J=12.5 Hz, 1 H); 4.17 (d, J=12.5 Hz, 1 H); 4.79 (s, 1 H); 4.87 (q, J=6.8 Hz, 1 H); 7.17 to 7.27 (t, J=7.5 Hz, 1 H); 7.32 (t, J=7.5 Hz, 2 H); 7.46 (d, J=7.5 Hz, 2 H)

Mass spectrometry: method B

Retention time Tr (min)=4.04

[M+H]+: m/z 409

Optical rotation: OR=+16.6+/−0.7; c=2.08 mg/0.5 ml DMSO.

Stage a: (2S)-2-Methyl-7-(morpholin-4-yl)-1-((1R and 1S)-1-phenylethyl)-2-(trifluoromethyl)-2,3-dihydroimidazo[1,2-a]pyrimidin-5(1H)-one The product can be prepared as described in stage d of Example 18, but using 500 mg of (2S)-2-methyl-7-(morpholin-4-yl)-2-(trifluoromethyl)-2,3-dihydroimidazo[1,2-a]pyrimidin-5(1H)-one, 1 g of caesium carbonate and 346 mg of (1-chloroethyl)benzene in 25 ml of acetonitrile. After purification by silica column chromatography (eluent: CH$_2$Cl$_2$/MeOH: 97/03), 60 mg of a 65/35 mixture of the two diastereoisomers of (2S)-2-methyl-7-(morpholin-4-yl)-1-((1R and 1S)-1-phenylethyl)-2-(trifluoromethyl)-2,3-dihydroimidazo[1,2-a]pyrimidin-5(1H)-one are obtained in the form of an orange powder, the characteristics of which are the following:

Mass spectrometry: method B

Retention time Tr (min)=4.00 and 4.04; mixture of isomers 2/3-1/3

[M+H]+: m/z 409.

EXAMPLE 32

(2S)-2-Methyl-7-(morpholin-4-yl)-1-[(1R or 1S)-1-phenylethyl]-2-(trifluoromethyl)-2,3-dihydroimidazo[1,2-a]pyrimidin-5(1H)-one

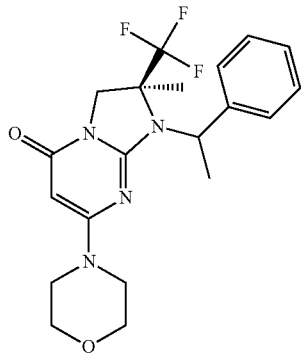 [SMILES: CC(c1ccccc1)N1c2nc(N3CCOCC3)cc(=O)n2C[C@@]1(C)C(F)(F)F]

The chiral separation described above, in stage b of Example 31, also gave 27.9 mg of the second diastereoisomer of (2S)-2-methyl-7-(morpholin-4-yl)-1-[(1R and 1S)-1-phenylethyl)-2-(trifluoromethyl)-2,3-dihydroimidazo[1,2-a]pyrimidin-5(1H)-one, the characteristics of which are the following:

$^1$H NMR spectrum (400 MHz):

1.76 (d, J=7.0 Hz, 3 H); 1.77 (s, 3 H); 3.17 to 3.25 (m, 4 H); 3.49 (m, 4 H); 3.96 (d, J=12.7 Hz, 1 H); 4.13 (d, J=12.7 Hz, 1 H); 4.85 (s, 1 H); 4.90 (q, J=7.0 Hz, 1 H); 7.20 (t, J=7.6 Hz, 1 H); 7.30 (t, J=7.6 Hz, 2 H); 7.42 (t, J=7.6 Hz, 2 H)

Mass spectrometry: method B
Retention time Tr (min)=4.00
[M+H]+: m/z 409
Optical rotation: OR=−95.7+/−1.6; c=951 mg/0.5 ml DMSO.

EXAMPLE 33

(2S)-1-(1H-indol-3-ylmethyl)-2-methyl-7-(morpholin-4-yl)-2-(trifluoromethyl)-2,3-dihydroimidazo[1,2-a]pyrimidin-5(1H)-one Stage c:

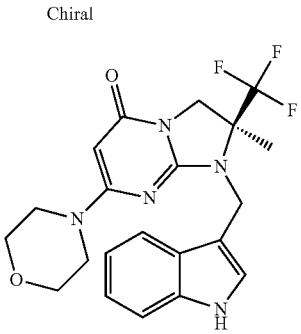 [SMILES: C[C@@]1(C(F)(F)F)Cn2c(nc(N3CCOCC3)cc2=O)N1Cc1c[nH]c2ccccc12]

1 ml of trifluoroacetic acid is added to a solution of 200 mg of 2-methylpropan-2-yl 3-{[(2S)-2-methyl-7-(morpholin-4-yl)-5-oxo-2-(trifluoromethyl)-2,3-dihydroimidazo[1,2-a]pyrimidin-1(5H)-yl]methyl}-1H-indole-1-carboxylate in 3 ml of methylene chloride. After an overnight period at a temperature in the region of 20° C., the reaction mixture is concentrated to dryness under reduced pressure. After purification by preparative LC MS (method D), the acetonitrile is concentrated and then the aqueous phase is extracted with ethyl acetate. The organic phase is successively washed with a saturated aqueous solution of sodium bicarbonate, twice with water and once with a saturated aqueous solution of sodium chloride. The resulting organic phase is dried over anhydrous magnesium sulphate, filtered and then concentrated to dryness under reduced pressure. The residue it taken up with water and then lyophilized. 75 mg of (2S)-1-(1H-indol-3-ylmethyl)-2-methyl-7-(morpholin-4-yl)-2-(trifluoromethyl)-2,3-dihydroimidazo[1,2-a]pyrimidin-5(1H)one are thus obtained in the form of a pinkish-coloured lyophilisate, the characteristics of which are the following:

$^1$H NMR spectrum (400 MHz):

1.54 (s, 3 H); 3.41 to 3.48 (m, 4 H); 3.57 to 3.64 (m, 4 H); 3.87 (d, J=12.5 Hz, 1 H); 4.11 (d, J=12.5 Hz, 1 H); 4.65 (d, J=16.1 Hz, 1 H); 4.90 (s, 1 H); 4.96 (d, J=16.1 Hz, 1 H); 6.97 (dt, J=1.0 and 8.1 Hz, 1 H); 7.08 (dt, J=1.0 and 8.1 Hz, 1 H); 7.32 to 7.39 (m, 2 H); 7.65 (broad d, J=8.1 Hz, 1 H); 10.97 (broad s, 1 H)

Mass spectrometry: method A
Retention time Tr (min)=0.91
[M+H]+: m/z 434;

Stage b: 2-Methylpropan-2-yl 3-{[(2S)-2-methyl-7-(morpholin-4-yl)-5-oxo-2-(trifluoromethyl)-2,3-dihydroimidazo[1,2-a]pyrimidin-1(5H)-yl]methyl}-1H-indole-1-carboxylate

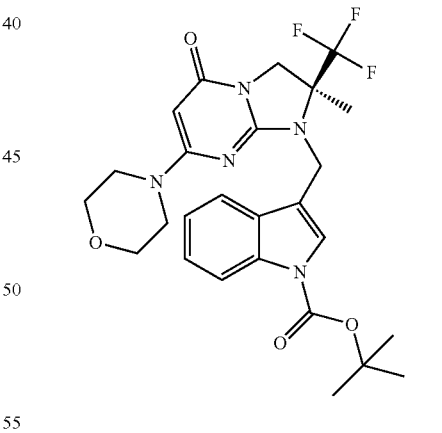

The product is prepared according to the procedure described in stage b of Example 30, but using 371 mg of 2-methylpropan-2-yl 3-{[7-chloro(2S)-2-methyl-5-oxo-2-(trifluoromethyl)-2,3-dihydroimidazo[1,2-a]pyrimidin-1(5H)-yl]methyl}-1H-indole-1-carboxylate, in 5 ml of morpholine. After microwave irradiation for 20 min at a temperature of 90° C., and purification by silica column chromatography of the reaction mixture (eluent: CH$_2$Cl$_2$/MeOH: gradient of 100/0 to 90/10), 200 mg of 2-methylpropan-2-yl 3-{[(2S)-2-methyl-7-(morpholin-4-yl)-5-oxo-2-(trifluoromethyl)-2,3-dihydroimidazo[1,2-a]pyrimidin-1(5H)-yl]methyl}-1H-indole-1-carboxylate are obtained, said product being used as it is in the next stage.

Stage a: 2-Methylpropan-2-yl 3-{[7-chloro-(2S)-2-methyl-5-oxo-2-(trifluoromethyl)-2,3-dihydroimidazo[1,2-a]pyrimidin-1(5H)-yl]methyl}-1H-indole-1-carboxylate

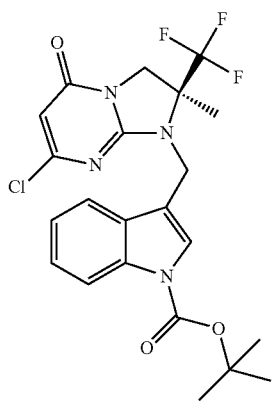 [SMILES: CC(C)(C)OC(=O)n1cc(CN2c3nc(Cl)cc(=O)n3C[C@@]2(C)C(F)(F)F)c2ccccc21]

The product can be prepared as described in stage a of Example 30, but using 204 mg of 7-chloro-(2S)-2-methyl-2-(trifluoromethyl)-2,3-dihydroimidazo[1,2-a]pyrimidin-5(1H)-one, 250 mg of 2-methylpropan-2-yl 3-(bromomethyl)-1H-indole-1-carboxylate and 525 mg of caesium carbonate, replacing the acetonitrile with dimethylformamide. After stirring for four days at a temperature in the region of 20° C., 370 mg of a mixture containing 2-methylpropan-2-yl 3-{[7-chloro-(2S)-2-methyl-5-oxo-2-(trifluoromethyl)-2,3-dihydroimidazo[1,2-a]pyrimidin-1(5H)-yl]methyl}-1H-indole-1-carboxylate are obtained, said product being used as it is in the next stage.

EXAMPLE 34

Synthesis of (2S)-1-[(2-chlorophenyl)carbonyl]-2-methyl-7-(morpholin-4-yl)-2-(trifluoromethyl)-2,3-dihydroimidazo[1,2-a]pyrimidin-5(1H)-one Chiral

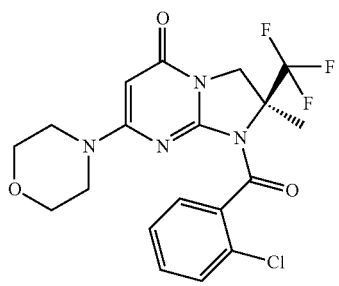

The product can be prepared as described in Example 21, but using 200 mg of (2S)-2-methyl-7-(morpholin-4-yl)-2-(trifluoromethyl)-2,3-dihydroimidazo[1,2-a]pyrimidin-5(1H)-one, 31 mg of sodium hydride at 60% in oil and 115 mg of 2-chlorobenzoyl chloride in 4 ml of tetrahydrofuran. After purification by silica column chromatography (eluent: dichloromethane/methanol: gradient of 100/0 to 97/03), 74 mg of (2S)-1-[(2-chlorophenyl)carbonyl]-2-methyl-7-(morpholin-4-yl)-2-(trifluoromethyl)-2,3-dihydroimidazo[1,2-a]pyrimidin-5(1H)-one are obtained in the form of an ivory-coloured foam, the characteristics of which are the following:
$^1$H NMR spectrum (400 MHz):
2.03 (s, 3 H); 2.70 to 2.93 (m, 4 H); 3.33 to 3.41 (m, 4 H); 4.07 (broad m, 1 H); 4.35 (d, J=12.7 Hz, 1 H); 5.04 (s, 1 H); 7.40 to 7.58 (m, 4 H)
Mass spectrometry: method A
Retention time Tr (min)=0.89
[M+H]+: m/z 443.

EXAMPLE 35

(2S)-2-Methyl-1-[(2-methylphenyl)carbonyl]-7-(morpholin-4-yl)-2-(trifluoromethyl)-2,3-dihydroimidazo[1,2-a]pyrimidin-5(1H)-one Chiral

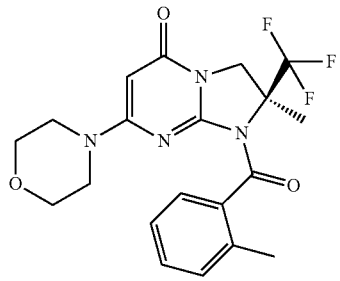

The product can be prepared as described in Example 21, but using 200 mg of (2S)-2-methyl-7-(morpholin-4-yl)-2-(trifluoromethyl)-2,3-dihydroimidazo[1,2-a]pyrimidin-5(1H)-one, 31 mg of sodium hydride at 60% in oil and 101 mg of 2-methylbenzoyl chloride in 4 ml of tetrahydrofuran. After purification by silica column chromatography (eluent: CH$_2$Cl$_2$/MeOH; gradient from 100/0 to 97/03), 44 mg of (2S)-2-methyl-1-[(2-methylphenyl)carbonyl]-7-(morpholin-4-yl)-2-(trifluoromethyl)-2,3-dihydroimidazo[1,2-a]pyrimidin-5(1H)one are obtained in the form of an ivory-coloured foam, the characteristics of which are the following:
$^1$H NMR spectrum (400 MHz):
2.03 (s, 3 H); 2.24 (s, 3 H); 2.70 to 2.90 (m, 4 H); 3.23 to 3.41 (m partially masked, 4 H); 4.04 (d, J=12.5 Hz, 1 H); 4.32 (d, J=12.5 Hz, 1 H); 5.00 (s, 1 H); 7.16 to 7.42 (m, 4 H)
Mass spectrometry: method B
Retention time Tr (min)=3.92
[M+H]+: m/z 423.

EXAMPLE 36

(2S)-1-[(1R or 1S)-1-(2-Fluorophenyl)ethyl]-2-methyl-7-(morpholin-4-yl)-2-(trifluoromethyl)-2,3-dihydroimidazo[1,2-a]pyrimidin-5(1H)-one Stage b:

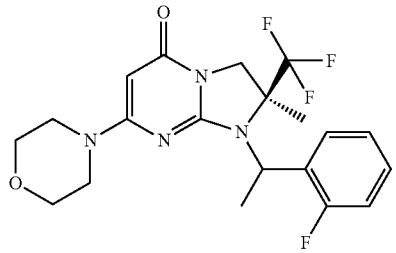 [SMILES: CC(c1ccccc1F)N1c2nc(N3CCOCC3)cc(=O)n2C[C@@]1(C)C(F)(F)F]

The two diastereoisomers of (2S)-1-[(1R and 1S)-1-(2-fluorophenyl)ethyl]-2-methyl-7-(morpholin-4-yl)-2-(trifluoromethyl)-2,3-dihydroimidazo[1,2-a]pyrimidin-5(1H)-one were separated by chiral chromatography using 89 mg of a mixture of the two diastereoisomers:

Stationary phase: Chiralpak AD 20 μm 8×35 cm

Mobile phase: heptane (85%) EtOH (15%).

51.2 mg of (2S)-1-[(1R or 1S)-1-(2-fluorophenyl)ethyl]-2-methyl-7-(morpholin-4-yl)-2-(trifluoromethyl)-2,3-dihydroimidazo[1,2-a]pyrimidin-5(1H)one are thus obtained in the form of a white foam, the characteristics of which are the following:

$^1$H NMR spectrum (500 MHz):

1.73 (s, 3 H); 1.81 (d, J=7.1 Hz, 3 H); 3.33 to 3.37 (m, 4 H); 3.58 (t, J=4.9 Hz, 4 H); 3.96 (d, J=12.7 Hz, 1 H); 4.13 (d, J=12.7 Hz, 1 H); 4.95 (s, 1 H); 5.03 (q, J=7.1 Hz, 1 H); 7.11 to 7.19 (m, 2 H); 7.23 to 7.34 (m, 1 H); 7.67 to 7.76 (m, 1 H)

Mass spectrometry: method A

Retention time Tr (min)=0.96

[M+H]+: m/z 427.

Stage a: (2S)-1-[(1R and 1S)-1-(2-Fluorophenyl)ethyl]-2-methyl-7-(morpholin-4-yl)-2-(trifluoromethyl)-2,3-dihydroimidazo[1,2-a]pyrimidin-5(1H)-one

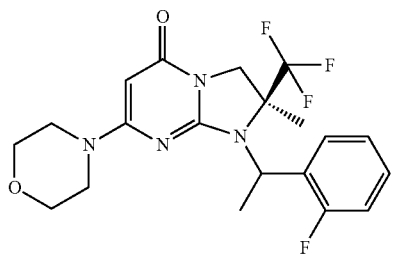

The product can be prepared as described in stage d of Example 18, but using 300 mg of (2S)-2-methyl-7-(morpholin-4-yl)-2-(trifluoromethyl)-2,3-dihydroimidazo[1,2-a]pyrimidin-5(1H)-one, 643 mg of caesium carbonate and 234 mg of 1-(1-chloroethyl)-2-fluorobenzene in 13 ml of acetonitrile. After purification by silica column chromatography (eluent: dichloromethane/methanol: 97/03), 89 mg of a 35/65 mixture of the two diastereoisomers of (2S)-1-[(1R and 1S)-1-(2-fluorophenyl)ethyl]-2-methyl-7-(morpholin-4-yl)-2-(trifluoromethyl)-2,3-dihydroimidazo[1,2-a]pyrimidin-5(1H) one are obtained in the form of a yellowy-white powder, the characteristics of which are the following:

Mass spectrometry: method A

Retention time Tr (min)=0.98 and 0.96: 35/65 mixture of the two diastereoisomers

[M+H]+: m/z 427.

EXAMPLE 37

(2S)-1-[(1R or 1S)-1-(2-Fluorophenyl)ethyl]-2-methyl-7-(morpholin-4-yl)-2-(trifluoromethyl)-2,3-dihydroimidazo[1,2-a]pyrimidin-5(1H)-one

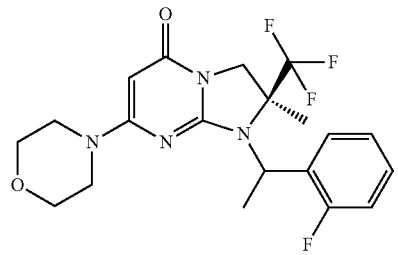 [SMILES: CC(c1ccccc1F)N1c2nc(N3CCOCC3)cc(=O)n2C[C@@]1(C)C(F)(F)F]

The chiral separation described above, in stage b of Example 36, also gave 26.8 mg of the second diastereoisomer of (2S)-1-[(1R and 1S)-1-(2-fluorophenyl)ethyl]-2-methyl-7-(morpholin-4-yl)-2-(trifluoromethyl)-2,3-dihydroimidazo[1,2-a]pyrimidin-5(1H)-one, the characteristics of which are the following:

$^1$H NMR spectrum (500 MHz):

1.64 (s, 3 H); 1.84 (d, J=7.0 Hz, 3 H); 3.25 to 3.38 (m partially masked, 4 H); 3.50 to 3.63 (m, 4 H); 3.91 (d, J=12.7 Hz, 1 H); 4.16 (d, J=12.7 Hz, 1 H); 4.86 (s, 1 H); 5.06 (q, J=7.0 Hz, 1 H); 7.14 to 7.22 (m, 2 H); 7.30 to 7.38 (m, 1 H); 7.71 (m, 1 H)

Mass spectrometry: method A

Retention time Tr (min)=0.98

[M+H]+: m/z 427.

EXAMPLE 38

Pharmaceutical Composition

Tablets corresponding to the following formulation were prepared:

| | |
|---|---|
| Product of Example 1 | 0.2 g |
| Excipient for a tablet having a final weight of (details of the excipient: lactose, talc, starch, magnesium stearate). | 1 g |

Example 1 is taken by way of example of a pharmaceutical preparation, it being possible for this preparation to be carried out, if desired, with other products of formula (I) according to the present invention, and in particular given in examples in the present application, among Examples 2 to 37 and 39 to 43.

The products of the table below, which are products of formula (I) as defined above, constitute Examples 39 to 43 of the present invention. These products of Examples 39 to 43 are prepared as indicated above in the experimental section and are characterized by the physiochemical results given in this table.

| | | Mass spectrometry: Method E | |
|---|---|---|---|
| Example | Name | Tr(min) | [M + H]+: m/z |
| Example 39 | (S)-1-[2-(2-fluoro-4,5-dimethoxyphenyl)-2-hydroxyethyl]-2-methyl-7-morpholin-4-yl-2-trifluoromethyl-2,3-dihydro-1H-imidazo[1,2-a]pyrimidin-5-one | 0.69 | m/z 503 |

| Example | Name | Mass spectrometry: Method E | |
|---------|------|--------|----------|
| | | Tr(min) | [M + H]+: m/z |
| Example 40 | (S)-1-[(S)-2-hydroxy-2-(2-methoxy-phenyl)ethyl]-2-methyl-7-morpholin-4-yl-2-trifluoromethyl-2,3-dihydro-1H-imidazo[1,2-a]pyrimidin-5-one | 0.74 | m/z 455 |
| Example 41 | (S)-1-[(S)-2-(4-chloro-2-methoxyphenyl)-2-hydroxyethyl]-2-methyl-7-morpholin-4-yl-2-trifluoromethyl-2,3-dihydro-1H-imidazo[1,2-a]pyrimidin-5-one | 0.80 | m/z 489 |
| Example 42 | (S)-1-[(S)-2-(4-fluoro-2-methoxyphenyl)-2-hydroxyethyl]-2-methyl-7-morpholin-4-yl-2-trifluoromethyl-2,3-dihydro-1H-imidazo[1,2-a]pyrimidin-5-one | 0.76 | m/z 473 |
| Example 43 | (S)-1-[(S)-2-(2-chloro-4-methoxyphenyl)-2-hydroxyethyl]-2-methyl-7-morpholin-4-yl-2-trifluoromethyl-2,3-dihydro-1H-imidazo[1,2-a]pyrimidin-5-one | 0.77 | m/z 489 |

Pharmacological Section:
Experimental Protocols
In Vitro Experimental Procedures The inhibitory activity of the molecules on AKT phosphorylation is measured either by western blotting using the technique described below, or by the MSD Multi-spot Biomarker detection technique from Meso Scale Discovery also described below. It was demonstrated, on one set of molecules, that both techniques give compatible results.

Study of pAKT Expression in PC3 Human Prostate Carcinoma Cells Measured by Western Blotting (test A):

This test is based on measuring the expression of the AKT protein phosphorylated on serine 473. The phosphorylation of AKT (pAKT) is measured by western blotting in the PC3 human prostate carcinoma line (ATCC CRL-1435), using an antibody that specifically recognises pAKT-S473.

On day 1, the PC3 cells are seeded into 6-well plates (TPP, #92006) at the concentration of $0.8 \times 10^6$ cells/well in 1800 µl of DMEM medium (DMEM Gibco #11960-044) containing 10% of foetal calf serum (SVF Gibco, #10500-056) and 1% glutamine (L-Glu Gibco #25030-024), and incubated at 37° C., 5% $CO_2$, overnight.

On day 2, the cells are incubated in the presence or absence of the test products for 1 to 2 hours at 37° C. in the presence of 5% $CO_2$. The molecules, diluted in dimethyl sulphoxide (DMSO Sigma #D2650), are added from a 10-times concentrated stock solution, the final percentage of DMSO being 0.1%. The molecules are tested either at a single concentration of less than or equal to 10 µM, or at increasing concentrations in a range that can extend from less than 1 nM to 10 µM.

After this incubation, the cells are lysed for the preparation of the proteins. After the culture medium has been drawn off, the cells are rinsed with 1 ml of PBS (DPBS Gibco, #14190-094), recovered by scraping in 200 µl of complete HNTG buffer and transferred into a 96-well plate (Greiner #651201), and lysed for 1 h on ice. The HNTG buffer is composed of the following mixture: 50 mM hepes, 150 mM NaCl, 1% triton, 10% glycerol, with extemporaneous addition of one Mini Protease Inhibitor Cocktail tablet (Roche 1836153) and of one Phosphatase Inhibitor Cocktail tablet (Roche104906837001) per 10 ml of buffer.

The lysate is centrifuged for 10 min at 6000 rpm. 155 µl of supernatant are recovered. 150 µl are incubated for denaturation for 5 min at 95° C. in the presence of 4× NuPAGE LDS Sample Buffer diluted 4-fold (InVitrogen ref NP0007) and of 10× NuPAGE Sample Reducing Agent diluted 10-fold (InVitrogen ref NP0009). These samples are then frozen at −20° C. 5 µl are assayed by the microBCA technique according to the technical bulletin of the MicroBCA Protein Assay Kit (Pierce #23235).

For protein separation, 20 µg of proteins are loaded on to a NU-PAGE 4-12% Bis Tris Gel 12 well (InVitrogen ref NP0322BOX) and the migration is carried out for 1 h 30 in 20× NU-PAGE MOPS SDS Running Buffer diluted 20-fold (InVitrogen ref NP0001), at 150 volts.

The gel is then transferred on to an Invitrolon PVDF membrane (Invitrogen #LC2007) permeabilised before and after a few seconds in ethanol (Ethanol Fischer Scientific #E/0600DF/15).

The transfer is carried out in a Biorad tank at 30 volts overnight or at 60 volts for 3 hours, in the presence of 20× NUPAGE Transfer Buffer diluted 20-fold (InVitrogen ref NP0006).

The membrane is then saturated in saturating solution composed of TBS (10× Tris Buffered Saline, Sigma #T5912, diluted 10-fold), 0.1% Tween 20 (Sigma #P5927) and 3% BSA (Bovine Albumin Serum Fraction V, Sigma #A4503) for 6 h after overnight transfer or else for 1 h after transfer for a period of 3 h.

The primary antibodies are diluted to 1/1000 for the anti-phospho AKT-Ser473 antibody (1931-12, rabbit monoclonal, cat#4058 from Cell Signaling Technology Abcam), in saturating solution composed of PBS, 0.1% Tween 20 and 3% BSA, and then shaken overnight at 4° C.

Two rinses for 5 min in washing solution composed of TBS and 0.1% Tween 20 are carried out before hybridisation of the secondary antibodies.

The secondary antibodies are diluted 1/10000 for the rabbit anti-Mouse IgG HRP antibody (W402 Promega) and to 1/10000 for the goat anti-Rabbit IgG HRP antibody (W401 Promega) in saturating solution, and then shaken for 1 h at ambient temperature.

Two rinses for 30 min in washing solution are carried out and then a rinse for 5 min in $H_2O$ is carried out in order to eliminate the remaining Tween 20.

The revealing solution is prepared volume-for-volume according to the technical bulletin of the Western Lightning Chemiluminescence Reagent Plus (Western Lightning Chemiluminescence Reagent Plus Perkin Elmer #NEL104).

The membrane is placed in the revealing solution for 1 min, drained, inserted between two transparent plates and then placed in the measuring device for reading the luminescence and the quantification of the signal. The luminescence is read with the FujiFilm device (Ray Test).

The FUJI device measures the total luminescence signal obtained (AU) for each band selected. It then subtracts the background noise (BG) proportional to the size of the band selected (Area), said background noise being calculated from a specific background noise band, with a view to obtaining the specific signal (AU-BG) for each band. The band obtained in the absence of product and in the presence of 0.1% DMSO is considered to be the 100% signal. The software calculates the % specific activity (Ratio) obtained for each band selected as a function of this 100% signal. The percentage inhibition is calculated for each concentration according to the formula (100%−Ratio).

Two independent experiments make it possible to calculate the mean of the percentages of inhibition obtained at a given concentration for the products tested only at one concentration.

Where appropriate, the activity of the products is translated into approximately IC50, obtained from a dose-response curve of various concentrations tested and representing the dose giving 50% of specific inhibition (absolute IC50). Two independent experiments make it possible to calculate the mean of the IC50s.

Study of pAKT Expression in PC3 Human Prostate Carcinoma Cells Measured by the MSD Multi-Spot Biomarker Detection Technique from Meso Scale Discovery (Test B):

This test is based on measuring the expression of the AKT protein phosphorylated on serine 473 (P-AKT-S473), in the PC3 human prostate carcinoma line, by means of the technique based on a sandwich immunoassay using the MSD Multi-spot Biomarker Detection kit from Meso Scale Discovery: phospho-Akt (Ser473) whole cell lysate kit (#K151CAD) or phospho-Akt (Ser473)/Total Akt whole cell lysate kit (#K151OOD). The primary antibody specific for P-AKT-S473 (Kit #K151CAD) is coated onto an electrode in each well of the 96-well plates of the MSD kit: after the addition of a protein lysate to each well, the signal is visualised by adding a secondary detection antibody labelled with an electrochemoluminescent compound. The procedure followed is that described in the kit.

On day 1, the PC3 cells are seeded into 96-well plates (TPP, #92096) at the concentration of 35 000 cells/well in 200 µl of DMEM medium (DMEM Gibco #11960-044) containing 10% of foetal calf serum (FCS Gibco, #10500-056) and 1% glutamine (L-Glu Gibco #25030-024), and incubated at 37° C., 5% $CO_2$, overnight.

On day 2, the cells are incubated in the presence or absence of the test products for 1 to 2 h at 37° C. in the presence of 5% of $CO_2$. The molecules, diluted in dimethyl sulphoxide (DMSO Sigma #D2650), are added from a 20-times concentrated stock solution, the final percentage of DMSO being 0.1%. The molecules are tested either at a single concentration of less than or equal to 10 µM, or at increasing concentrations in a range that can extend from less than 1 nM to 10 µM.

After this incubation, the cells are lysed for the preparation of the proteins. For this, after the culture medium has been drawn off, 50 µl of complete Tris Lysis Buffer of the MSD kit containing the protease and phosphatase inhibitor solutions are added to the wells and the cells are lysed for 1 h at 4° C. with shaking. At this stage, the plates containing the lysates can be stored at −20° C. or at −80° C.

The wells of the 96-well plates of the MSD kit are saturated for 1 h at ambient temperature with the blocking solution of the MSD kit. Four washes are carried out with 150 µl of Tris Wash Buffer of the MSD kit. The lysates previously prepared are transferred into the 96-well multi-spot plates of the MSD kit and incubated for 1 h at ambient temperature, with shaking. Four washes are carried out with 150 µl of Tris Wash Buffer of the MSD kit. 25 µl of the MSD sulfo-tag detection antibody solution are added to the wells and incubated for 1 h at ambient temperature, with shaking. Four washes are carried out with 150 µl of Tris Wash Buffer of the MSD kit. 150 µl of Read Buffer of the MSD kit are added to the wells and the plates are read immediately on the S12400 instrument from Meso Scale Discovery.

The instrument measures a signal for each well. Wells without cells and containing the lysis buffer serve to determine the background noise that will be subtracted from all the measurements (min). The wells containing cells in the absence of product and in the presence of 0.1% DMSO are considered to be the 100% signal (max). The percentage inhibition is calculated for each concentration of test product according to the following formula: (1-((test−min)/(max−min)))×100.

The activity of the product is translated to $IC_{50}$, obtained from a dose-response curve of the various concentrations tested and representing the dose giving 50% specific inhibition (absolute $IC_{50}$). 2 independent experiments make it possible to calculate the mean of the $IC_{50}$ values.

Inhibitory activity of the molecules on autophagy is measured by means of the translocation of the LC3 protein from the cytoplasm to the autophagosomes. For this, Hela cells were transfected with a vector encoding the chimeric protein GFP-LC3. A Hela clone stably expressing the GFP-LC3 protein was selected. The translocation of the LC3 protein is determined by measuring the number of cells exhibiting LC3 granulations after a metabolic stress, using an iCyte automatic image analysis cytometer (Compucyte).

Study of the Translocation of the LC3 Protein in Hela Human Cells, Measured by Image Analysis Cytometry (Test C):

On day 1, the Hela GFP-LC3 cells are seeded into 96-well plates coated with poly-D-lysine (Greiner, #655946) at the concentration of 15000 cells/well in 200 µl of DMEM medium (DMEM Gibco #11960-044) containing 10% of foetal calf serum (FCS Gibco, #10500-056) and 1% glutamine (L-Glu Gibco #25030-024), and incubated at 37° C., 5% $CO_2$, overnight.

On day 2, the cells are washed twice with EBSS (Sigma #E3024). The cells are then incubated in EBSS, 10 µM hydroxychloroquine and test products, for 2 hours at 37° C. in the presence of 5% $CO_2$. The molecules are diluted in dimethyl sulphoxide (DMSO Sigma #D2650), the final DMSO percentage being 0.1%. The molecules are tested at increasing concentrations in a range that can extend from 10 nM to 1 µM.

After this incubation, the cells are fixed with 4% paraformaldehyde (Sigma #HT501128 4L) for 10 min. The cells are then washed twice with PBS and the nuclei then stained with 2 µg/ml of Hoechst 33342 (Invitrogen #H3570). The 96-well plates are then read with the iCyte image analysis cytometer (Compucyte). The analyser quantifies the number of cells exhibiting LC3 granulations. A cell is considered to be positive when it exhibits at least 4 LC3 granulations. The percentage of cells exhibiting more than 4 granulations is calculated relative to the total number of cells.

The activity of the product is translated to $IC_{50}$, obtained from a dose-response curve of various concentrations tested and representing the dose giving 50% specific inhibition (absolute $IC_{50}$). 2 independent experiments make it possible to calculate the mean of the $IC_{50}$ values.

The results obtained for the products as examples in the experimental section are given in the pharmacological results table below:

Pharmacological results table 1:

| Example | Test A* | Test B* | Test C* |
|---|---|---|---|
| Example 1 | 100 | 3 | 44 |
| Example 2 | 324 | | 145 |
| Example 3 | 634 | | 493 |
| Example 4 | 25 | | 107 |
| Example 5 | 30 | | 73 |
| Example 6 | 1644 | | 81 |
| Example 7 | | | 71 |
| Example 8 | 15 | | 13 |
| Example 9 | | | 191 |
| Example 10 | 16 | | 31 |
| Example 11 | | | 235 |
| Example 12 | 77 | | 194 |
| Example 13 | | | 822 |
| Example 14 | 174 | | 10000 |
| Example 15 | 121 | | 72 |
| Example 16 | 79 | | |
| Example 17 | | | 345 |
| Example 18 | | | 39 |
| Example 19 | | 26 | 425 |
| Example 20 | | 18 | 703 |
| Example 21 | | 7 | >1000 |
| Example 22 | | 59 | 872 |
| Example 23 | | | 2116 |
| Example 24 | | 13 | 314 |
| Example 25 | | 28 | 621 |
| Example 26 | | 16 | |
| Example 27 | | 24 | 51 |
| Example 28 | | 10 | 198 |
| Example 29 | | 6 | 261 |
| Example 30 | | 89 | >1000 |
| Example 31 | | 60 | 334 |
| Example 32 | | 22 | >1000 |
| Example 33 | | 42 | 461 |
| Example 34 | | 159 | 1000 |
| Example 35 | | 32 | >1000 |
| Example 36 | | 4 | 995 |
| Example 37 | | 19 | 737 |

*Tests A, B and C: $IC_{50}$ (nM)

Antimalarial Activity Test

The antimalarial activity tests are carried out according to the radioactive micromethod of Desjardins (R. E. Desjardins, C. J. Canfield, J. D. Haynes, J. D. Chulay, Antimicrob. Agents Chemother., 1979, 16, 710-718). The assays are carried out in 96-well microplates (Test Plates Ref. 92696, Techno Plastic Products Ag, Zollstrasse 155, CH-8219 Trasadingen). The *P. falciparum* strains are cultured in solutions of RPMI 1640 supplemented with 5% of human serum with a haematocrit at 2% and a blood parasite concentration at 1.5%. For each assay, the parasites are incubated with selected concentrations of drugs for 48 h at 37° C. in a humid atmosphere and at 5% $CO_2$. Artemisinin, artesunate and also chloroquine diphosphate are used as reference molecules. The first dilution of the drug is prepared at 1 mg/ml in dimethyl sulphoxide. The range of dilutions of the successive daughter solutions is also prepared in dimethyl sulphoxide. Each daughter dilution is subsequently diluted to 1/50 in RPMI 1640 supplemented with 5% of human serum, all the dilutions being carried out at 37° C. These dilutions are then added to the parasites in culture in the microplates. After addition of the drug, the parasites are in culture in RPMI 1640 containing 5% of human serum and 1% of dimethyl sulphoxide. The parasite growth is measured by incorporation of tritiated hypoxanthine (added 24 h after the beginning of the exposure to the drug) compared with the incorporation in the absence of drug.

The activity of the product is translated to % inhibition of the growth of *P. falciparum* (highly chloroquine-resistant strain Fcm29-Cameroon) at 1 µM and 0.1 µM in an in vitro test using infected human erythrocytes.

The results obtained for the products as examples in the experimental section are given in pharmacological results table 2 below:

Pharmacological results table 2:

| Example | *P. falciparum* % inhibition 1 µM | *P. falciparum* % inhibition 0.1 µM |
|---|---|---|
| Example 1 | 93 | 67 |
| Example 3 | 95 | 15 |
| Example 4 | 97 | 54 |
| Example 10 | 97 | 38 |
| Example 11 | 13 | / |
| Example 15 | 101 | 39 |
| Example 26 | 75 | 14 |
| Example 27 | 53 | / |
| Example 28 | 53 | 14 |
| Example 29 | 52 | / |
| Example 39 | 85 | 39 |
| Example 40 | 80 | 20 |
| Example 41 | 78 | / |
| Example 42 | 78 | / |
| Example 43 | 74 | 22 |

The invention claimed is:
1. A product of formula (I):

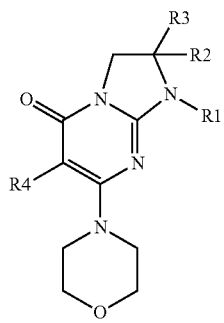

in which:
R1 represents an -L-aryl or -L-heteroaryl radical, such that L represents:
either a linear or branched alkyl radical containing from 1 to 6 carbon atoms and optionally substituted with a hydroxyl radical,
or a CO group,
or an L'X group where L' represents a linear or branched alkyl radical containing from 1 to 6 carbon atoms, and X an oxygen or sulphur atom;
the aryl and heteroaryl radicals being optionally substituted with one or more radicals, which may be identical or different, chosen from halogen atoms and hydroxyl, CN, nitro-, —COOH,—COOalk, —NRxRy, —CONRxRy, —NRxCORy, —NRxCO$_2$Rz, —CORy, alkoxy, phenoxy, alkylthio, alkyl, cycloalkyl and heterocycloalkyl radicals, wherein the alkoxy, phenoxy, alkylthio, alkyl and heterocycloalkyl are optionally substituted with one or more radicals, which may be identical or different, chosen from halogen atoms, and NRvRw and wherein the heterocycloalkyl and heteroaryl radicals optionally additionally contain an oxo radical;

R2 represents a hydrogen atom or an alkyl radical;

R3 represents an alkyl radical optionally substituted with one or more halogen atoms;

R4 represents a hydrogen atom or a halogen atom;

NRxRy being such that Rx represents a hydrogen atom or an alkyl radical and Ry represents a hydrogen atom or a cycloalkyl radical or an alkyl radical optionally substituted with one or more radicals, which may be identical or different, chosen from hydroxyl, alkoxy, NRvRw and heterocycloalkyl radicals; or Rx and Ry form, with the nitrogen atom to which they are attached, a cyclic radical containing from 3 to 10 ring members and optionally one or more other heteroatoms chosen from O, S, NH and N-alkyl, this cyclic radical being optionally substituted;

NRvRw being such that Rv represents a hydrogen atom or an alkyl radical and Rw represents a hydrogen atom or a cycloalkyl radical or an alkyl radical optionally substituted with one or more radicals, which may be identical or different, chosen from hydroxyl, alkoxy and heterocycloalkyl radicals; or Rv and Rw form, with the nitrogen atom to which they are attached, a cyclic radical containing from 3 to 10 ring members and optionally one or more other heteroatoms chosen from O, S, NH and N-alkyl, this cyclic radical being optionally substituted;

the cyclic radicals that Rx and Ry or Rv and Rw, respectively, can form with the nitrogen atom to which they are attached, being optionally substituted with one or more radicals, which may be identical or different, chosen from halogen atoms, and alkyl, hydroxyl, oxo, alkoxy, NH2, NH(alkyl) and N(alkyl)2 radicals;

Rz represents the values of Ry except for hydrogen;

Rx, Ry and Rz, in the —NRxCORy, —CORy and NRxCO2Rz radicals, being chosen from the meanings indicated above for Rx, Ry and Rz;

all the above alkyl alkoxy and alkylthio radicals being linear or branched and containing from 1 to 6 carbon atoms, racemic, enantiomeric and diastereoisomeric isomers, and pharmaceutically acceptable salts thereof.

2. The product of claim 1, in which:

R1 represents an -L-phenyl or -L-heteroaryl radical, such that L represents:

either a linear or branched alkyl radical containing from 1 to 6 carbon atoms and optionally substituted with a hydroxyl radical, or a CO group, or an L'-X group, where L' represents a linear or branched alkyl radical containing from 1 to 6 carbon atoms, and X an oxygen or sulphur atom;

the phenyl and heteroaryl radicals being optionally substituted with one or more radicals, which may be identical or different, chosen from halogen atoms and —NRxRy, alkoxy and alkyl radicals, wherein the alkoxy and alkyl radicals are optionally substituted with one or more radicals chosen from halogen atoms;

R2 represents an alkyl radical;

R3 represents an alkyl radical optionally substituted with one or more halogen atoms;

R4 represents a hydrogen atom or a fluorine atom;

NRxRy being such that Rx represents a hydrogen atom or an alkyl radical and Ry represents a hydrogen atom or an alkyl radical; or Rx and Ry form, with the nitrogen atom to which they are attached, a morpholino radical;

all the above alkyl or alkoxy radicals being linear or branched and containing from 1 to 6 carbon atoms, racemic, enantiomeric and diastereoisomeric isomers, and pharmaceutically acceptable salts thereof.

3. The product according to claim 1, corresponding to the following formulae:

(2S)-1-[2-(4-methoxyphenypethyl]-2-methyl-7-(morpholin-4-yl)-2-(trifluoromethyl)-2,3-dihydroimidazo[1,2-a]pyrimidin-5(1H)one 1-[2-(4-methoxyphenyeethyl]-2-methyl-7-(morpholin-4-yl)-2-(trifluoromethyl)-2,3-dihydroimidazo[1,2-a]pyrimidin-5(1H)one (2S)-1-benzyl-2-methyl-7-(morpholin-4-yl)-2-(trifluoromethyl)-2,3-dihydroimidazo [1,2-a]lpyrimidin-5 (1H)one (2 S)-2-methyl-7-(morpholin-4-yl)- 1 -(2-phenylethyl)-2-(trifluoromethyl)-2,3 -dihydroimidazo [1 ,2-a]pyrimidin-5(1H)one (2 S)-2-methyl-7-(morpholin-4-yl)- 1 -(3 -phenylpropyl)-2-(trifluoromethyl)-2,3 -dihydroimidazo [1 ,2-a]pyrimidin-5(1H)one (2 S)-2-methyl-7-(morpholin-4-yl)- 1 -(2-phenoxyethyl)-2-(trifluoromethyl)-2,3-dihydroimidazo [1,2-a]pyrimidin- 5 (1H)one (2S)-2-methyl-7-(morpholin-4-ye- 1- [2-(phenylsulphanypethyl]-2-(trifluoromethyl)-2,3 -dihydroimidazo [1 ,2-a]pyrimidin-5 (1H)one (2 S)-2-methyl-7-(morpholin-4-yl)- 1 - [(2R)-2-phenylpropyl] -2-(trifluoromethyl)-2,3 -dihydroimidazo [1,2-a]pyrimidin-5(1H)one (2S)-2-methyl-7-(morpholin-4-yl)- 1- [(2S)-2-phenylpropyl]-2-(trifluoromethyl)-2,3 -dihydroimidazo [1,2-a] pyrimidin-5 (1H)one (2 S)- 1 - [(2S)-2-hydroxy-2-phenylethyl]-2-methyl-7-(morpholin-4-ye-2-(trifluoromethyl)-2,3 -dihydroimidazo [1,2-a] pyrimidin-5 (1H)one (2 S)- 1 - [(2R)-2-hydroxy-2-phenylethyl]-2-methyl-7-(morpholin-4-yl)-2-(trifluoromethyl)-2,3-dihydroimidazo [1 ,2-a]pyrimidin-5(1H)one (2S)-2-methyl-7-(morpholin-4-yl)- 1- [(2S)- 1 -phenylpropan-2-yl] -2-(trifluoromethyl)-2,3 -dihydroimidazo [1,2-a]pyrimidin-5(1H)one (2S)-2-methyl-7-(morpholin-4-yl)- 1- [(1 S)- 1 -phenylpropyl]-2-(trifluoromethyl)-2,3 -dihydroimidazo [1 ,2-a]pyrimidin-5(1H)one (2 S)-2-methyl-7-(morpholin-4-yl)- 1 - [(1R)- 1 -phenylpropyl]-2-(trifluoromethyl)-2,3 -dihydroimidazo [1 ,2-a]pyrimidin- 5 (1H)one (2 S)-2-methyl-7 -(morpholin-4-yl)- 1- {2- [4-(morpholin-4-yl)phenyl] ethyl}-2-(trifluoromethyl)-2,3 -dihydroimidazo [1 ,2-a]pyrimidin-5(1H)one (2S)-2-methyl-7-(morpholin-4-yl)- 1 -(1 -phenylethyl)-2-(trifluoromethyl)-2,3 -dihydroimidazo [1 ,2-a]pyrimidin-5(1H)one 1- [2-(4-methoxyphenyl)ethyl]-2,2-dimethyl-7-(morpholin-4-yl)-2,3-dihydroimidazo [1,2-a]pyrimidin-5 (1H)one (2S)-6-fluoro- 1 - [2-(4-methoxyphenyeethyl] -2-methyl-7-(morpholin-4-yl)-2-(trifluoromethyl)-2,3 -dihydroimidazo [1,2-a]pyrimidin-5(1H)one (2S)- 1 -benzyl-6-fluoro-2-methyl-7-(morpholin-4-yl)-2-(trifluoromethyl)-2,3 -di -hydroimidazo [1,2-a]pyrimidin-5(1H)one (2S)-1-[(5-chloro-1-benzothiophen-3-yl)methyl]-2-methyl-7-(morpholin-4-yl)-2-(trifluoromethyl)-2,3-dihydroimidazo[1,2-a]pyrimidin-5(1H)one (2S)-2-methyl-7-(morpholin-4-yl)-1-(phenylcarbonyl)-2-(trifluoromethyl)-2,3-dihydroimidazo[1,2-a]pyrimidin-5(1H)one (2S)-1-[(1R or 1S)-1-(3-fluorophenypethyl]-2-methyl-7-(morpholin-4-yl)-2-(trifluoromethyl)-2,3-dihydroimidazo[1,2-a]pyrimidin-5(1H)one (2S)-1-{[4-chloro-2-(trifluoromethy)quinolin-6-yl]methyl}-2-methyl-7-(morpholin-4-yl)-2-(trifluoromethyl)-2,3-dihydroimidazo[1,2-a]pyrimidin-5(1H)one trifluoroacetate (2S)-1-(3-bromo-4-fluorobenzyl)-2-methyl-7-(morpholin-4-yl)-2-(trifluoromethyl)-2,3-dihydroimidazo[1,2-a]pyrimidin-5(1H)one (2S)-1-(2,3-difluorobenzyl)-2-methyl-7-(morpholin-4-yl)-2-(trifluoromethyl)-2,3-dihydroimidazo[1,2-a]pyrimidin-5(1H)one (2S)-1-[2-(3-methoxyphenypethyl]-2-methyl-7-(morpholin-4-yl)-2-(trifluoromethyl)-2,3-dihydroimidazo[1,2-a]pyrimidin-5(1H)one (2S)-1-[2-(2-chlorophenyl)ethyl]-2-methyl-7-(morpholin-4-yl)-2-(trifluoromethyl)-2,3-dihydroimidazo[1,2-a]pyrimidin-5(1H)one (2S)-1-[2-(4-chlorophenypethyl]-2-methyl-7-(morpholin-4-yl)-2-(trifluoromethyl)-2,3-dihydroimidazo[1,2-a]pyrimidin-5(1H)one (2S)-1-[2-(3-chlorophenyl)ethyl]-2-methyl-7-(morpholin-4-yl)-2-(trifluoromethyl)-2,3-dihydroimidazo[1,2-a]pyrimidin-5(1H)one (2S)-141,3-benzoxazol-2-ylmethyl]-2-methyl-7-(morpholin-4-yl)-2-(trifluoromethyl)-2,3-dihydroimidazo[1,2-a]pyrimidin-5(1H)one (2S)-2-methyl-7-(morpholin-4-yl)-1-[(1R or 1S)-1-phenylethyl]-2-(trifluoromethyl)-2,3-dihydroimidazo[1,2-a]pyrimidin-5(1H)one (2S)-2-methyl-7-(morpholin-4-yl)-1-[(1R or 1S)-1-phenylethyl]-2-(trifluoromethyl)-2,3-dihydroimidazo[1,2-a]pyrimidin-5(1H)one (2S)-1-(1H-indol-3-ylmethyl)-2-methyl-7-(morpholin-4-yl)-2-(trifluoromethyl)-2,3-dihydroimidazo[1,2-a]pyrimidin-5(1H)one (2S)-1-[(2-chlorophenyl)carbonyl]-2-methyl-7-(morpholin-4-yl)-2-(trifluoromethyl)-2,3-dihydroimidazo[1,2-a]pyrimidin-5(1H)one (2S)-2-methyl-1-[(2-methylphenyl)carbonyl]-7-(morpholin-4-yl)-2-(trifluoromethyl)-2,3-dihydroimidazo[1,2-a]pyrimidin-5(1H)one (2S)-1-[(1R or 1S)-1-(2-fluorophenypethyl]-2-methyl-7-(morpholin-4-yl)-2-(trifluoromethyl)-2,3-dihydroimidazo[1,2-a]pyrimidin-5(1H)one (2S)-1-[(1R or 1S)-1-(2-fluorophenypethyl]-2-methyl-7-(morpholin-4-yl)-2-(trifluoromethyl)-2,3-dihydroimidazo[1,2-a]pyrimidin-5(1H)one (S)-1-[2-(2-fluoro-4,5-dimethoxyphenyl)-2-hydroxyethyl]-2-methyl-7-morpholin-4-yl-2-trifluoromethyl-2,3-dihydro-1H-imidazo[1,2-a]pyrimidin-5-one (S)-1-[(S)-2-hydroxy-2-(2-methoxyphenypethyl]-2-methyl-7-morpholin-4-yl-2-trifluoromethyl-2,3-dihydro-1 1-imidazo[1,2-a]pyrimidin-5-one (S)-1-[(S)-2-(4-chloro-2-methoxyphenyl)-2-hydroxyethyl]-2-methyl-7-morpholin-4-yl-2-trifluoromethyl-2,3-dihydro-1H-imidazo[1,2-a]pyrimidin-5-one (S)-1-[(S)-2-(4-fluoro-2-methoxyphenyl)-2-hydroxyethyl]-2-methyl-7-morpholin-4-yl-2-trifluoromethyl-2,3-dihydro-1H-imidazo[1,2-a]pyrimidin-5-one (S)-1-[(S)-2-(2-chloro-4-methoxyphenyl)-2-hydroxyethyl]-2-methyl-7-morpholin-4-yl-2-trifluoromethyl-2,3-dihydro-1H-imidazo[1,2-a]pyrimidin-5-one and pharmaceutically acceptable salts thereof.

4. A pharmaceutical composition comprising the product of claim 1 and pharmaceutically acceptable salts thereof.

5. A pharmaceutical composition comprising the product of claim 3, and pharmaceutically acceptable salts thereof.

6. A pharmaceutical composition containing, as active ingredient, at least one product according to claim 1, or a pharmaceutically acceptable salt of said product, and a pharmaceutically acceptable carrier.

7. A method of treating cancers, capable of being modulated by inhibition of the PI3K/AKT/mTOR pathway, in a patent in need thereof comprising administering to said patient a therapeutically effective amount of the product according to claim 1.

8. The method according to claim 7, wherein solid or liquid tumours are treated.

9. The method according to claim 7 wherein said cancers are resistant to cytotoxic agents.

10. The method according to claim 7, comprising treating of primary tumours and/or metastases, in particular in gastric, hepaptic, renal, ovarian, colon, prostate, endometrial and lung (NSCLC and SCLC) cancers, glioblastomas, thyroid, bladder and breast cancers, in melanoma, in lymphoid or myeloid haematopoietic tumours, in sarcomas, in brain, larynx and lymphatic system cancers, bone and pancreatic cancers, and in hamartomas.

11. The product according to claim 1, wherein said product is an inhibitor of AKT(PKB) phosphorylation.

12. A product having one of the following formulas:

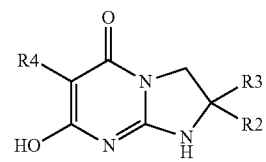

D

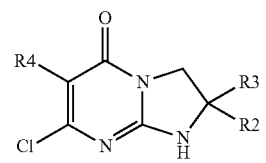

E

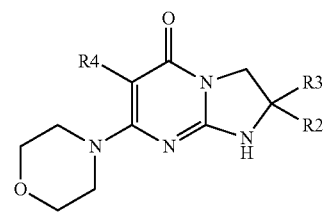

F

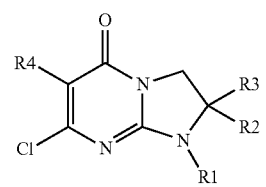

J in which R1, R2, R3 and R4 have the definitions indicated in claim 1.

13. A method of treating glycogenosis type II or Pompe disease in a patient in need thereof comprising administering to said patient a therapeutically effective amount of the product according to claim 1.

14. A method of treating malaria, Chagas disease or leishmaniasis in a patient in need thereof comprising administering to said patient a therapeutically effective amount of the product according to claim 1.

15. A process for preparing the product according to claim 1 according to Scheme 1 as defined hereinafter
Scheme 1:
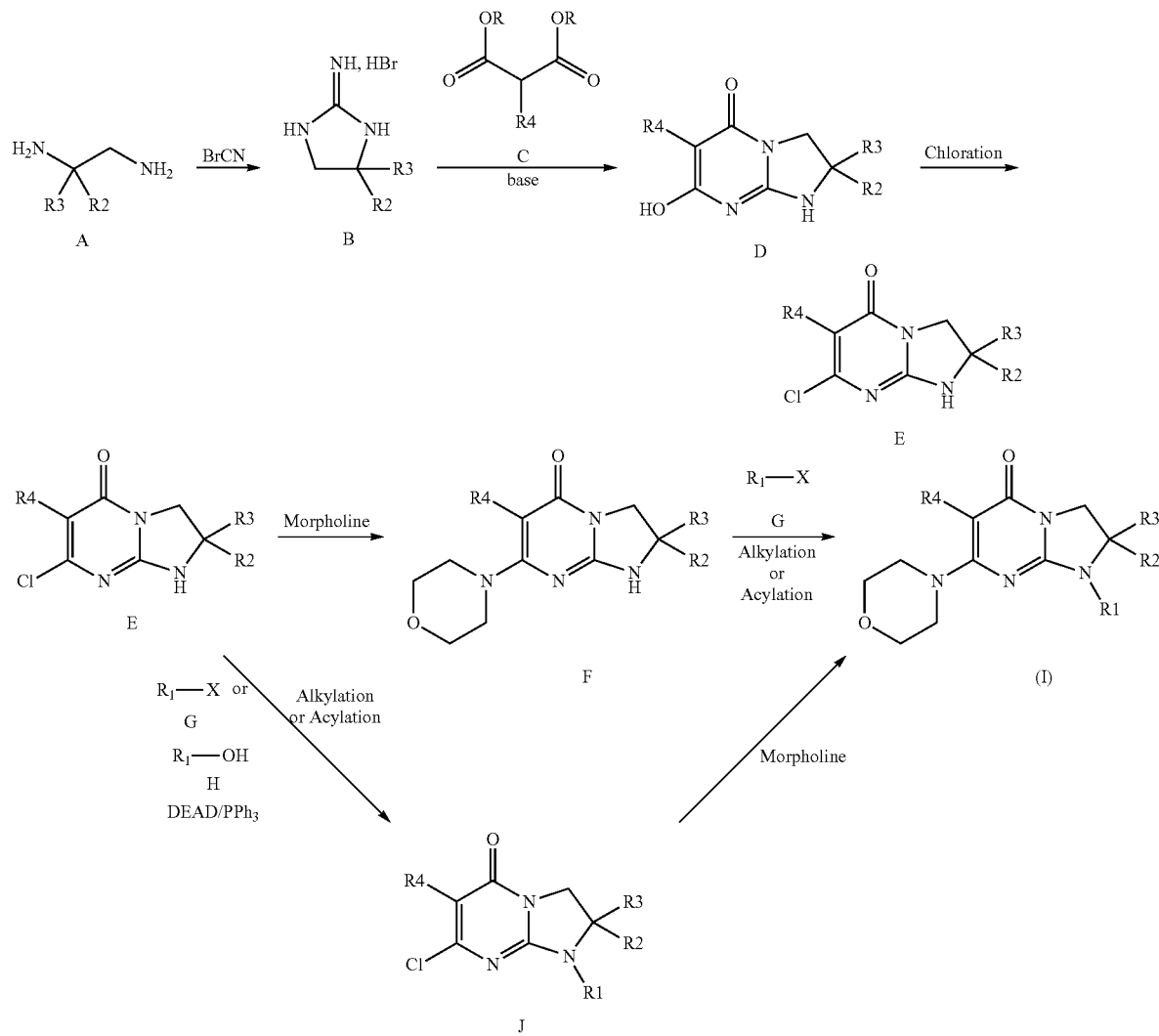
in which the substituents R1, R2, R3 and R4 have the meanings indicated in claim 1 and in which R represents alkyl, and X represents a chlorine, bromine or iodine atom or a sulphonyloxy group such as trifluoromethylsulphonyloxy.
* * * * *